(12) United States Patent
MacKinnon et al.

(10) Patent No.: US 8,283,126 B2
(45) Date of Patent: Oct. 9, 2012

(54) VOLTAGE SENSOR DOMAINS OF VOLTAGE-DEPENDENT ION CHANNEL PROTEINS AND USES THEREOF

(75) Inventors: Roderick MacKinnon, New York, NY (US); Alice Lee MacKinnon, New York, NY (US); Youxing Jiang, New York, NY (US); Vanessa Ruta, New York, NY (US)

(73) Assignee: The Rockefeller University, New York, NY (US)

( * ) Notice: Subject to any disclaimer, the term of this patent is extended or adjusted under 35 U.S.C. 154(b) by 112 days.

(21) Appl. No.: 12/970,192

(22) Filed: Dec. 16, 2010

(65) Prior Publication Data

US 2011/0159599 A1 Jun. 30, 2011

Related U.S. Application Data

(60) Division of application No. 12/141,367, filed on Jun. 18, 2008, now Pat. No. 7,888,046, which is a continuation of application No. 10/377,139, filed on Mar. 1, 2003, now Pat. No. 7,405,052.

(51) Int. Cl.
 *C07K 14/705* (2006.01)
 *G01N 33/566* (2006.01)

(52) U.S. Cl. ............ 435/7.2; 436/501; 530/350

(58) Field of Classification Search .......... None
 See application file for complete search history.

(56) References Cited

U.S. PATENT DOCUMENTS

| 5,368,712 A | 11/1994 | Tomich et al. |
| 5,538,863 A | 7/1996 | Price |

| 2002/0187524 A1 | 12/2002 | Curtis |
| 2005/0101767 A1 | 5/2005 | Clapham et al. |
| 2005/0267009 A1 | 12/2005 | Deagle |

OTHER PUBLICATIONS

Ruta et al., "Functional Analysis of an Archaebacterial Voltage-Dependent K+ Channel", Nature, vol. 422, 180-185 (2003).
Schoenherr et al., "Conformational Switch Between Slow and Fast Gating Modes: Allosteric Regulation of Voltage Sensor Mobility in the EAG K+ Channel", Neutron 2002, 35(5):935-949.
Bezanilla, "The Voltage Sensor in Voltage-Dependent Ion Channels", Physiological Reviews, 80(2)555-592, Apr. 2000.
Lee et al., "Structure of the KvAP Voltage-Dependent K+ Channel and its Dependence on the Lipid Membrane", PNAS 102(43)15441-15446 (2005).
Ruta et al., "Localization of the Voltage-Sensor Toxin Receptor on KvAP+", Biochemistry, 43, 10071-10079 (2004).
Jiang et al., "X-Ray Structure of a Voltage-Dependent K+ Channel" Nature, 423, 33-41 (2003).
Jiang et al., "The Principle of Gating Charge Movement in a Voltage-Dependent K+ Channel", Nature, 423, 42-48 (2003).
Sigworth, "Life's Transistors", Nature, 423, 21-22 (2003).
Gregerson, "The Voltage Sensor of Ion Channels Revealed", Trends in Endocrinology and Metabolism, 14:6, 251-252 (2003).
Kawarabaysai, "Complete Gerome Sequence of an Aerobic Hyperthermophilic Crenarchaeon, *Aeropyrum pernix* K1", DNA Research 6, 83-101 (1999).
Voges, "Recombinant Expression, Purification and Characterization of Kch, a Putative *Escherichia coli* Potassium Channel Protein", FEBS Letters, 429, 104-108 (1998).

*Primary Examiner* — John Ulm
(74) *Attorney, Agent, or Firm* — Hoffmann & Baron, LLP

(57) ABSTRACT

A composition of matter suitable for use in identifying chemical compounds that bind to voltage-dependent ion channel proteins, the composition comprising a screening protein that comprises an ion channel voltage sensor domain of the ion channel protein immobilized on a solid support.

22 Claims, 4 Drawing Sheets

VOLTAGE SENSOR DOMAINS OF VOLTAGE-DEPENDENT ION CHANNEL PROTEINS AND USES THEREOF

CROSS REFERENCE TO RELATED APPLICATIONS

This is a divisional application of U.S. application Ser. No. 12/141,367 filed on Jun. 18, 2008 now U.S. Pat. No. 7,888,046, which is a continuation of U.S. application Ser. No. 10/377,139, filed on Mar. 1, 2003 U.S. Pat. No. 7,405,052, the contents both of which are incorporated by reference.

The invention described in this application was made with funds from the National Institutes of Health, Grant Number GM43949 and GM47400. The United States government has certain rights in the invention.

BACKGROUND OF THE INVENTION

Many cells produce electrical impulses known as electrical activities (e.g., action potential) that propagate across their surface membrane. Action potentials travel quickly, and their arrival at a distant location initiates cellular processes such as the release of neurotransmitter molecules or the contraction of muscles (Hille B. Ion Channels of Excitable Membranes. Sinauer Associates, Inc. Sunderland, Mass., 2001). These electrical impulses are the means by which living cells transfer information over large distances in short time intervals.

Action potential theory contains two key elements (Hodgkin et al. *J. Physiol.* (*Lond*) 1952, 117:500-544). The first element is that the membrane of a cell can undergo transient changes in its selective permeability to, for example, $Na^+$ and $K^+$ ions. The second element is that the permeability changes depend on membrane voltage. These two elements create an interesting situation because selective permeability to ions determines the membrane voltage, while the voltage determines the permeability.

The family of protein molecules known as the voltage-dependent cation channels typically mediate electrical activity. This family includes potassium ($K^+$), sodium ($Na^+$) and calcium ($Ca^{2+}$) selective members. The opening of a pore of a voltage-dependent ion channel, a process known as gating, is dependent upon the membrane voltage. When the pore of a voltage-dependent cation channel opens, it selectively conducts predominantly its namesake ion.

It is believed that charged amino acids, called gating charges, move through the membrane electric field before the pore opens, allowing membrane voltage to bias the equilibrium between closed and opened conformations (Armstrong et al. *J. Gen. Physiol.* 1974, 63:533-552; Sigworth et al. *Q. Rev. Biophys.* 1994, 27:1-40; and Bezanilla *Physiol. Rev.* 2000, 80:555-592).

In $K^+$ channels, the gating charge per tetrameric channel corresponds to 12-14 electron charges (3.0-3.5 charges per subunit) crossing the entire membrane voltage difference. This large gating charge gives rise to a steep change in open probability as a function of membrane voltage.

All members of the voltage-dependent cation channel family typically contain six hydrophobic segments, S1 through S6 (S1-S6) (see FIGS. 1 and 2), per subunit. Four subunits (most often identical in $K^+$ channels and linked together as homologous 'domains' in $Na^+$ and $Ca_2^+$ channels) surround a central ion conduction pore. S5 through S6 line the pore and determine ion selectivity, while S1 through S4 form the voltage sensors. Certain charged amino acids within the voltage sensors account for most of the gating charge. These amino acids are particularly the first four arginines in S4.

Voltage-dependent ion channels are present in every cell and are involved in generation of electrical activity and information processing. As such, aberrant electrical activity can result in various conditions, such as heart arrhythmias, epilepsy, hypertension, etc.

There is a need for a composition and method for rapidly screening chemical compounds to determine whether the compounds bind to voltage-dependent ion channels.

SUMMARY OF THE INVENTION

In one embodiment, the invention relates to a composition of matter suitable for use in identifying chemical compounds that bind to voltage-dependent ion channel proteins. The composition comprises a screening protein that comprises an ion channel voltage sensor domain of the ion channel protein immobilized on a solid support.

In another embodiment, the invention relates to a kit suitable for use in identifying chemical compounds that bind to voltage-dependent ion channel proteins. The kit comprises a screening protein that comprises an ion channel voltage sensor domain of the ion channel protein and a solid support.

In another embodiment, the invention relates to a labeled screening protein suitable for use in identifying chemical compounds that bind to a voltage-dependent ion channel protein. The labeled screening protein comprising an ion channel voltage sensor domain of the ion channel protein and a detectable label.

In another embodiment, the invention relates to a method for screening for drug candidates that target voltage dependent ion channel protein. The method comprises providing a screening protein, contacting the screening protein with a chemical compound, determining whether the chemical compound binds to the screening protein, wherein chemical compounds that bind to the screening protein are drug candidates.

DETAILED DESCRIPTION OF THE INVENTION

Figure 1:
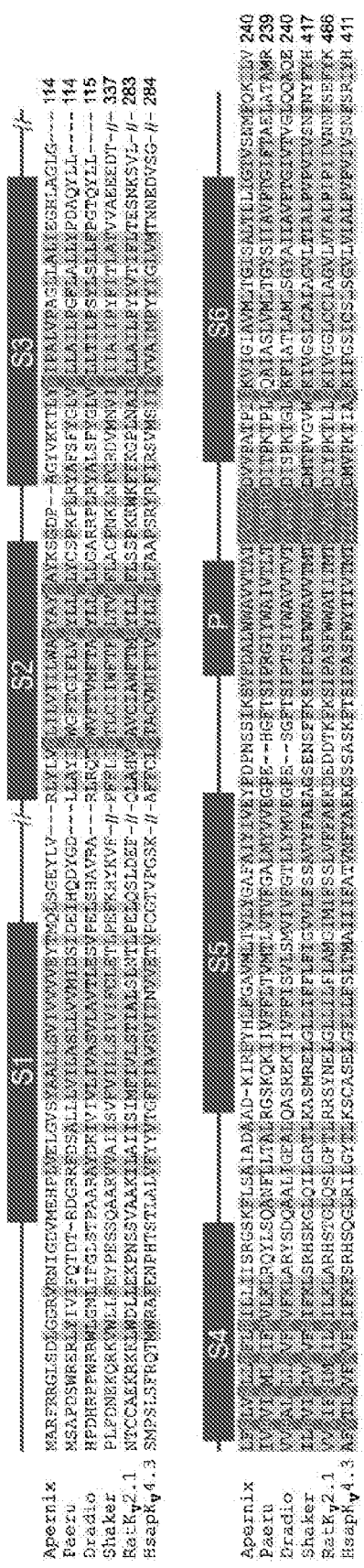
FIG. 1. Sequences of prokaryotic and eukaryotic voltage-dependent potassium (Kv) channels. Regions of high homology are colored in grey; functionally important residues are colored dark grey. Alignment was made with ClustalW followed by manual adjustment and exclusion of loops. The potassium channels are: Apernix, *Aeropyrum pernix* amino acid residues 14-253 of SEQ. ID. NO: 1 (Genbank Accession number GI: 5104624 (SEQ. ID. NO: 1); Paeru, *Pseudomonas aeruginosa* amino acid residues 1-239 of SEQ. ID. NO: 2 (Genbank Accession number GI: 15596693 (SEQ. ID. NO: 2)); Dradio, *Deinococcus radiodurans* amino acid residues 10-249 of SEQ. ID. NO: 3 (Genbank Accession number GI: 15805856 (SEQ. ID. NO: 3)); Shaker, *Drosophila melanogaster* amino acid residues 203-258 and 278-337 and amino acid residues 360-486 of SEQ. ID. NO: 4 (Genbank Accession number GI: 13432103 (SEQ. ID. NO: 4)); RatKv2.1, *Rattus norvegicus* amino acid residues 165-220 and 228-287 and 295-421 of SEQ. ID. NO: 5 (Genbank Accession number GI: 24418849 (SEQ. ID. NO: 5)); HsapKv4.3, *Homo sapiens* amino acid residues 159-214 and 225-411 of SEQ. ID. NO: 6 (Genbank Accession number GI: 5059060 (SEQ. ID. NO: 6)). The sequences corresponding to the above Genbank Accession numbers are hereby incorporated by reference.
Figure 2B:
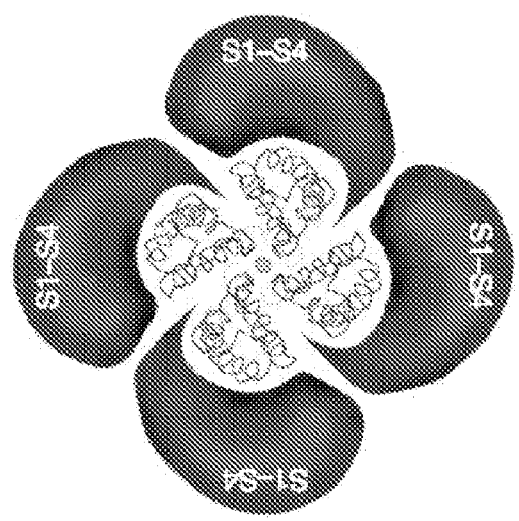
FIG. 2. Architecture of a voltage-dependent potassium channel. A) Transmembrane-spanning segments (S1-S6) are labelled; B) four subunits surround the pore. S1-S4 form the voltage sensor and S5-S6, including P, form the pore, represented by the KcsA potassium channel structure (backbone model).
Figure 2A:
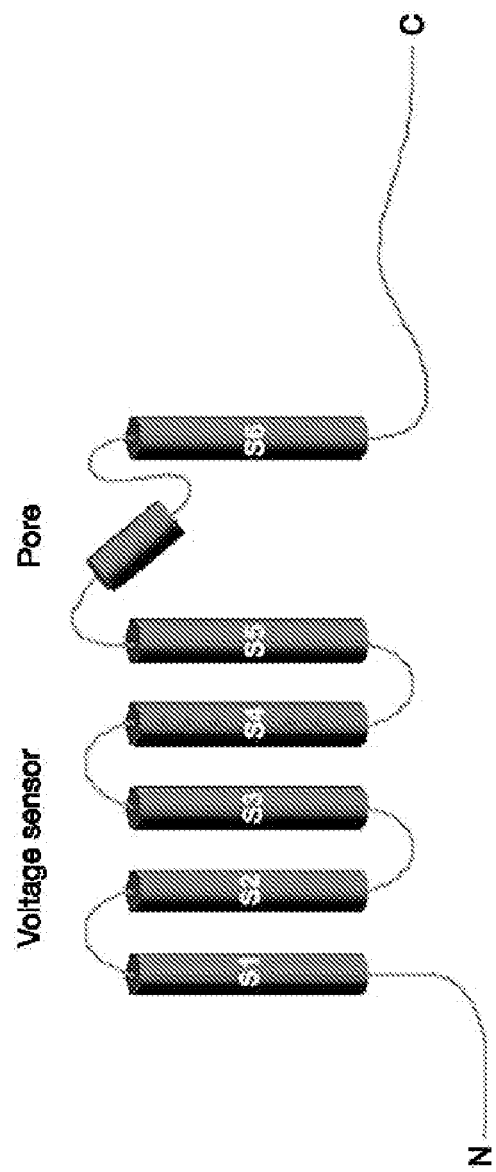

The invention is based on the surprising discovery by the inventors that a protein comprising a voltage sensor domain of a voltage-dependent ion channel protein retains its native structure, even when immobilized on a solid support. Such a protein is herein referred to as a screening protein. If the ion channel protein is full-length, the ion selectively is retained after reconstitution into planar lipid bilayers.

In one embodiment, the invention relates to a composition of matter suitable for use in screening chemical compounds in order to identify drug candidates that bind to voltage-dependent ion channel proteins. The composition comprises a voltage-dependent ion channel protein immobilized on a solid support. The protein may contain additional components often found on proteins, such as glycosylation units. Further additional components include lipids, sulfur groups, and phosphate groups.

Voltage-dependent ion channel proteins are selective for particular ions. Such ions include, for example, potassium, sodium, and calcium. Thus, the ion channel protein can be a potassium ion channel protein, a sodium ion channel protein, or a calcium ion channel protein.

The amino acid sequence of a voltage-dependent ion channel protein across species is highly conserved. Thus, the ion channel protein can be from an organism of any species.

For example, the species can be a prokaryotic organism. Some examples of prokaryotic organisms include archaebacteria and bacteria. An example of an archaebacteria is *Aeropyrum pernix*. Examples of bacteria include *Pseudomonas aeruginosa* and *Deinococcus radiodurans*. Preferably, the ion channel protein is an *Aeropyrum pernix* (Apernix) ion channel protein, such as KvAP. The amino acid sequence of Apernix KvAP, (amino acid residues of 14-253 of SEQ. ID. NO: 1) is shown in FIG. 1.

Alternatively, the species can be a eukaryotic organism. Examples of eukaryotic organisms include invertebrates, vertebrates, and mammals. Examples of invertebrates include insects, such as *Drosophila melanogaster* and mollusks. Examples of vertebrates include mammals, reptiles, and fish. Mammals include, for example, dogs, cats, horses, sheep, cows, rats, such as *Rattus norvegicus*, mice, and primates, including humans (i.e., *Homo sapiens*). The preferred eukaryotic ion channel protein is a *Homo sapien* ion channel protein.

The amino acid sequence homology for voltage-dependent potassium channel proteins of *Aeropyrum pernix, Pseudomonas aeruginosa, Deinococcus radiodurans, Drosophila melanogaster, Rattus norvegicus* and *Homo sapiens* is compared in FIG. 1. These amino acid sequence were predicted from the corresponding nucleic acid sequences disclosed in Genbank. The accession numbers are given in the brief description of FIG. 1 above.

The Genbank accession numbers of nucleic acid sequences that encode some calcium and sodium channel proteins, as well as some additional potassium channel proteins, are listed below.

Some examples of Genbank Accession numbers for voltage-dependent calcium channels include *Rattus norvegicus* calcium channel, voltage-dependent, T type, alpha 1G subunit, mRNA, Genbank Accession number GI:24429575 (SEQ. ID. NO: 7); *Homo sapiens* calcium channel, voltage-dependent, alpha 11 subunit(CACNA11) mRNA, Genbank Accession number GI:21361076 (SEQ. ID. NO: 8); *Mus musculus* calcium channel, voltage-dependent, L type, alpha 1C subunit (Cacna1c), mRNA, Genbank Accession number GI:6753227 (SEQ. ID. NO: 9); *Homo sapiens* calcium channel, voltage-dependent, alpha 1G subunit (CACNA1G), mRNA, Genbank Accession number GI:20070162 (SEQ. ID. NO: 10); and *Caenorhabditis elegans* calcium Channel, Alpha subunit CCA-1 (210.2 kD) (cca-1) mRNA, Genbank Accession number GI:25146600 (SEQ. ID. NO: 11).

Some examples of Genbank Accession numbers for voltage-dependent sodium channels include *Rattus norvegicus* sodium channel, voltage-gated, type11, alpha polypeptide (Scn11a), mRN, Genbank Accession number GI:15011860 (SEQ. ID. NO: 12); *Homo sapiens* sodium channel, voltage-gated, type I, alpha polypeptide (SCN1A), mRNA, Genbank Accession number GI:21914835 (SEQ. ID. NO: 13); *Rattus norvegicus* sodium channel, voltage-gated, type 8, alpha polypeptide (Scn8a), mRNA, Genbank Accession number GI:9507066 (SEQ. ID. NO: 14); *Mus musculus* sodium channel, voltage-gated, type XI, alpha polypeptide (Scn11a), mRNA, Genbank Accession number GI:6755405 (SEQ. ID. NO: 15); and *Bos taurus* mRNA for voltage-gated sodium channel alpha subunit, Genbank Accession number GI:18477464 (SEQ. ID. NO: 16).

Some examples of Genbank Accession numbers for voltage-dependent potassium channels include *D. melanogaster* ShB1 mRNA for Shaker gene, Genbank Accession number GI:288441 (SEQ. ID. NO: 17); *Homo sapiens* potassium voltage-gated channel, Shab-related subfamily, member 1 (KCNB1), mRNA, Genbank Accession number GI:27436972 (SEQ. ID. NO: 18); *Oryctolagus cuniculus* voltage-gated potassium channel Kv2.1 (KCNB1) mRNA, complete cds, Genbank Accession number GI:8572238 (SEQ. ID. NO: 19); *Xenopus laevis* Kv3.1 potassium channel mRNA, complete cds, Genbank Accession number GI:5817539 (SEQ. ID. NO: 20); and *Xenopus laevis* maxi-K potassium channel alpha subunit Slo mRNA, complete cds, Genbank Accession number GI:14582151 (SEQ. ID. NO: 21).

All the sequences corresponding to the above listed Genbank Accession numbers are hereby incorporated by reference.

As can be seen from FIGS. 1 and 2, an entire ion channel protein comprises (i) a voltage sensor and (ii) an ion-selective pore which includes a selectivity filter. The ion voltage sensor domain comprises segments S1-S4. The ion-selective pore comprises segments S5-S6. The selective filter comprises the signature sequence amino acids between P and S6.

The screening protein useful in the present invention comprises an ion channel voltage sensor domain. For example, the screening protein can comprise the entire ion channel protein. Preferably, the screening protein includes only (i.e., consists of or consists essentially of) the ion channel voltage sensor domain, i.e., segments S1-S4, and excludes an ion conduction (i.e., selective) pore as defined above.

In a more preferred embodiment, the screening protein comprises an amino acid sequence that consists essentially of the voltage sensor domain, i.e., includes segments S1-S4, and one or more additional amino acid residues that do not change the essential nature of the voltage sensor domain. The number of additional amino acid residues is preferably relatively small. In order to constitute a relatively small number of amino acids, the number of amino acid residues should not exceed approximately 100, preferably approximately 50, and more preferably approximately 10 amino acid residues. The additional amino acid residues may, for example, be relics of the method of isolating the voltage sensor domains In addition, one or more amino acid residues may be added to the screening protein for a specific purpose. For example, amino acids may be added for the purpose of labeling the screening protein or for attachment of the screening protein to a solid support. Examples of an amino acid sequence for attaching screening proteins to a solid support include hexa-histidine (e.g., $Co^{2+}$ column) and glutathione S-transferase.

The optional amino acids can be attached anywhere on the screening protein. Preferably, the optional amino acids are attached to either the N-terminus or C-terminus. The optional amino acids may also be added to any internal residue in the sequence of the screening protein, as long as the optional amino acids do not disrupt the native structure of the screening protein.

The screening protein can be a monomer or a polymer. Examples of polymers include dimers, trimers, tetramers, etc. There is no limit to the number of subunits that can polymerize, although screening proteins are typically not larger than tetramers.

The screening protein can be a functional analog of a naturally occurring voltage-dependent ion channel protein. An analog can, for example, be a substitution or deletion mutant of the ion channel protein. Substitutions and deletions can be made as long as the screening protein continues to satisfy the function of the voltage-dependent ion channel protein described herein.

Preferably, any substitutions of amino acids in a screening protein are conservative, i.e, within a group of amino acids having similar physicochemical characteristics. Amino acids may be grouped according to their physicochemical characteristics as follows:

(a) Non-polar amino acids: Ala(A) Ser(S) Thr(T) Pro(P) Gly(G);
(b) Acidic amino acids: Asn(N) Asp(D) Glu(E) Gln(O);
(c) Basic amino acids: His(H) Arg(R) Lys(K);
(d) Hydrophobic amino acids: Met(M) Leu(L) Ile(I) Val(V); and
(e) Aromatic amino acids: Phe(F) Tyr(Y) Trp(W).

During expression, the first five N-terminal amino acids may be replaced by a single leucine residue. Therefore, a screening protein where the first five N-terminal amino acids are replaced by a single leucine residue is considered to be a functional analog.

In one embodiment, the screening protein is immobilized on a solid support. The screening protein may be attached to the solid support by any method known in the art, and by any type of bond. The bond can be a covalent bond or a non-covalent bond. An example of a non-covalent bond is a hydrogen bond.

The solid support can be any support that is capable of immobilizing the screening protein. Examples of solid supports include a resin, a microtitre plate, and nitrocellulose paper. The resin may, for example, comprise cobalt, nickel, nickel-NTA agarose, and glutathione sepharose.

In another embodiment, the invention relates to a labeled screening protein suitable for use in identifying chemical compounds that bind to voltage-dependent ion channel proteins. The labeled screening protein comprises an ion channel voltage sensor domain of the ion channel protein and a detectable label. The screening protein may be any of the screening proteins described herein.

Methods for preparing a labeled protein are well known in the art. Some examples are described below.

The label may be radioactive. Some examples of useful radioactive labels include $^{32}P$, $^{125}I$, $^{131}I$, $^{35}S$, $^{14}C$, and $^{3}H$. Use of radioactive labels have been described in U.K. 2,034,323, U.S. Pat. No. 4,358,535, and U.S. Pat. No. 4,302,204.

Some examples of non-radioactive labels include enzymes and chromophores. Useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, in Ausubel, F. M. et al. (Eds.), Rotman 1961. Proc. Natl. Acad. Sci. USA 47:1981-1991, and by Current Protocols in Molecular Biology, John Wiley & Sons, Inc., New York (1999).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

In another embodiment, the invention relates to a kit suitable for use in identifying chemical compounds that bind to voltage-dependent ion channel proteins. The kit comprises a screening protein that comprises an ion channel voltage sensor domain of the ion channel protein and a solid support. The screening protein can comprise any screening protein described herein. The solid support present in the kit can be any support described herein.

The kit may further contain optional components that are helpful in preparing reagents and carrying out procedures described herein. Some examples of optional components include labels, nucleases, proteases, buffers, etc.

In another embodiment, the invention relates to a method for screening for drug candidates that target voltage-dependent ion channels. The first step in the method is providing a screening protein. Methods for preparing screening proteins by expression of the DNA encoding a screening protein in a host cell are described below.

The screening protein is contacted with a chemical compound. The chemical compound can be any molecule. Examples of molecules include biological molecules and small molecules. The chemical compounds can be a mixture of one or more different chemical compounds.

A biological molecule is any molecule which contains a polyamino acid, a polynucleotide, or a polysaccharide, and has a molecular weight greater than 450. Polyamino acids include proteins, polypeptides, and peptides.

Small molecules are typically organic compounds, including organometallic and organosilicon compounds, and the like, and generally have molecular weights of approximately 450 or less. Small molecules can further include molecules that would otherwise be considered biological molecules, except their molecular weight is not greater than 450. Thus, small molecules can include, monosaccharides, oligosaccharides, amino acids, oligopeptides, nucleotides, oligonucleotides, and their derivatives, having a molecular weight of 450 or less.

It is emphasized that a small molecule can have any molecular weight. They are merely called small molecules because they typically have molecular weights less than 450. Molecules with a molecular weight less than 450 typically do not qualify as biological molecules.

The screening protein can be contacted with the chemical compound by any method known to those in the art. Preferably, either the screening protein or the chemical compound is immobilized on a solid support.

For example, the screening protein may be immobilized on a resin. The screening protein can be contacted with the chemical compound by eluting the chemical compound through a column containing the screening protein immobilized on the resin.

Alternatively, the chemical compound may be immobilized on a microtitre plate. The screening proteins can be contacted with the chemical compound by incubating the plate with the chemical compound. Many chemical compounds may be immobilized on a plate, thereby allowing the rapid screening of the compounds.

The next step in screening is to determine whether the chemical compound binds to the screening proteins. Binding can be determined by any method known in the art.

For example, a label may be bound to the chemical compound or to the screening protein, depending on which is immobilized to the solid support. Usually, the component that is not immobilized is the component that is labeled. Thus, if the screening protein is immobilized, the chemical compound is labeled. If the chemical compound is immobilized, the screening protein is labeled.

After contacting the chemical compounds and the screening proteins as described above, detection of an immobilized label indicates the binding of screening proteins to a chemical compound. Such chemical compounds are drug candidates that target voltage dependent ion channel proteins.

Preferably, the drug candidate alters the function of the voltage dependent ion channel proteins, typically by causing the ion channel proteins either to stay open or to stay closed. For example, a drug candidate that causes the ion channel protein to stay closed inhibits the ion channel proteins. Any assay known to those in the art can be used to determine whether a drug candidate alters voltage dependent ion channels. An example of an assay is an electrophysological assay described in, for instance, Example 2, see below.

Electrical activity, (i.e., cellular electrical activity), whether normal or abberrant, is generated by voltage dependent ion channels, and therefore can be influenced by agents that affect voltage dependent ion channels. The drug candidate may be useful for treating any condition mediated by aberrant electrical activity, such as the magnitude of the resting membrane voltage, or shape and frequency of the action potential.

The condition can be, for example, asthma, hypertension, arrhythmia, epilepsy, nerve conduction abnormalities, atrial fibrillation, conditions associated with immune abnormalities due to, for instance, inappropriate lymphocyte stimulation, conditions associated with abnormalities of fluid and/or electrolyte secretion by, for example, epithelial membranes, such as in cystic fibrosis, and conditions associated with abnormal excretion by the renal system, such as in certain nephropathies, etc. Aberrant electrical activity can also initiate uptake or release of neurotransmitters, or initiate contraction of muscles.

The aberrant electrical activity can occur in any cell, organ or system in a body. Examples of cells include nerve cells, such as neurons, glial cell, and dendrites. Examples of organs and systems include heart, brain, lung, kidney, liver, muscle, digestive system, and peripheral nervous system. The muscle can be cardiac, skeletal, or smooth muscle.

The neurotransmitter can be any neurotransmitter. Examples of neurotransmitters include dopamine, epinephrine and norepinephrine.

Neurotransmitters are generally either excitatory neurotransmitters or inhibitory neurotransmitters. Excitatory neurotransmitter typically open cation channels, causing an influx of, for example, sodium, which depolarizes the postsynaptic membrane for firing an action potential. Examples of excitatory neurotransmitters include acetylcholine, glutamate, and serotonin.

Alternatively, inhibitory neurotransmitters usually suppresses firing of an action potential by keeping postsynaptic membranes polarized. Examples of inhibitory neurotransmitters include γ-aminobutyric acid and glycine.

These candidate drugs can be further tested for activity against a condition mediated by an aberrant electrical activity by methods known to those in the art. For example, the further testing can be those that are routinely done by clinicians and physicians during pre-clinical and clinical trials.

General Methods and Assays

The screening proteins may be prepared by methods that are well known in the art. Some general methods and techniques are described below. More specific methods and techniques are found in the specific examples below.

One method for producing screening proteins includes isolating or synthesizing DNA encoding the screening protein, and producing the recombinant protein by expressing the DNA, optionally in a recombinant vector, in a suitable host cell.

The proteins may also be made synthetically, i.e. from individual amino acids, or semisynthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997).

Nucleic acids encoding the proteins may also be synthesized in vitro. Suitable methods for synthesizing DNA are described by Caruthers et al. 1985. Science 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

Nucleic acid molecules encoding the ion channel proteins may be designed or assembled from known nucleic acid sequences encoding the ion channel proteins. The nucleic acid sequences may be obtained by those skilled in the art from collections of nucleic acid sequences, such as GenBank. Alternatively, the nucleic acid sequence may be derived from a known amino acid sequence of an ion channel protein using the genetic code, as is routine to those of skill in the art. The nucleic acid sequence may then be synthesized as described above. Similarly, the amino acid sequences of the screening proteins may be derived from the corresponding nucleic acid sequence.

The methods, constructs and host cells suitable for production of screening proteins in standard small-scale culture systems, as well as large-scale production systems, include fermenter systems, hollow fiber culture systems, tumbler systems, and suspension culture systems to name but a few.

Methods and procedures for the manipulation of nucleic acids, polymerase chain reaction (PCR) methods for amplification of nucleic acids, construction of expression vectors, transformation of host cells, and the culture of transformed cells for the production of protein are known. These and many more relevant methods may be found in a variety of laboratory manuals, texts and guides. For a general guide, see, for instance, Sambrook & Russel, (2001) Molecular Cloning, Third edition, Cold Spring Harbor Press. Other useful sources include: Ausubel et al., 1992 Short Protocols in Molecular Biology, Second edition, John Wiley & Son; Gene Expression Technology, Methods in Enzymology Vol. 185 (ed. David Goeddel et al., Academic Press, Inc., London, 1991); Gene Structure and Expression, Second Edition, J. D. Hawkins (Cambridge University Press, London, 1991); PCR Protocols: A Guide to Methods and Applications (Innis, et al. 1990, Academic Press, San Diego, Calif.); Methods in Molecular Biology (Vol. 7), Gene Transfer and Expression Protocols, (ed. E. J. Murray, 1991, The Humana Press Inc., Clifton, N.J.).

The nucleic acid encoding screening proteins may be replicated and expressed in a suitable host cell. Suitable host cells include prokaryotic host cells and eukaryotic host cells. Suitable prokaryotic host cells include *E. coli* cells which are preferred. Suitable eukaryotic host cells include yeast cells, insect cells and mammalian cells, the latter being preferred.

Screening proteins are expressed in eukaryotic hosts in preference to prokaryotic hosts in cases where the protein must be post-transcriptionally modified. Examples of post-transcriptional modification include glycosylation, phosphorylation, disulfide bond formation, oligomerization and specific cleavage of the transcribed protein product.

Prokaryotic hosts do not perform certain post-transcriptional modifications of ion channel proteins, such as for instance glycosylation. For this reason expression in eukaryotic systems is preferred despite the higher costs associated with production of biologics in eukaryotic systems as compared with the costs of biologics produced in prokaryotic host systems.

Prokaryotic host systems are preferred for expression and production of screening proteins of the invention that do not require post-transcriptional modifications that are unique to eukaryotic systems and where the screening proteins are correctly folded or may be refolded in vitro.

Many standard well known cloning and expression and isolation/purification techniques that reflect the state of the art in recombinant DNA and protein methods are described in detail in Sambrook & Russel, *Molecular Cloning: A Laboratory Manual*, Third Edition, Cold Spring Harbor Laboratory Press, Cold Spring Harbor, N.Y. (2001). Techniques for expression of cloned genes in *E. coli* and in mammalian cells is described in detail in Chapters 15 and 16-17, respectively of the Sambrook & Russel Laboratory Manual (Id).

Labels

The labels may be conjugated to the screening protein or chemical compound by methods that are well known in the art. The labels may be directly attached through a functional group on the screening protein or chemical compound. The screening protein or chemical compound either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the screening protein or chemical compound by means of coupling agents, such as dialdehydes, carbodiimides, dimaleimides, and the like.

EXAMPLES

Example 1

Preparation of *Aeropyrum pernix* KvAP

A sample of *Aeropyrum pernix* was obtained from the Japan Collection of Microorganisms. *Aeropyrum pernix* cultures were grown in a solution of autoclaved sea water supplemented with bactoyeast extract, trypticase peptone and sodium thiosulphate for three days in an oil bath maintained at 95° C.

*Aeropyrum pernix* genomic DNA was collected by standard procedures. The gene coding for KvAP starting from methionine 14 was cloned by polymerase chain reaction (PCR) amplification of the genomic DNA and inserted into the protein expression vector pQE60 (Qiagen) between NcoI and BglII restriction endonuclease sites with a thrombin cleavage site between a carboxy-terminal hexahistidine sequence and the channel.

Channel protein was expressed in XL1-blue cell cultures grown in LB medium supplemented with 10 mM BaCl2 on induction with 0.4 mM isopropyl-b-D-thiogalactopyranoside (IPTG). Expressed protein was extracted with 40 mM decylmaltoside (DM) and purified on a Talon $Co^{2+}$ affinity column (Clontech).

The protein was maintained in 5 mM DM, 20 mM Tris, pH 8.0, and 100 mM KCl. Nonspecifically bound protein was washed using 15 mM imidazole added to the above buffer, and the channel then eluted with 400 mM imidazole. Immediately after elution, 1.0 unit of thrombin (Roche) per 3.0 mg channel was added to cleave the hexahistidine sequence overnight at room temperature. Protein was concentrated to about 15 mg $ml^{-1}$ and run on a Superdex-200 (10/30) column (Pharmacia) in the above buffer.

MALDI-TOF mass spectrometry (PerSeptive Biosystems Voyager-STR) and N-terminal sequencing analysis (Rockefeller University Protein/DNA Technology Center) indicated that the KvAP protein undergoes a modification during expression in which the first five residues of the encoded construct are replaced with a single leucine residue in the expressed channel protein.

Example 2

KvAP of Prokaryotic Organism, *Aeropyrum pernix*, is Functionally Similar to Eukaryotic Kv Channels KvAP channels were expressed in *Escherichia coli*, extracted with decylmaltoside, purified and reconstituted into planar lipid bilayers of 1-palmitoyl-2-oleoyl-phosphotidylglycerol (POPG) and 1-palmitoyl-2-oleoyl-phosphotidylethanolamine (POPE) for functional studies.

KvAP channels have a large conductance—the slope of the single-channel current—voltage relationship recorded in solutions containing 150 mM KCl and 10 mM HEPES, pH 7.0, on both sides of the membrane shows a conductance of approximately 170 pS. The presence of the $K^+$ channel signature sequence indicates that the KvAP pore should be strongly selective for $K^+$ versus $Na^+$ ions.

To examine ion selectivity, the reversal potential of macroscopic tail currents in a tenfold $K^+$ gradient by substituting 135 mM NaCl for 135 mM KCl in the solution on one side of the membrane. The measured reversal potential is $-56.5 \pm 1.2$ mV, which is near the Nernst potential for a perfectly $K^+$ selective pore at room temperature (21° C.).

Example 3

KvAP of Prokaryotic Organism, *Aeropyrum pernix*, is Structurally Similar to Eukaryotic Kv Channels To examine the structural similarity of KvAP to eukaryotic $K^+$ channel pores, the ability of a small protein toxin from scorpion venom to inhibit the KvAP channel was examined.

Venomous animals, such as scorpions, exploit the conservation of ion-channel structure by producing a toxin that recognizes a structural feature common to an entire family of ion channels. By making many sequence variants of the same basic toxin structure, a scorpion can inhibit virtually every member of an ion channel family. The scorpion Leiurus quinquestriatus hebraeus specializes in a family of pore-blocking toxins, exemplified by charybdotoxin (CTX), which fit, like a key to a lock, to the pore entryway of $K^+$ channels.

CTX inhibits the KvAP channel with a dissociation constant (Kd) of about 0.4 mM. We emphasize that CTX would not bind to the KvAP channel if its pore were not very similar in structure to that of eukaryotic $K^+$ channels.

Example 4

Voltage-Dependence of KvAP is Similar to Eukaryotic Kv Channels

To determine the orientation of channels incorporated into planar lipid bilayers, we used CTX, which causes inhibition by binding only to the extracellular side. KvAP channels open in response to membrane depolarization (e.g., when the voltage of the CTX-insensitive (intracellular) side of the membrane is made positive relative to the CTX-sensitive (extracellular) side. KvAP channels are strongly voltage-dependent, opening as a function of membrane voltage, similar to Shaker and other eukaryotic neuronal Kv channels.

Example 5

Isolation of KvAP Voltage Sensor (S1-S4)

DNA for the isolated voltage sensor (from KvAP) encoding Met1 to Lys147 was cloned into a pQE60 expression vector (Qiagen) between NcoI and BglII sites with a thrombin cleavage site followed by a C-terminal hexahistadine sequence.

Protein was expressed in *E. coli* XL1-Blue cells by induction (at $A_{600}$~1.0) with 0.4 mM isopropyl-β-D-thiogalacto-pyranoside (IPTG) for 4 hours at 37° C. Cells were harvested and lysed in 50 mM Tris, pH 8.0, 100 mM KCl, containing 1 μg ml$^{-1}$ Leupeptin, 1 μg ml$^{-1}$ Pepstatin, 2 μg ml$^{-1}$ Aprotinin and 1 mM PMSF (Sigma) to inhibit proteases.

Protein was then extracted from the cell lysate for 3 hours at room temperature in the above solution by adding 40 mM decylmaltoside (DM). The extracted cell lysate was centrifuged at 16,000 rpm for 20 minutes and the supernatant was collected and loaded onto a Talon $Co^{2+}$ affinity column (Clontech) equilibrated in 5 mM DM, 20 mM Tris, pH 8.0, and 100 mM KCl. Nonspecifically bound protein was washed using 10 mM imidazole added to the above buffer, and the voltage sensor domain was eluted with 300 to 400 mM imidazole in the above buffer. The isolated voltage sensor domain was then dialyzed against 100 ml of the above buffer for ~7-8 hours and transferred to 100 ml of fresh buffer for dialysis overnight. Voltage sensor domain was concentrated to ~5 mg ml$^{-1}$, calculated by 280 nm absorbance using the extinction coefficient $\epsilon=1.01$ (mg ml$^{-1}$*cm)$^{-1}$ determined from amino acid analysis. Purification yields ~3 mg of voltage sensor domain protein per liter of bacterial culture.

Analysis by MALDI-TOF mass spectrometry (PerSeptive Biosystems Voyager-STR) and N-terminal sequencing indicated that the N-terminus undergoes modification during expression in which the first five residues of the encoded constructs are replaced with a single leucine residue.

Example 6

Isolated Voltage Sensor Domain Retains Native Structure and Isolates and Binds to Toxins Isolated voltage sensor was expressed and purified according to Example 5. To generate the voltage sensor domain column for isolation of toxins, 0.1 ml of $Co^{2+}$ resin was washed with water and then equilibrated with Buffer A (20 mM Tris pH 8.0, 100 mM KCl, and 10 mM DM) in an eppendorf tube by 3-4 rounds of centrifugation (500 rpm) to collect resin, careful removal of the supernatant with a pipette and resuspension of the resin in either 1 ml of water or 0.4 ml of Buffer A.

Approximately 2 mg of voltage sensor domain was added to the equilibrated resin. The resin and voltage sensor domain protein were incubated for ~15 minutes. The resin was then applied to a micro chromatography column (Biorad). Samples of the voltage sensor domain prior to addition to the resin and the flow through after addition of resin to the column was kept and later run on an SDS gel to ensure that an excess of protein has been added to the resin and saturated with protein.

The column was washed twice with 2 column volumes of Buffer A to remove any remaining unbound voltage sensor domain protein. A control column was prepared containing 0.1 ml of resin treated equivalently with the exception that instead of adding voltage sensor domain protein to the equilibrated resin, the same volume of Buffer A was added.

Venom from *Grammostola spatulata* (SpiderPharm) was diluted ten fold in Buffer A and 0.1 ml of the venom stock was applied to the column with bound S1-S4 domain or the control column. Both columns were washed to minimize non-specifically bound toxins, first in 4 column volumes Buffer A and then 4 column volumes Buffer A with 10 mM imidazole.

Remaining protein was eluted from both columns with 0.1 ml of Buffer A containing 400 mM imidazole and reduced with 50 mM DTT at 37° C. for 2 hours to improve separation by reverse phase high performance liquid chromatography (HPLC). Equal volumes of eluted, reduced protein from the two columns were run on an Agilent 1100 Series HPLC with a C-18 reverse-phase 5 μm 80 Å column using a 2 min isocratic flow of 75% mobile phase A ($H_2O$, 0.1% TFA) and 25% mobile phase B (90% acetonitrile, 10% $H_2O$, 0.1% TFA) followed by a 25%-55% mobile phase B gradient over 40 minutes. Peaks are collected and analyzed by MALDI-TOF mass spectrometry focusing on the low molecular weight range (~800-10,000 Da).

Figure 3:
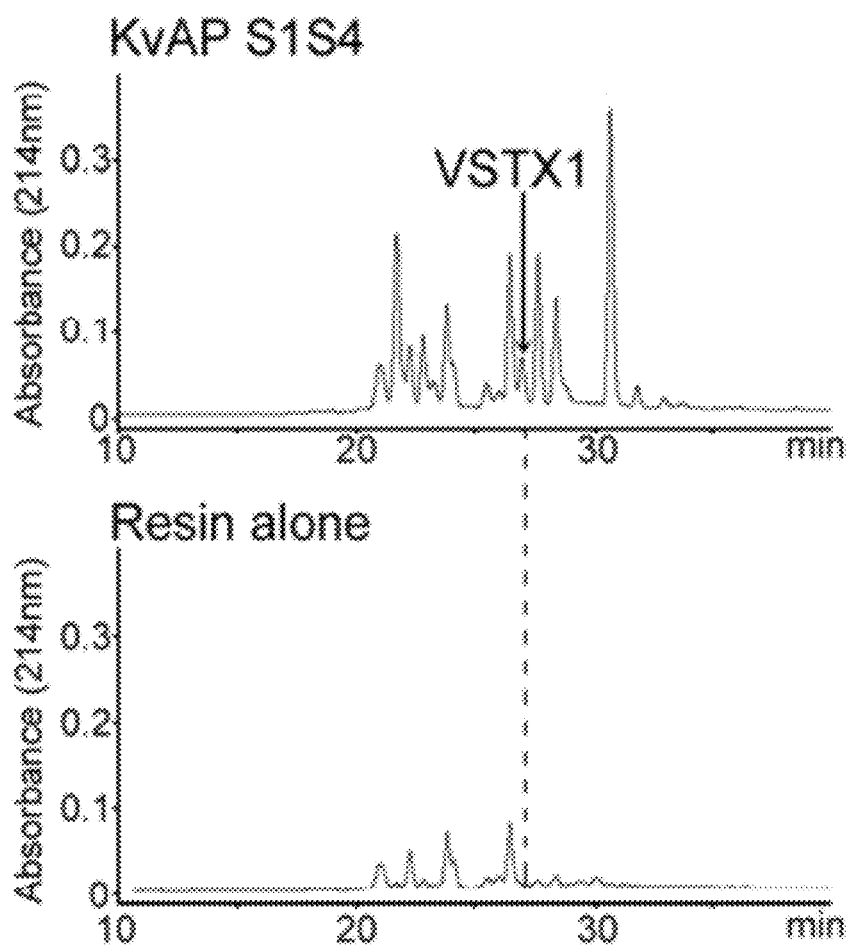
FIG. 3. Functional and structural analysis of the isolated voltage sensor domain. A) The isolated voltage sensor retains its ability to bind tarantula toxins that specifically inhibit voltage sensors. Quantitative reverse phase HPLC chromatogram of toxins eluted from a $Co^{2+}$ affinity column in the presence (top) or absence (bottom) of the voltage sensor domain. B) VSTX1, eluted at the position marked with an arrow (in FIG. 3A), binds to the domain and inhibits KvAP channel currents elicited by a +100 mV depolarization.
Figure 3B:
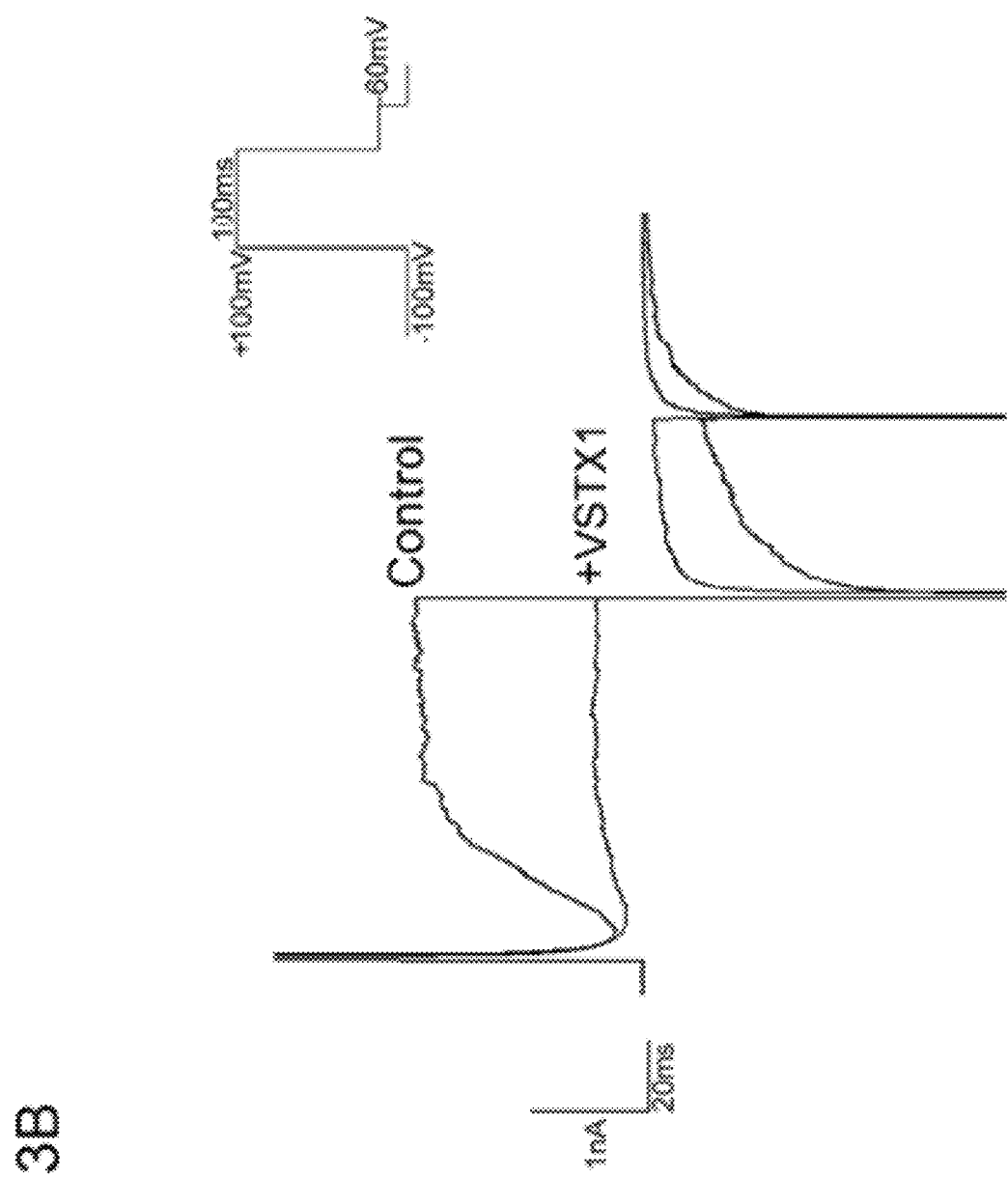

The isolate voltage sensor immobilized to a resin in the column efficiently purifies toxins from tarantula venom (FIG. 3A). These toxins also inhibit functional KvAP channels in an electrophysiological assay (FIG. 3B).

Thus, the data show that the isolated voltage sensor retains native structure due to binding of protein toxins with high affinity to the voltage sensor.

These experiments were performed with voltage-dependent ion channels from *Aeropyrum pernix*. However, due to the close homology between the amino acid sequences of voltage-dependent ion channels across species, the present invention can be applied to voltage sensor domains from any species, including *Homo sapiens*

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Dec. 16, 2010. The sequence listing.txt file is 133 kb in size.

What is claimed is:

1. A composition of matter suitable for use in identifying chemical compounds that bind to a voltage-dependent sodium ion channel protein, the composition comprising a screening protein consisting essentially of a sodium ion channel voltage sensor domain having transmembrane segments S1-S4 of the ion channel protein immobilized on a solid support.

2. The composition of claim 1, wherein the solid support is a resin.

3. The composition of claim 2, wherein the resin comprises cobalt.

4. The composition of claim 2, wherein the resin comprises nickel.

5. The composition of claim 4, wherein the nickel is nickel-NTA agarose.

6. The composition of claim 2, wherein the resin comprises glutathione sepharose.

7. A kit suitable for use in identifying chemical compounds that bind to a voltage-dependent ion channel protein, the kit comprising a screening protein consisting essentially of a sodium ion channel voltage sensor domain having transmembrane segments S1-S4 of the ion channel protein and a solid support.

8. The kit of claim 7, wherein the solid support is a resin.

9. The kit of claim 8, wherein the resin comprises cobalt.

10. The kit of claim 8, wherein the resin comprises nickel.

11. The kit of claim 10, wherein the nickel is nickel-NTA agarose.

12. The kit of claim 8, wherein the resin comprises glutathione sepharose.

13. A labeled screening protein suitable for use in identifying chemical compounds that bind to a voltage-dependent sodium ion channel protein, the labeled screening protein consisting essentially of a sodium ion channel voltage sensor domain having transmembrane segments S1-S4 of the ion channel protein and a detectable label.

14. The labeled screening protein of claim 13, wherein the detectable label is radioactive.

15. The labeled screening protein of claim 13, wherein the detectable label is colorimetric.

16. A method for screening for drug candidates that target voltage dependent sodium ion channel protein, the method comprising:
    providing a screening protein consisting essentially of a sodium ion channel voltage sensor domain having transmembrane segments S1-S4 of the ion channel protein;
    contacting the screening protein with a chemical compound;
    determining whether the chemical compound binds to the screening protein;
    wherein chemical compounds that bind to the screening protein are drug candidates.

17. A method according to claim 16, wherein the screening protein is immobilized on a solid support.

18. A method according to claim 16, wherein the chemical compound is immobilized on a solid support.

19. A method according to claim 16, wherein the chemical compound is a biological molecule.

20. A method according to claim 19, wherein the biological molecule is a polyamino acid.

21. A method according to claim 16, wherein the chemical compound is a small molecule.

22. A method according to claim 16, wherein the drug candidate alters the target voltage dependent ion channel proteins.

* * * * *

UNITED STATES PATENT AND TRADEMARK OFFICE
CERTIFICATE OF CORRECTION

PATENT NO. : 8,283,126 B2
APPLICATION NO. : 12/970192
DATED : October 9, 2012
INVENTOR(S) : MacKinnon et al.

It is certified that error appears in the above-identified patent and that said Letters Patent is hereby corrected as shown below:

IN THE SPECIFICATION:

Column 1, line 62

Now reads: "$Na^+$ and $Ca_2^+$";

Should read: -- $Na^+$ and $Ca^{2+}$ --.

Column 5, line 6

Now reads: "voltage sensor domains";

Should read: -- voltage sensor domains. --.

Column 5, line 40

Now reads: "Glu(E) Gln(O)";

Should read: --Glu(E) Gln(Q) --.

Column 12, line 60

Now reads: "*Homo Sapiens*";

Should read: -- *Homo sapiens.* --.

Signed and Sealed this
Tenth Day of September, 2013

Teresa Stanek Rea
*Acting Director of the United States Patent and Trademark Office*

Column 12, lines 66 and 67

Now reads: "sequence listing.txt";

Should read: -- sequence_listing.txt --.

SEQUENCE LISTING

<160> NUMBER OF SEQ ID NOS: 21

<210> SEQ ID NO 1
<211> LENGTH: 295
<212> TYPE: PRT
<213> ORGANISM: Aeropyrum pernix

<400> SEQUENCE: 1

```
Met Ser Val Glu Arg Trp Val Phe Pro Gly Cys Ser Val Met Ala Arg
  1               5                  10                  15

Phe Arg Arg Gly Leu Ser Asp Leu Gly Gly Arg Val Arg Asn Ile Gly
             20                  25                  30

Asp Val Met Glu His Pro Leu Val Glu Leu Gly Val Ser Tyr Ala Ala
         35                  40                  45

Leu Leu Ser Val Ile Val Val Val Glu Tyr Thr Met Gln Leu Ser
     50                  55                  60

Gly Glu Tyr Leu Val Arg Leu Tyr Leu Val Asp Leu Ile Leu Val Ile
 65                  70                  75                  80

Ile Leu Trp Ala Asp Tyr Ala Tyr Arg Ala Tyr Lys Ser Gly Asp Pro
                 85                  90                  95

Ala Gly Tyr Val Lys Lys Thr Leu Tyr Glu Ile Pro Ala Leu Val Pro
            100                 105                 110

Ala Gly Leu Leu Ala Leu Ile Glu Gly His Leu Ala Gly Leu Gly Leu
        115                 120                 125

Phe Arg Leu Val Arg Leu Leu Arg Phe Leu Arg Ile Leu Leu Ile Ile
    130                 135                 140

Ser Arg Gly Ser Lys Phe Leu Ser Ala Ile Ala Asp Ala Ala Asp Lys
145                 150                 155                 160

Ile Arg Phe Tyr His Leu Phe Gly Ala Val Met Leu Thr Val Leu Tyr
                165                 170                 175

Gly Ala Phe Ala Ile Tyr Ile Val Glu Tyr Pro Asp Pro Asn Ser Ser
            180                 185                 190

Ile Lys Ser Val Phe Asp Ala Leu Trp Trp Ala Val Val Thr Ala Thr
        195                 200                 205

Thr Val Gly Tyr Gly Asp Val Val Pro Ala Thr Pro Ile Gly Lys Val
    210                 215                 220

Ile Gly Ile Ala Val Met Leu Thr Gly Ile Ser Ala Leu Thr Leu Leu
225                 230                 235                 240

Ile Gly Thr Val Ser Asn Met Phe Gln Lys Ile Leu Val Gly Glu Pro
                245                 250                 255

Glu Pro Ser Cys Ser Pro Ala Lys Leu Ala Glu Met Val Ser Ser Met
            260                 265                 270

Ser Glu Glu Glu Phe Glu Phe Val Arg Thr Leu Lys Asn Leu Arg
        275                 280                 285

Arg Leu Glu Asn Ser Met Lys
    290                 295
```

<210> SEQ ID NO 2
<211> LENGTH: 283
<212> TYPE: PRT
<213> ORGANISM: Pseudomonas aeruginosa

<400> SEQUENCE: 2

```
Met Ser Ala Pro Asp Ser Trp Arg Glu Arg Leu Tyr Ile Val Ile Phe
  1               5                  10                  15
```

```
Gln Thr Asp Thr Arg Asp Gly Arg Arg Phe Asp Ser Ala Leu Leu Leu
             20                  25                  30

Val Ile Leu Ala Ser Leu Leu Val Met Ile Asp Ser Ile Asp Glu
             35                  40                  45

Ile His Gln Asp Tyr Gly Asp Leu Leu Ala Tyr Ile Glu Trp Gly Phe
 50                      55                  60

Thr Gly Ile Phe Leu Val Glu Tyr Leu Leu Arg Leu Tyr Cys Ser Pro
 65                  70                  75                  80

Lys Pro Leu Arg Tyr Ala Phe Ser Phe Tyr Gly Leu Val Asp Leu Leu
                 85                  90                  95

Ala Ile Leu Pro Gly Phe Leu Ala Leu Leu Tyr Pro Ala Gln Tyr
            100                 105                 110

Leu Leu Ile Val Arg Val Ile Arg Met Leu Arg Ile Phe Arg Val Leu
            115                 120                 125

Lys Leu Arg Gln Tyr Leu Ser Gln Ala Asn Phe Leu Leu Thr Ala Leu
            130                 135                 140

Arg Gly Ser Lys Gln Lys Ile Ile Val Phe Phe Leu Thr Val Met Thr
145                 150                 155                 160

Leu Val Thr Val Phe Gly Ala Leu Met Tyr Val Val Glu Gly Pro Glu
                165                 170                 175

His Gly Phe Thr Ser Ile Pro Arg Gly Ile Tyr Trp Ala Ile Val Thr
            180                 185                 190

Leu Thr Thr Val Gly Phe Gly Asp Ile Thr Pro Lys Thr Pro Leu Gly
            195                 200                 205

Gln Ala Ile Ala Ser Leu Val Met Leu Thr Gly Tyr Ser Ile Ile Ala
            210                 215                 220

Val Pro Thr Gly Ile Phe Thr Ala Glu Leu Ala Thr Ala Met Arg Gln
225                 230                 235                 240

Asp Pro Ala Asn Leu Leu Gln Arg Asp Cys Pro Val Cys Arg Lys Ala
                245                 250                 255

Thr His Glu Val Gln Ala Ala Phe Cys Cys Arg Cys Gly Asn Pro Leu
            260                 265                 270

Phe Pro Arg Glu Glu Gly Ser His Gly Lys Ser
            275                 280

<210> SEQ ID NO 3
<211> LENGTH: 280
<212> TYPE: PRT
<213> ORGANISM: Deinococcus radiodurans

<400> SEQUENCE: 3

Met Ile Ser Pro Pro Pro Asp Pro Pro His Pro Asp His Arg Pro Pro
1               5                  10                  15

Trp Arg Arg Trp Leu Gly Asn Leu Ile Phe Gly Leu Ser Thr Pro Ala
             20                  25                  30

Ala Arg Ala Tyr Asp Lys Ile Val Ile Val Leu Ile Val Ala Ser Val
             35                  40                  45

Leu Ala Val Thr Leu Glu Ser Val Pro Glu Leu Ser His Ala Val Arg
 50                  55                  60

Ala Arg Leu Arg Gln Thr Glu Trp Val Phe Thr Val Met Phe Thr Ala
 65                  70                  75                  80

Asp Tyr Leu Leu Arg Leu Leu Gly Ala Arg Pro Leu Arg Tyr Ala
                 85                  90                  95

Leu Ser Phe Tyr Gly Leu Val Asp Leu Leu Thr Ile Leu Pro Ser Tyr
            100                 105                 110
```

```
Leu Ser Leu Leu Phe Pro Gly Thr Gln Tyr Leu Leu Val Val Arg Ala
            115                 120                 125

Leu Arg Leu Leu Arg Val Phe Arg Val Phe Lys Leu Ala Arg Tyr Ser
130                     135                 140

Asp Gln Ala Ala Leu Ile Gly Glu Ala Leu Gln Ala Ser Arg Glu Lys
145                 150                 155                 160

Ile Ile Val Phe Phe Ile Ser Val Leu Ser Met Val Ile Val Phe Gly
                165                 170                 175

Thr Leu Leu Tyr Met Val Glu Gly Pro Glu Ser Gly Phe Thr Ser Ile
            180                 185                 190

Pro Thr Ser Ile Tyr Trp Ala Val Val Thr Val Thr Val Gly Tyr
        195                 200                 205

Gly Asp Ile Ser Pro Lys Thr Gly Leu Gly Lys Phe Ile Ala Thr Leu
210                 215                 220

Ala Met Leu Ser Gly Tyr Ala Ile Ile Ala Val Pro Thr Gly Ile Val
225                 230                 235                 240

Thr Val Gly Leu Gln Gln Ala Gln Glu Ala Arg Arg Gly Arg Thr Cys
                245                 250                 255

Pro Gln Cys Gly Leu Ser Arg His Asp Ala Asp Ala Arg Phe Cys Lys
            260                 265                 270

Arg Cys Gly Glu Asn Leu Pro Gly
        275                 280

<210> SEQ ID NO 4
<211> LENGTH: 656
<212> TYPE: PRT
<213> ORGANISM: Drosophila melanogaster

<400> SEQUENCE: 4

Met Ala Ala Val Ala Gly Leu Tyr Gly Leu Gly Glu Asp Arg Gln His
1               5                   10                  15

Arg Lys Lys Gln Gln Gln Gln Gln His Gln Lys Glu Gln Leu Glu
            20                  25                  30

Gln Lys Glu Glu Gln Lys Lys Ile Ala Glu Arg Lys Leu Gln Leu Arg
        35                  40                  45

Glu Gln Gln Leu Gln Arg Asn Ser Leu Asp Gly Tyr Gly Ser Leu Pro
50                  55                  60

Lys Leu Ser Ser Gln Asp Glu Glu Gly Gly Ala Gly His Gly Phe Gly
65                  70                  75                  80

Gly Gly Pro Gln His Phe Glu Pro Ile Pro His Asp His Asp Phe Cys
                85                  90                  95

Glu Arg Val Val Ile Asn Val Ser Gly Leu Arg Phe Glu Thr Gln Leu
            100                 105                 110

Arg Thr Leu Asn Gln Phe Pro Asp Thr Leu Leu Gly Asp Pro Ala Arg
        115                 120                 125

Arg Leu Arg Tyr Phe Asp Pro Leu Arg Asn Glu Tyr Phe Phe Asp Arg
130                 135                 140

Ser Arg Pro Ser Phe Asp Ala Ile Leu Tyr Tyr Tyr Gln Ser Gly Gly
145                 150                 155                 160

Arg Leu Arg Arg Pro Val Asn Val Pro Leu Asp Val Phe Ser Glu Glu
                165                 170                 175

Ile Lys Phe Tyr Glu Leu Gly Asp Gln Ala Ile Asn Lys Phe Arg Glu
            180                 185                 190

Asp Glu Gly Phe Ile Lys Glu Glu Glu Arg Pro Leu Pro Asp Asn Glu
        195                 200                 205
```

-continued

```
Lys Gln Arg Lys Val Trp Leu Leu Phe Glu Tyr Pro Glu Ser Ser Gln
210                 215                 220

Ala Ala Arg Val Val Ala Ile Ile Ser Val Phe Val Ile Leu Leu Ser
225                 230                 235                 240

Ile Val Ile Phe Cys Leu Glu Thr Leu Pro Glu Phe Lys His Tyr Lys
                245                 250                 255

Val Phe Asn Thr Thr Thr Asn Gly Thr Lys Ile Glu Glu Asp Glu Val
            260                 265                 270

Pro Asp Ile Thr Asp Pro Phe Phe Leu Ile Glu Thr Leu Cys Ile Ile
        275                 280                 285

Trp Phe Thr Phe Glu Leu Thr Val Arg Phe Leu Ala Cys Pro Asn Lys
290                 295                 300

Leu Asn Phe Cys Arg Asp Val Met Asn Val Ile Asp Ile Ile Ala Ile
305                 310                 315                 320

Ile Pro Tyr Phe Ile Thr Leu Ala Thr Val Val Ala Glu Glu Glu Asp
                325                 330                 335

Thr Leu Asn Leu Pro Lys Ala Pro Val Ser Pro Gln Asp Lys Ser Ser
            340                 345                 350

Asn Gln Ala Met Ser Leu Ala Ile Leu Arg Val Ile Arg Leu Val Arg
        355                 360                 365

Val Phe Arg Ile Phe Lys Leu Ser Arg His Ser Lys Gly Leu Gln Ile
370                 375                 380

Leu Gly Arg Thr Leu Lys Ala Ser Met Arg Glu Leu Gly Leu Leu Ile
385                 390                 395                 400

Phe Phe Leu Phe Ile Gly Val Val Leu Phe Ser Ala Val Tyr Phe
                405                 410                 415

Ala Glu Ala Gly Ser Glu Asn Ser Phe Phe Lys Ser Ile Pro Asp Ala
            420                 425                 430

Phe Trp Trp Ala Val Val Thr Met Thr Thr Val Gly Tyr Gly Asp Met
        435                 440                 445

Thr Pro Val Gly Val Trp Gly Lys Ile Val Gly Ser Leu Cys Ala Ile
        450                 455                 460

Ala Gly Val Leu Thr Ile Ala Leu Pro Val Pro Val Ile Val Ser Asn
465                 470                 475                 480

Phe Asn Tyr Phe Tyr His Arg Glu Thr Asp Gln Glu Glu Met Gln Ser
                485                 490                 495

Gln Asn Phe Asn His Val Thr Ser Cys Pro Tyr Leu Pro Gly Thr Leu
            500                 505                 510

Gly Gln His Met Lys Lys Ser Ser Leu Ser Glu Ser Ser Ser Asp Met
        515                 520                 525

Met Asp Leu Asp Asp Gly Val Glu Ser Thr Pro Gly Leu Thr Glu Thr
530                 535                 540

His Pro Gly Arg Ser Ala Val Ala Pro Phe Leu Gly Ala Gln Gln Gln
545                 550                 555                 560

Gln Gln Gln Gln Pro Val Ala Ser Ser Leu Ser Met Ser Ile Asp Lys
                565                 570                 575

Gln Leu Gln His Pro Leu Gln His Val Thr Gln Thr Gln Leu Tyr Gln
            580                 585                 590

Gln Gln Gln Gln Gln Gln Gln Gln Asn Gly Phe Lys Gln Gln
        595                 600                 605

Gln Gln Gln Thr Gln Gln Leu Gln Gln Gln Ser His Thr Ile
        610                 615                 620

Asn Ala Ser Ala Ala Ala Thr Ser Gly Ser Gly Ser Gly Leu
625                 630                 635                 640
```

Thr Met Arg His Asn Asn Ala Leu Ala Val Ser Ile Glu Thr Asp Val
                645                 650                 655

<210> SEQ ID NO 5
<211> LENGTH: 857
<212> TYPE: PRT
<213> ORGANISM: Rattus norvegicus

<400> SEQUENCE: 5

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
        35                  40                  45

Leu Asp Arg Leu Pro Arg Thr Arg Leu Gly Lys Leu Arg Asp Cys Asn
    50                  55                  60

Thr His Asp Ser Leu Leu Gln Val Cys Asp Asp Tyr Ser Leu Glu Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
            100                 105                 110

Leu Ser Phe Ser Gln Glu Leu Asp Tyr Trp Gly Ile Asp Glu Ile Tyr
        115                 120                 125

Leu Glu Ser Cys Cys Gln Ala Arg Tyr His Gln Lys Lys Glu Gln Met
    130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Ala Lys Ile Leu Ala
            180                 185                 190

Ile Ile Ser Ile Met Phe Ile Val Leu Ser Thr Ile Ala Leu Ser Leu
        195                 200                 205

Asn Thr Leu Pro Glu Leu Gln Ser Leu Asp Glu Phe Gly Gln Ser Thr
    210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
            260                 265                 270

Tyr Tyr Val Thr Ile Phe Leu Thr Glu Ser Asn Lys Ser Val Leu Gln
        275                 280                 285

Phe Gln Asn Val Arg Arg Val Val Gln Ile Phe Arg Ile Met Arg Ile
    290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

Phe Leu Ala Met Gly Ile Met Ile Phe Ser Ser Leu Val Phe Phe Ala
            340                 345                 350

Glu Lys Asp Glu Asp Asp Thr Lys Phe Lys Ser Ile Pro Ala Ser Phe
        355                 360                 365

```
Trp Trp Ala Thr Ile Thr Met Thr Thr Val Gly Tyr Gly Asp Ile Tyr
    370                 375                 380
Pro Lys Thr Leu Leu Gly Lys Ile Val Gly Gly Leu Cys Cys Ile Ala
385                 390                 395                 400
Gly Val Leu Val Ile Ala Leu Pro Ile Pro Ile Ile Val Asn Asn Phe
                405                 410                 415
Ser Glu Phe Tyr Lys Glu Gln Lys Arg Gln Glu Lys Ala Ile Lys Arg
            420                 425                 430
Arg Glu Ala Leu Glu Arg Ala Lys Arg Asn Gly Ser Ile Val Ser Met
        435                 440                 445
Asn Met Lys Asp Ala Phe Ala Arg Ser Ile Glu Met Met Asp Ile Val
    450                 455                 460
Val Glu Lys Asn Gly Glu Ser Ile Ala Lys Lys Asp Lys Val Gln Asp
465                 470                 475                 480
Asn His Leu Ser Pro Asn Lys Trp Lys Trp Thr Lys Arg Ala Leu Ser
                485                 490                 495
Glu Thr Ser Ser Ser Lys Ser Phe Glu Thr Lys Glu Gln Gly Ser Pro
            500                 505                 510
Glu Lys Ala Arg Ser Ser Ser Pro Gln His Leu Asn Val Gln Gln
        515                 520                 525
Leu Glu Asp Met Tyr Ser Lys Met Ala Lys Thr Gln Ser Gln Pro Ile
    530                 535                 540
Leu Asn Thr Lys Glu Met Ala Pro Gln Ser Lys Pro Pro Glu Glu Leu
545                 550                 555                 560
Glu Met Ser Ser Met Pro Ser Pro Val Ala Pro Leu Pro Ala Arg Thr
                565                 570                 575
Glu Gly Val Ile Asp Met Arg Ser Met Ser Ser Ile Asp Ser Phe Ile
            580                 585                 590
Ser Cys Ala Thr Asp Phe Pro Glu Ala Thr Arg Phe Ser His Ser Pro
        595                 600                 605
Leu Ala Ser Leu Ser Ser Lys Ala Gly Ser Ser Thr Ala Pro Glu Val
    610                 615                 620
Gly Trp Arg Gly Ala Leu Gly Ala Ser Gly Gly Arg Leu Thr Glu Thr
625                 630                 635                 640
Asn Pro Ile Pro Glu Thr Ser Arg Ser Gly Phe Phe Val Glu Ser Pro
                645                 650                 655
Arg Ser Ser Met Lys Thr Asn Asn Pro Leu Lys Leu Arg Ala Leu Lys
            660                 665                 670
Val Asn Phe Val Glu Gly Asp Pro Thr Pro Leu Leu Pro Ser Leu Gly
        675                 680                 685
Leu Tyr His Asp Pro Leu Arg Asn Arg Gly Gly Ala Ala Ala Ala Val
    690                 695                 700
Ala Gly Leu Glu Cys Ala Ser Leu Leu Asp Lys Pro Val Leu Ser Pro
705                 710                 715                 720
Glu Ser Ser Ile Tyr Thr Thr Ala Ser Ala Arg Thr Pro Pro Arg Ser
                725                 730                 735
Pro Glu Lys His Thr Ala Ile Ala Phe Asn Phe Glu Ala Gly Val His
            740                 745                 750
His Tyr Ile Asp Thr Asp Thr Asp Asp Glu Gly Gln Leu Leu Tyr Ser
        755                 760                 765
Val Asp Ser Ser Pro Pro Lys Ser Leu His Gly Ser Thr Ser Pro Lys
    770                 775                 780
Phe Ser Thr Gly Ala Arg Thr Glu Lys Asn His Phe Glu Ser Ser Pro
```

```
                    785                 790                 795                 800
Leu Pro Thr Ser Pro Lys Phe Leu Arg Pro Asn Cys Val Tyr Ser Ser
                805                 810                 815

Glu Gly Leu Thr Gly Lys Gly Pro Gly Ala Gln Glu Lys Cys Lys Leu
            820                 825                 830

Glu Asn His Thr Pro Pro Asp Val His Met Leu Pro Gly Gly Gly Ala
        835                 840                 845

His Gly Ser Thr Arg Asp Gln Ser Ile
    850                 855

<210> SEQ ID NO 6
<211> LENGTH: 655
<212> TYPE: PRT
<213> ORGANISM: Homo sapiens

<400> SEQUENCE: 6

Met Ala Ala Gly Val Ala Ala Trp Leu Pro Phe Ala Arg Ala Ala Ala
1               5                   10                  15

Ile Gly Trp Met Pro Val Ala Asn Cys Pro Met Pro Leu Ala Pro Ala
            20                  25                  30

Asp Lys Asn Lys Arg Gln Asp Glu Leu Ile Val Leu Asn Val Ser Gly
        35                  40                  45

Arg Arg Phe Gln Thr Trp Arg Thr Thr Leu Glu Arg Tyr Pro Asp Thr
    50                  55                  60

Leu Leu Gly Ser Thr Glu Lys Glu Phe Phe Phe Asn Glu Asp Thr Lys
65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Pro Arg Tyr Glu Cys Ile Ser
            100                 105                 110

Ala Tyr Asp Asp Glu Leu Ala Phe Tyr Gly Ile Leu Pro Glu Ile Ile
        115                 120                 125

Gly Asp Cys Cys Tyr Glu Glu Tyr Lys Asp Arg Lys Arg Glu Asn Ala
    130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
        195                 200                 205

Thr Val Pro Gly Ser Lys Glu Leu Pro Cys Gly Glu Arg Tyr Ser Val
    210                 215                 220

Ala Phe Phe Cys Leu Asp Thr Ala Cys Val Met Ile Phe Thr Gly Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
            260                 265                 270

Gly Leu Val Met Thr Asn Asn Glu Asp Val Ser Gly Ala Phe Val Thr
        275                 280                 285

Leu Arg Val Phe Arg Val Phe Arg Ile Phe Lys Phe Ser Arg His Ser
    290                 295                 300

Gln Gly Leu Arg Ile Leu Gly Tyr Thr Leu Lys Ser Cys Ala Ser Glu
```

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |

Leu Gly Phe Leu Leu Phe Ser Leu Thr Met Ala Ile Ile Ile Phe Ala
                        325                        330                        335

Thr Val Met Phe Tyr Ala Glu Lys Gly Ser Ser Ala Ser Lys Phe Thr
            340                        345                        350

Ser Ile Pro Ala Ser Phe Trp Tyr Thr Ile Val Thr Met Thr Thr Leu
            355                        360                        365

Gly Tyr Gly Asp Met Val Leu Lys Thr Ile Ala Gly Lys Ile Phe Gly
        370                        375                        380

Ser Ile Cys Ser Leu Ser Gly Val Leu Val Ile Ala Leu Pro Val Pro
385                        390                        395                        400

Val Ile Val Ser Asn Phe Ser Arg Ile Tyr His Gln Asn Gln Arg Ala
                  405                        410                        415

Asp Lys Arg Arg Ala Gln Lys Lys Ala Arg Leu Ala Arg Ile Arg Val
            420                        425                        430

Ala Lys Thr Gly Ser Ser Asn Ala Tyr Leu His Ser Lys Arg Asn Gly
               435                        440                        445

Leu Leu Asn Glu Ala Leu Glu Leu Thr Gly Thr Pro Glu Glu Glu His
450                        455                        460

Met Gly Lys Thr Thr Ser Leu Ile Glu Ser Gln His His Leu Leu
465                        470                        475                        480

His Cys Leu Glu Lys Thr Thr Gly Leu Ser Tyr Leu Val Asp Asp Pro
               485                        490                        495

Leu Leu Ser Val Arg Thr Ser Thr Ile Lys Asn His Glu Phe Ile Asp
            500                        505                        510

Glu Gln Met Phe Glu Gln Asn Cys Met Glu Ser Ser Met Gln Asn Tyr
               515                        520                        525

Pro Ser Thr Arg Ser Pro Ser Leu Ser Ser His Pro Gly Leu Thr Thr
        530                        535                        540

Thr Cys Cys Ser Arg Arg Ser Lys Lys Thr Thr His Leu Pro Asn Ser
545                        550                        555                        560

Asn Leu Pro Ala Thr Arg Leu Arg Ser Met Gln Glu Leu Ser Thr Ile
               565                        570                        575

His Ile Gln Gly Ser Glu Gln Pro Ser Leu Thr Thr Ser Arg Ser Ser
            580                        585                        590

Leu Asn Leu Lys Ala Asp Asp Gly Leu Arg Pro Asn Cys Lys Thr Ser
               595                        600                        605

Gln Ile Thr Thr Ala Ile Ile Ser Ile Pro Thr Pro Pro Ala Leu Thr
            610                        615                        620

Pro Glu Gly Glu Ser Arg Pro Pro Pro Ala Ser Pro Gly Pro Asn Thr
625                        630                        635                        640

Asn Ile Pro Ser Ile Thr Ser Asn Val Val Lys Val Ser Val Leu
               645                        650                        655

```
<210> SEQ ID NO 7
<211> LENGTH: 6942
<212> TYPE: DNA
<213> ORGANISM: Rattus norvegicus

<400> SEQUENCE: 7
tctagagccc ccacatgct  cccccaccgg gtccccccgtt gcgtgaggac acctcctctg      60
aggggctccg ctcgcccctc ttcggacccc ccggggccccc ggctggccag aggatggacg     120
aggaggagga tggagcgggc gccgaggagt cgggacagcc ccgtagcttc acgcagctca     180
acgacctgtc cggggccggg ggccggcagg ggccgggggtc gacggaaaag gacccgggca     240
```

```
gcgcggactc cgaggcggag gggctgccgt acccggcgct agccccgtgt gttttcttct      300
acttgagcca ggacagccgc ccgcggagct ggtgtctccg cacggtctgt aacccgtggt      360
tcgagcgagt cagtatgctg gtcattcttc tcaactgtgt gactctgggt atgttcaggc      420
cgtgtgagga cattgcctgt gactcccagc gctgccggat cctgcaggcc ttcgatgact      480
tcatctttgc cttctttgct gtggaaatgg tggtgaagat ggtggccttg gcatctttg       540 ggaagaaatg ttacctggga gacacttgga accggcttga cttttttcatt gtcattgcag    600 ggatgctgga gtattcgctg gacctgcaga acgtcagctt ctccgcagtc aggacagtcc     660
gtgtgctgcg accgctcagg gccattaacc gggtgcccag catgcgcatt ctcgtcacat     720
tactgctgga caccttgcct atgctgggca acgtcctgct gctctgtttc ttcgtctttt     780
tcatctttgg catcgtgggc gtccagctgt gggcaggact gcttcgcaac cggtgcttcc     840
tccccgagaa cttcagcctc cccctgagcg tggacctgga gccttattac cagacagaga     900
atgaggacga gagccccttc atctgctctc agcctcggga gaatggcatg agatcctgca     960
ggagtgtgcc cacactgcgt ggggaaggcg gtggtggccc accctgcagt ctggactatg    1020
agacctataa cagttccagc aacaccacct gtgtcaactg gaaccagtac tataccaact    1080
gctctgcggg cgagcacaac cccttcaaag cgccatcaa ctttgacaac attggctatg     1140
cctggatcgc catcttccag gtcatcacac tggaggctg gtcgacatc atgtacttcg      1200 taatggacgc tcactccttc tacaacttca tctacttcat tcttctcatc atcgtgggct    1260
ccttcttcat gatcaacctg tgcctggtgg tgattgccac gcagttctcc gagaccaaac    1320
agcgggagag tcagctgatg cgggagcagc gtgtacgatt cctgtccaat gctagcaccc    1380
tggcaagctt ctctgagcca ggcagctgct atgaggagct actcaagtac ctggtgtaca    1440
tcctccgaaa agcagcccga aggctggccc aggtctctag gctataggc gtgcgggctg     1500 ggctgctcag cagcccagtg gcccgtagtg gcaggagcc ccagcccagt ggcagctgca     1560
ctcgctcaca ccgtcgtctg tctgtccacc acctggtcca ccaccatcac caccaccatc    1620
accactacca cctgggtaat gggacgctca gagttccccg ggccagccca gagatccagg    1680
acagggatgc caatgggtct cgccggctca tgctaccacc accctctaca cccactccct    1740 ctggggggccc tccgaggggt gcggagtctg tacacagctt ctaccatgct gactgccact   1800
tggagccagt ccgttgccag gcaccccctc ccagatgccc atcggaggca tctggtagga    1860
ctgtgggtag tgggaaggtg taccccactg tgcataccag ccctccacca gagatactga    1920
aggataaagc actagtggag gtggccccca gccctgggcc ccccacccctc accagcttca   1980 acatcccacc tgggcccttc agctccatgc acaagctcct ggagacacag agtacgggag    2040
cctgccatag ctcctgcaaa atctccagcc cttgctccaa ggcagacagt ggagcctgcg    2100
ggccggacag ttgtccctac tgtgcccgga caggagcagg agagccagag tccgctgacc    2160
atgtcatgcc tgactcagac agcgaggctg tgtatgagtt cacacaggac gctcagcaca    2220
gtgacctccg ggatcccac agccggcggc gacagcggag cctgggccca gatgcagagc     2280
ctagttctgt gctggctttc tggaggctga tctgtgacac attccggaag atcgtagata    2340
gcaaatactt tggccgggga atcatgatcg ccatcctggt caatacactc agcatgggca    2400
tcgagtacca cgagcagccc gaggagctca ccaacgccct ggaaatcagc aacatcgtct    2460
tcaccagcct cttcgccttg gagatgctgc tgaaactgct tgtctacggt ccctttggct    2520
acattaagaa tccctacaac atctttgatg gtgtcattgt ggtcatcagt gtgtgggaga    2580
ttgtgggcca gcagggaggt ggcctgtcgg tgctgcggac cttccgcctg atgcgggtgc    2640
```

```
tgaagctggt gcgcttcctg ccggccctgc agcgccagct cgtggtgctc atgaagacca    2700
tggacaacgt ggccaccttc tgcatgctcc tcatgctgtt catcttcatc ttcagcatcc    2760
tgggcatgca tctctttggt tgcaagttcg catctgaacg ggatggggac acgttgccag    2820
accggaagaa tttcgactcc ctgctctggg ccatcgtcac tgtctttcag attctgactc    2880
aggaagactg gaataaagtc ctctacaacg gcatggcctc cacatcgtct tgggctgctc    2940
tttacttcat cgccctcatg acttttggca actatgtgct ctttaacctg ctggtggcca    3000
ttcttgtgga aggattccag gcagagggag atgccaccaa gtctgagtca gagcctgatt    3060
tcttttcgcc cagtgtggat ggtgatgggg acagaaagaa gcgcttggcc ctggtggctt    3120
tgggagaaca cgcggaacta cgaaagagcc ttttgccacc cctcatcatc catacggctg    3180
cgacaccaat gtcacacccc aagagctcca gcacaggtgt gggggaagca ctgggctctg    3240
gctctcgacg taccagtagc agtgggtccg ctgagcctgg agctgccac catgagatga    3300 aatgtccgcc aagtgcccgc agctccccgc acagtccctg gagtgcggca agcagctgga    3360
ccagcaggcg ctccagcagg aacagcctgg gccgggcccc cagcctaaag cggaggagcc    3420
cgagcgggga gcggaggtcc ctgctgtctg gagagggcca ggagagtcag gatgaggagg    3480
aaagttcaga agaggaccgg gccagcccag caggcagtga ccatcgccac aggggttcct    3540
tggaacgtga ggccaagagt tcctttgacc tgcctgacac tctgcaggtg ccggggctgc    3600
accgcacagc cagcggccgg agctctgcct ctgagcacca agactgtaat ggcaagtcgg    3660
cttcagggcg tttggcccgc accctgagga ctgatgaccc ccaactggat ggggatgatg    3720
acaatgatga gggaaatctg agcaaagggg aacgcataca gcctgggtc agatcccggc    3780 ttcctgcctg ttgccgagag cgagattcct ggtcggccta tatctttcct cctcagtcaa    3840
ggtttcgtct cctgtgtcac cggatcatca cccacaagat gtttgaccat gtggtcctcg    3900
tcatcatctt cctcaactgt atcaccatcg ctatggagcg ccccaaaatt gacccccaca    3960
gcgctgagcg catcttcctg accctctcca actacatctt cacggcagtc tttctagctg    4020
aaatgacagt gaaggtggtg gcactgggct ggtgctttgg ggagcaggcc tacctgcgca    4080
gcagctggaa tgtgctggac ggcttgctgg tgctcatctc cgtcatcgac atcctggtct    4140
ccatggtctc cgacacggc accaagatcc ttggcatgct gagggtgctg cggctgctgc    4200
ggaccctgcg tccactcagg gtcatcagcc gggcccaggg actgaagctg gtggtagaga    4260
ctctgatgtc atccctcaaa cccattggca acattgtggt catttgctgt gccttcttca    4320 tcattttttgg aattctcggg gtgcagctct tcaaagggaa gttcttcgtg tgtcagggtg    4380
aggacaccag gaacatcact aacaaatccg actgcgctga ggccagctac cgatgggtcc    4440
ggcacaagta caactttgac aacctgggcc aggctctgat gtccctgttt gtgctggcct    4500
ccaaggatgg ttgggttgac atcatgtatg atgggctgga tgctgtgggt gtggatcagc    4560
agcccatcat gaaccacaac ccctggatgc tgctatactt catctccttc ctcctcatcg    4620
tggccttctt tgtcctgaac atgtttgtgg gcgtggtggt ggagaacttc cataagtgca    4680
gacagcacca ggaggaggag gaggcgaggc ggcgtgagga gaagcgacta cggaggctgg    4740
agaaaaagag aaggagtaag gagaagcaga tggccgaagc ccagtgcaag ccctactact    4800
ctgactactc gagattccgg ctccttgtcc accacctgtg taccagccac tacctggacc    4860
tcttcatcac tggtgtcatc gggctgaacg tggtcactat ggccatggaa cattaccagc    4920
agccccagat cctggacgag gctctgaaga tctgcaatta catctttacc gtcatctttg    4980
tctttgagtc agtttttcaaa cttgtggcct ttggcttccg ccgtttcttc caggacaggt    5040
```

```
ggaaccagct ggacctggct attgtgcttc tgtccatcat gggcatcaca ctggaggaga    5100
ttgaggtcaa tctgtcgctg cccatcaacc ccaccatcat ccgtatcatg agggtgctcc    5160
gcattgctcg agttctgaag ctgttgaaga tggctgtggg catgcgggca ctgctgcaca    5220
cggtgatgca ggccctgccc caggtgggga acctgggact tctcttcatg ttattgtttt    5280
tcatctttgc agctctgggc gtggagtctct tggagacct ggagtgtgat gagacacacc    5340
cttgtgaggg cttgggtcgg catgccacct ttaggaactt tggtatggcc tttctgaccc    5400
tcttccgagt ctccactggt gacaactgga atggtattat gaaggacacc ctccgggact    5460
gtgaccagga gtccacctgc tacaacactg tcatctcccc tatctacttt gtgtccttcg    5520
tgctgacggc ccagtttgtg ctggtcaacg tggtcatagc tgtgctgatg aagcacctgg    5580
aagaaagcaa caaagaggcc aaggaggagg ccgagctcga ggccgagctg gagctggaga    5640
tgaagacgct cagcccgcag ccccactccc cgctgggcag ccccttcctc tggcccgggg    5700
tggagggtgt caacagtact gacagcccta agctggggc tccacacacc actgcccaca    5760
ttggagcagc ctcgggcttc tcccttgagc accccacgat ggtacccac cccgaggagg    5820 tgccagtccc cctaggacca gacctgctga ctgtgaggaa gtctggtgtc agccggacgc    5880
actctctgcc caatgacagc tacatgtgcc gcaatgggag cactgctgag agatccctag    5940
gacacagggg ctggggctc cccaaagccc agtcaggctc catcttgtcc gttcactccc    6000
aaccagcaga caccagctgc atcctacagc ttcccaaaga tgtgcactat ctgctccagc    6060
ctcatggggc tccacctggg gcgccatcc ctaaactacc cccacctggc cgctccctc    6120 tggctcagag gcctctcagg cgccaggcag caataaggac tgactccctg gatgtgcagg    6180
gcctgggtag ccgggaagac ctgttgtcag aggtgagtgg gccctcctgc cctctgaccc    6240
ggtcctcatc cttctggggc gggtcgagca tccaggtgca gcagcgttcc ggcatccaga    6300
gcaaagtctc caagcacatc cgcctgccag ccccttgccc aggcctggaa cccagctggg    6360
ccaaggaccc tccagagacc agaagcagct tagagctgga cacggagctg agctggattt    6420
caggagacct ccttcccagc agccaggaag aaccctgtt cccacgggac ctgaagaagt    6480
gctacagtgt agagacccag agctgcaggc gcaggcctgg gttctggcta gatgaacagc    6540
ggagacactc cattgctgtc agctgtctgg acagcggctc ccaaccccgc ctatgtccaa    6600 gccctcaag cctcgggggc caacctcttg ggggtcctgg gagccggcct aagaaaaaac    6660
tcagcccacc cagtatctct atagaccccc cggagagcca gggctctcgg ccccatgca    6720 gtcctggtgt ctgcctcagg aggagggcgc cggccagtga ctctaaggat ccctcggtct    6780 ccagcccct tgacagcacg gctgcctcac cctccccaaa gaaagacacg ctgagtctct    6840
ctggtttgtc ttctgaccca acagacatgg accctgagt cctacccact ctcccccatc    6900 accttctcc accgggtgca gatcctacgt ccgcctcctg gg                        6942
```

<210> SEQ ID NO 8
<211> LENGTH: 6990
<212> TYPE: DNA
<213> ORGANISM: Homo sapiens

<400> SEQUENCE: 8

```
atggctgaga gcgcctcccc gccctcctca tctgcagcag cccagccgc tgagccagga     60 gtcaccacgg agcagcccgg acccggagc ccccatcct cccgccagg cctggaggag    120 cctctggatg gagctgatcc tcatgtccca caccagacc tggcgcctat tgccttcttc    180
tgcctgcgac agaccaccag ccccccggaac tggtgcatca agatggtgtg caacccgtgg    240
```

```
tttgaatgtg tcagcatgct ggtgatcctg ctgaactgcg tgacacttgg catgtaccag      300
ccgtgcgacg acatggactg cctgtccgac cgctgcaaga tcctgcaggt ctttgatgac      360
ttcatcttta tcttctttgc catggagatg gtgctcaaga tggtggccct ggggattttt      420
ggcaagaagt gctacctcgg ggacacatgg aaccgcctgg atttcttcat cgtcatggca      480
gggatggtcg agtactccct ggaccttcag aacatcaacc tgtcagccat ccgcaccgtg      540
cgcgtcctga ggcccctcaa agccatcaac cgcgtgccca gtatgcggat cctggtgaac      600
ctgctcctgg acacactgcc catgctgggg aatgtcctgc tgctctgctt ctttgtcttc      660
ttcatctttg gcatcatagg tgtgcagctc tgggcgggcc tgctgcgtaa ccgctgcttc      720
ctggaggaga acttcaccat acaaggggat gtggccttgc ccccatacta ccagccggag      780
gaggatgatg agatgccctt catctgctcc ctgtcgggcg acaatgggat aatgggctgc      840
catgagatcc ccccgctcaa ggagcagggc cgtgagtgct gcctgtccaa ggacgacgtc      900
tacgactttg gggcggggcg ccaggacctc aatgccagcg gcctctgtgt caactggaac      960
cgttactaca atgtgtgccg cacgggcagc gccaaccccc acaagggtgc catcaacttt     1020
gacaacatcg gttatgcttg gattgtcatc ttccaggtga tcactctgga aggctgggtg     1080
gagatcatgt actacgtgat ggatgctcac tccttctaca acttcatcta cttcatcctg     1140
cttatcatag tgggctcctt cttcatgatc aacctgtgcc tcgttgtcat agcgacccag     1200
ttctcggaga ccaagcaacg ggagcaccgg ctgatgctgg agcagcggca gcgctacctg     1260
tcctccagca cggtggccag ctacgccgag cctggcgact gctacgagga gatcttccag     1320
tatgtctgcc acatcctgcg caaggccaag cgccgcgccc tgggcctcta ccaggccctg     1380
cagagccggc gccaggccct gggcccggag gccccgcccc cgccaaaacc tgggccccac     1440
gccaaggagc cccggcacta ccatgggaag actaagggtc agggagatga agggagacat     1500
ctcggaagcc ggcattgcca gactttgcat gggcctgcct ccccctggaaa tgatcactcg     1560 ggaagagagc tgtgcccgca acatagcccc ctggatgcga cgccccacac cctggtgcag     1620
cccatccccg ccacgctggc ttccgatccc gccagctgcc cttgctgcca gcatgaggac     1680
ggccggcggc cctcgggcct gggcagcacc gactcgggcc aggagggctc gggctccggg     1740
agctccgctg gtggcgagga cgaggcggat ggggacgggg cccggagcag cgaggacgga     1800
gcctcctcag aactggggaa ggaggaggag gaggaggagc aggcggatgg ggcggtctgg     1860
ctgtgcgggg atgtgtggcg ggagacgcga gccaagctgc gcggcatcgt ggacagcaag     1920
tacttcaacc ggggcatcat gatggccatc ctggtcaaca ccgtcagcat gggcatcgag     1980
caccacgagc agccggagga gctgaccaac atcctggaga tctgcaatgt ggtcttcacc     2040
agcatgtttg ccctggagat gatcctgaag ctggctgcat ttgggctctt cgactacctg     2100
cgtaacccct acaacatctt cgacagcatc attgtcatca tcagcatctg ggagatcgtg     2160
gggcaggcgg acggtgggct gtcggtgctg cggaccttcc ggctgctgcg cgtgctgaaa     2220
ctggtgcgct tcatgcctgc cctgcggcgc cagctcgtgg tgctcatgaa gaccatggac     2280
aacgtggcca ccttctgcat gctgctcatg ctcttcatct tcatcttcag catccttggg     2340
atgcatattt ttggctgcaa gttcagcctc cgcacggaca ctggagacac ggtgcccgac     2400
aggaagaact tcgactccct gctgtgggcc atcgtcactg tgttccagat cctcacccag     2460
gaggactgga acgtcgttct ctacaatggc atggcctcca cttctccctg ggcctccctc     2520
tactttgtcg ccctcatgac cttcggcaac tatgtgctct tcaacctgct ggtggccatc     2580
ctggtggagg gcttccaggc ggagggtgac gccaatcgct cctactcgga cgaggaccag     2640
```

```
agctcatcca acatagaaga gtttgataag ctccaggaag gcctggacag cagcggagat    2700
cccaagctct gcccaatccc catgacccce aatgggcacc tggaccccag tctcccactg    2760
ggtgggcacc taggtcctgc tggggctgcg ggacctgccc cccgactctc actgcagccg    2820
gaccccatgc tggtggccct gggctcccga aagagcagtg tcatgtctct agggaggatg    2880
agctatgacc agcgctccct gtccagctcc cggagctcct actacgggcc atggggccgc    2940
agcgcggcct gggccagccg tcgctccagc tggaacagcc tcaagcacaa gccgccgtcg    3000
gcggagcatg agtccctgct ctctgcggag cgcggcggcg gcgcccgggt ctgcgaggtt    3060
gccgcggacg aggggccgcc gcgggccgca cccctgcaca ccccacacgc ccaccacatt    3120
catcacgggc cccatctggc gcaccgccac cgccaccacc gccggacgct gtccctcgac    3180
aacagggact cggtggacct ggccgagctg gtgcccgcgg tgggcgccca ccccgggcc     3240 gcctggaggg cggcaggccc ggcccccggg catgaggact gcaatggcag gatgcccagc    3300
atcgccaaag acgtcttcac caagatgggc gaccgcgggg atcgcgggga ggatgaggag    3360
gaaatcgact acaccctgtg cttccgcgtc cgcaagatga tcgacgtcta taagcccgac    3420
tggtgcgagg tccgcgaaga ctggtctgtc tacctcttct ctcccgagaa caggttccgg    3480
gtcctgtgtc agaccattat tgcccacaaa ctcttcgact acgtcgtcct ggccttcatc    3540
tttctcaact gcatcaccat cgccctggag cggcctcaga tcgaggccgg cagcaccgaa    3600
cgcatctttc tcaccgtgtc caactacatc ttcacggcca tcttcgtggg cgagatgaca    3660
ttgaaggtag tctcgctggg cctgtacttc ggcgagcagg cgtacctacg cagcagctgg    3720
aacgtgctgg atggctttct tgtcttcgtg tccatcatcg acatcgtggt gtccctggcc    3780
tcagccgggg gagccaagat cttggggggtc ctccagtctc tgcggctcct cgcacccta   3840 cgccccctgc gtgtcatcag ccgggcgccg ggcctgaagc tggtggtgga gacactcatc    3900
tcctccctca gcccatcgg caacatcgtg ctcatctgct gtgccttctt catcatcttt    3960
ggcatcctgg gagtgcagct cttcaagggc aagttctacc actgtctggg cgtggacacc    4020
cgcaacatca ccaaccgctc ggactgcatg gccgccaact accgctgggt ccatcacaaa    4080
tacaacttcg acaacctggg ccaggctctg atgtccctct ttgtcctggc atccaaggat    4140
ggttgggtga acatcatgta caatggactg gatgctgttg ctgtggacca gcagcctgtg    4200
accaaccaca accctggat gctgctgtac ttcatctcct tcctgctcat cgtcagcttc     4260
tttgtgctca acatgtttgt gggtgtcgtg gtggagaact tccacaagtg ccggcagcac    4320
caggaggctg aagaggcacg gcggcgtgag gagaagcggc tgcggcgcct ggagaagaag    4380
cgccggaagg cccagcggct gccctactat gccacctatt gtcacacccg gctgctcatc    4440
cactccatgt gcaccagcca ctacctggac atcttcatca ccttcatcat ctgcctcaac    4500
gtggtcacca tgtccctgga gcactacaat cagcccacgt ccctggagac agccctcaag    4560
tactgcaact atatgttcac cactgtcttt gtgctggagg ctgtgctgaa gctggtggca    4620
tttggtctga ggcgcttctt caaggaccga tggaaccagc tggacctggc cattgtgcta    4680
ctgtcagtca tgggcatcac cctggaggag atcgagatca atgcggccct gcccatcaat    4740
cccaccatca tccgcatcat gagggttctg cgcattgccc gagtgctgaa gctgttgaag    4800
atggccacag gaatgcgggc cctgctggac acggtggtgc aagcttttgcc ccaggtgggc    4860 aacctgggcc tcctcttcat gctgctcttc ttcatctatg ctgctctcgg ggtggagctc    4920
tttgggaagc tggtctgcaa cgacgagaac ccgtgcgagg gcatgagccg gcatgccacc    4980
ttcgagaact tcggcatggc cttcctcaca ctcttccagg tctccacggg tgacaactgg    5040
```

| | |
|---|---:|
| aacgggatca tgaaggacac gctgcgggac tgcacccacg acgagcgcag ctgcctgagc | 5100 |
| agcctgcagt ttgtgtcgcc gctgtacttc gtgagcttcg tgctcaccgc gcagttcgtg | 5160 |
| ctcatcaacg tggtggtggc tgtgctcatg aagcacctgg acgacagcaa caaggaggcg | 5220 |
| caggaggacg ccgagatgga tgccgagctc gagctggaga tggcccatgg cctgggccct | 5280 |
| ggcccgaggc tgcctaccgg ctccccgggc cccctggcc gagggccggg aggggcgggc | 5340 |
| ggcgggggcg acaccgaggg cggcttgtgc cggcgctgct actcgcctgc ccaggagaac | 5400 |
| ctgtggctgg acagcgtctc tttaatcatc aaggactcct tggaggggga gctgaccatc | 5460 |
| atcgacaacc tgtcgggctc catcttccac cactactcct cgcctgccgg ctgcaagaag | 5520 |
| tgtcaccacg acaagcaaga ggtgcagctg gctgagacgg aggccttctc cctgaactca | 5580 |
| gacaggtcct cgtccatcct gctgggtgac gacctgagtc tcgaggaccc cacagcctgc | 5640 |
| ccacctggcc gcaaagacag caagggtgag ctggacccac ctgagcccat gcgtgtggga | 5700 |
| gacctgggcg aatgcttctt ccccttgtcc tctacggccg tctcgccgga tccagagaac | 5760 |
| ttcctgtgtg agatggagga gatcccattc aaccctgtcc ggtcctggct gaaacatgac | 5820 |
| agcagtcaag cacccccaag tcccttctcc ccggatgcct ccagccctct cctgcccatg | 5880 |
| ccagccgagt tcttccaccc tgcagtgtct gccagccaga aaggcccaga aaagggcact | 5940 |
| ggcactggaa ccctccccaa gattgcgctg cagggctcct gggcatctct gcggtcacca | 6000 |
| agggtcaact gtaccctcct ccggcaggcc accgggagcg acacgtcgct ggacgccagc | 6060 |
| cccagcagct ccgcgggcag cctgcagacc acgctcgagg acagcctgac cctgagcgac | 6120 |
| agccccggc gtgccctggg gccgcccgcg cctgctccag accccgggc cggcctgtcc | 6180 |
| cccgccgctc gccgccgcct gagcctgcgc ggccggggcc tcttcagcct gcgggggctg | 6240 |
| cgggcgcatc agcgcagcca cagcagcggg ggctccacca gcccgggctg cacccaccac | 6300 |
| gactccatgg acccctcgga cgaggagggc gcggtggcg cgggcggcgg gggcgcgggc | 6360 |
| agcgagcact cggagaccct cagcagcctc tcgctcacct ccctcttctg cccgccgccc | 6420 |
| ccgccgccag cccccggcct cacgcccgcc aggaagttca gcagcaccag cagcctggcc | 6480 |
| gccccggcc gcccccacgc cgccgccctg gcccacggcc tggcccggag cccctcgtgg | 6540 |
| gccgcggacc gcagcaagga cccccccggc cgggcaccgc tgcccatggg cctgggcccc | 6600 |
| ttggcgcccc cgccgcaacc gctccccgga gagctggagc cgggagacgc cgccagcaag | 6660 |
| aggaagagat gagggtcgca ggggcccccg gccgcccacc gccgccccg tctcaccttc | 6720 |
| tttacctcag gagccaggag cagacagcaa tacttcgtcc acacctggga tcgcgcaggg | 6780 |
| cccgcagggc acaggcgccc gacagccggg ctgagcggag tctgggttag ccaggcctgc | 6840 |
| gtggcccatg gtggcccttc cagtgcatat acatacatat atatatatat atgcatatat | 6900 |
| atatatatat atatatatat gtgtatacac acacacatag acagacatat atatatatat | 6960 |
| ttatttttt tactgagagc ttatgacttc | 6990 |

<210> SEQ ID NO 9
<211> LENGTH: 9014
<212> TYPE: DNA
<213> ORGANISM: Mus musculus

<400> SEQUENCE: 9

| | |
|---|---:|
| gtgtgttgca catgtctgtg tgagtacagg cacacatgtg catgcaagtg gttgcagaag | 60 |
| gcagaagatc actttggatc ccttgggggct ggagttatag gtgcttgtga gccaccagac | 120 |
| atggtacttg taattgagaa gcaagtggtc ccaaccacag tgccatctct ccagctccca | 180 |

```
cttctttct ttttgaccac aactctcccc tttataaaag aggaagaaag ttattcccaa    240 gccgggaaa cactcacaac aggctccttc ttttaactta gtggagaagt cggggcagcc    300
tcaaaaacag tgagtaggtc acaactctag tactctacta agcacttgag caaattacaa    360
gatagcaatt ggtatgcagg agccaaagta tgatgagggt tggatgagca tgtgctaagc    420
acagccatcc tcttttgtct taattggagc agatatactg caagcctctc tctgtctaga    480
gataacgttt attttatttg gatgcatgag tattttgctt acatgtatgt atgggtacta    540
tgtgtgtgcc tggagcctgc agtggtcacg agagggatc agatcccatg gaacggagct     600
cggcgcggcg cggcccggag cggcggcggc agtggcggcg gcggcgacgc ttcccgcggg    660
ctcgccctca ggtgttcgcg gctgccgtcg ccgaagatcg cgggtcgggg cctcgcggcg    720
atcgccctgg gcgggccgga gacgcctcgg gccccctggc ggctcggggt ccacccggcg    780
ccgcgggccc gccgctttcc ctcgcctcgc ctttgcgcct cttctcgctc tgcctctcca    840
tttattattc ttatcatttt tatttcaaa tggtgtagcc gccagaggtg cggtgctaaa     900
ttcttggaag gggcccggat gtactgagga tgcattacaa tctcacgaaa ggaggcggta    960
gtggaaagca gcagttttg gtgtttggtg caataatggg gatcaggtaa tcacccgaag    1020
ggagcaagaa ccactgcgga tccacggctt cctggatttg cgcgagagcc gccggcctcg   1080
gaggagggat ccatcccgag ccgctcgcgg ctgttgctgc atttcttcct ctttgtggct   1140
tctcctttcc aagcagtttt tggccaatgg tcaatgaaaa cacgaggatg tacgttccag   1200
aggaaaacca ccaaggttcc aactatggga gcccacgccc agctcatgcc aacatgaatg   1260
ccaatgcagc tgcaggactt gctcccgagc acatccctac tccaggggca gcactgtcct   1320
ggcaggcagc catcgatgcc gcccggcagg ccaagctcat gggcagtgct ggcaacgcaa   1380
ccatctctac cgtcagttcc acacagcgga agcggcagca gtatgggaaa cccaagaagc   1440
aggggggcac aaccgccaca cggccgcccc gggctctgct gtgtctgacc ctgaagaacc   1500
ctatccggag ggcgtgcata agcattgttg aatggaaacc atttgaaatc attattttac   1560
tgactatttt tgccaattgt gtggccttag caatctatat tcccttttccg gaagacgact  1620 ccaacgccac caactccaac ctggaacgag tggagtatct cttcctcatc attttttaccg  1680 tggaagcatt tttaaaagta attgcctacg gacttctctt ccaccccaac gcttacctcc   1740
gcaatggttg gaatttactg gattttataa tcgtggttgt agggcttttt agtgcaattt   1800
tagaacaagc aaccaaagct gatggggcca atgctctagg agggaaagga gctggattcg   1860
acgtgaaggc actgagagcg ttccgcgtgc tccgtccact gcggctagtg tccggagtcc   1920
caagtctcca ggtggtcctg aactccatca tcaaggccat ggtgcctctg ctgcacattg   1980
cccttcttgt gctcttcgtc atcatcattt atgctattat cggcctggag ctcttcatgg   2040
gaaagatgca caagacctgc tacaaccagg agggcataat agatgttccg gcagaagagg   2100
atccttcccc ttgtgctttg gagacaggcc atgggcgaca gtgtcagaac gggaccgtgt   2160
gcaaacccgg gtgggatggg cccaagcacg gcatcaccaa cttcgacaac ttcgccttcg   2220
ccatgctgac ggtgttccag tgtatcacca tggagggctg gacagacgtg ctgtactgga   2280
tgcaagacgc tatgggctat gagttgccct gggtgtattt tgtcagtctg gtcatctttg   2340
gatccttttt cgttctaaat ctggttctcg gtgttttgag cggggagttt ccaaagaga    2400 gggagaaagc caaagcccga ggagatttcc agaagcttcg agagaagcag caactagaag   2460
aagatctcaa aggctacctg gactggatca cccaggcaga agacattgac cccgagaatg   2520
aggacgaggg catggatgaa gacaagcctc gaaacatgag catgcccaca agtgagactg   2580
```

```
agtctgtcaa cactgaaaac gtggctggag gtgacatcga gggagaaaac tgtggagcca    2640
ggcttgccca tcggatctcc aaatccaaat tcagccgcta ctggcgcagg tggaatcgat    2700
tctgcagaag aaaatgccgt gcagcagtta agtccaacgt cttctactgg ctcgtgatct    2760
tcctggtgtt cctcaacacc ctcaccattg cctccgaaca ttacaaccag cctcactggc    2820
tcacagaagt gcaagacaca gccaataaag ccctcctggc ccttttcact gcagaaatgc    2880
tcctgaagat gtacagcctg ggtcttcagg cctattttgt gtccctcttc aaccgctttg    2940
actgtttcat tgtgtgtggg ggcatcctgg agaccatcct ggtggagacg aagatcatgt    3000
ctcccctggg catctctgtg ctgagatgtg tgcggttgct caggatcttc aagatcacca    3060
ggtactggaa ttccttgagc aaccttgtgg catccttgct gaactcagtg cgctccattg    3120
cctccctgct gctgctcctc ttcctcttca tcatcatctt ctccctcctg gggatgcagc    3180
tctttggagg gaagttcaat ttcgatgaga tgcagacccg taggagcacg ttcgataact    3240
tcccgcagtc tctcctcact gtgtttcaga tcctgaccgg ggaggactgg aattcggtga    3300
tgtatgatgg gatcatggct tatggcggcc cctcttttcc agggatgtta gtctgtattt    3360
acttcatcat cctcttcatc tgtggaaatt atatcctact gaatgtgttc ttggccattg    3420
cggtggacaa cctggctgat gcggagagcc tgacctcagc ccaaaaggag gaggaagaag    3480
agaaggagag gaagaagctg gccaggactg ccagcccaga aaagaaacag gaggtgatgg    3540
agaagccagc cgtggaggag agcaaagagg agaaaattga actgaaatcc attacagccg    3600
atggagaatc cccacccact accaagatca acatggatga cctccagccc agtgaaaacg    3660
aggataagag tccccactcc aacccagaca ctgcagggga agaggatgaa gaggagccag    3720
agatgcctgt ggggccacgc ccccggcccc tgtctgagct gcaccttaag gaaaaggcag    3780
ttcccatgcc ggaagccagt gcattttttca tcttcagccc aaacaacagg ttccgcctgc    3840
agtgccaccg tattgtcaat gacacgatct tcaccaacct catcctcttc ttcattctgc    3900
tcagcagcat ctctctggct gctgaggacc ccgtccagca cacctccttc aggaaccata    3960
tcctaggcaa tgcagactat gtcttcacta gtatctttac attagaaatt atccttaaga    4020
tgactgctta cggggctttc ctgcacaagg gctctttctg ccgaaactac ttcaatatcc    4080
tggacctgct ggtggttagc gtgtccctca tctcctttgg catccagtcc agcgcgatca    4140
acgttgtgaa gattttacga gtgctgcgag tcctcagacc cctgagggcc atcaacaggg    4200
ccaaggggct aaagcatgtg gttcagtgcg tgtttgtggc catccggacc atcgggaaca    4260
tcgtaattgt caccactctg ctgcagttca tgttcgcctg cattggggtc cagctcttca    4320
agggaaagct ctatacctgt tcggatagtt ctaaacagac ggaggcagaa tgcaagggta    4380
actatatcac atacaaagat ggagaggtcg atcaccccat tatccagcct cgaagctggg    4440
agaacagcaa gtttgacttt gacaatgttt tggcagccat gatggctctc ttcaccgtct    4500
ccaccttcga agggtggcca gagctgctgt accgctccat tgactccac acagaagaca    4560
agggccccat ctacaactac cgtgtggaga tctccatctt cttcatcatc tatatcatca    4620
tcattgcctt cttcatgatg aacatcttcg tgggtttcgt cattgtcacc ttccaggagc    4680
agggggaaca agagtacaag aactgtgagc tggacaagaa ccagagacaa tgtgtggaat    4740
atgccctcaa ggcccgaccc ttgcgaaggt acatccccaa gaaccagcac cagtacaaag    4800
tgtggtacgt ggtcaactct acctacttcg agtatctgat gttcgttctc atcctgctca    4860
acaccatctg cctggccatg cagcactatg gccagagctg cctcttcaaa atcgccatga    4920
atatactcaa catgctttc accggcctct tcacagtgga gatgatcctg aagctcattg    4980
```

```
ccttcaaacc caagggttac tttagtgatc cctggaatgt ttttgacttc ctcatcgtca   5040
ttgggagcat aattgatgtc attctcagtg agactaatcc agctgaacat acccaatgct   5100
ctccctctat gagtgcagag gagaactccc gcatctccat caccttcttc cgcctcttcc   5160
gggtcatgcg cctggtgaag ctgctgagcc gcggggaagg catccgaacc ctgctgtgga   5220
ccttcatcaa gtccttccag gctctgccct atgtggctct tttgattgtg atgctgttct   5280
ttatctatgc agtgattggg atgcaggtgt ttgggaagat tgccctgaat gacaccacag   5340
agatcaatcg gaacaacaac ttccagacgt tcccccaggc tgtgttactg ctgttcaggt   5400
gtgccaccgg agaggcctgg caggacatca tgctggcctg catgccaggc aagaagtgtg   5460
ccccagagtc tgagcccagc aacagcacgg aaggggagac ccctgtggc agcagctttg    5520 ctgtcttcta cttcatcagc ttctacatgc tctgtgcctt cctgatcatc aacctctttg   5580
tagctgttat catggacaac tttgactacc tgactaggga ttggtctatc ctcggtcccc   5640
atcacctgga tgaattcaag agaatctggg ccgagtatga ccctgaagcc aagggtcgga   5700
tcaaacactt ggatgtggtg accctcctcc gtcgaattca gccccactg ggttttggga    5760 aattgtgtcc tcaccgtgtg gcctgcaaac gcctggtgtc catgaacatg cctctgaaca   5820
gcgatggcac agtcatgttc aatgctaccc tgtttgccct cgtcaggaca gccctgagga   5880
tcaaaacaga agggaaccta gagcaagcca atgaggagct cgggccatc atcaagaaaa    5940 tctggaagag gactagcatg aagctgttgg accaggtggt gccccctgca ggcgatgacg   6000
aggtcacagt gggcaagttc tatgccacct tcctgatcca agagtacttc aggaaattca   6060
agaagcgaaa agagcagggg ctggtgggca agccctcaca aaggaatgca ctgtccctcc   6120
aggctggctt gcgcaccttg catgacattg ggcctgagat ccggcgggcc atctctgggg   6180
atctgactgc tgaggaggag ttggacaagg ctatgaagga ggcggtgtct gctgcctccg   6240
aagatgacat cttcaggagg ctggaggcc tgttcgcaa ccatgtcacc tactatcaga    6300
gtgacagcag gggcaacttt cctcagacgt tcgccaccca gcgcccactg cacatcaaca   6360
agacagggaa caaccaagct gacactgagt caccgtccca tgagaagctg gtggactcca   6420
cgttcacccc cagcagctac tcatccacgg gctccaatgc caacatcaac aatgccaaca   6480
acactgccct gggccgcttc ccccatcccg ctggctactc cagcacggtc agcactgtgg   6540
agggccatgg gcctcccttg tccctgctg tccgagtaca ggaggcagca tggaagctca    6600
gctctaagag gtgccactcc cgagagagcc agggagccac ggtgaatcag gagatatttc   6660
cagatgagac ccgcagcgta aggatgagtg aagaagccga gtactgcagt gagcccagcc   6720
tgctctccac agatatgttc tcctaccagg aagatgaaca ccgacaactg acctgcccag   6780
aggaggacaa gagggagatc cagccatctc caaagaggag tttccttcgc tctgcctctc   6840
taggtcgaag ggcctccttc catctggaat gtctaaagcg acaaaaggat caaggggag    6900 acatctctca gaagacagcc ttgcccttgc atctggttca tcatcaggca ttggcagtgg   6960
caggcttgag ccccctcctg cagagaagcc attctcctac cacattcccc aggccgtgcc   7020 ccacacccc tgtcactcca ggcagccggg gcagacccct acggcccatc cctaccctac    7080
ggctggaggg ggcagagtcc agcgagaaac tcaacagcag cttcccatcc atccactgca   7140
gctcctggtc tgaggacacg acagcctgta gtggagcag cagcatggcc cggagagccc    7200
ggcccgtctc cctcaccgtg cccagccagg ctggagctcc agggagacag ttccatggca   7260
gtgccagcag cctggtggaa gcggtcttga tttcagaagg actgggacag tttgctcaag   7320
atcccaagtt catcgaggtc accacccagg agctggctga cgcctgcgac atgacaatag   7380
```

```
aggagatgga gaacgccgca gacaacatcc tcagtgggggg cgcccagcag agccccaacg    7440
gcaccctctt accttttgtg aactgcaggg acccggggca ggacagggct gtggcccag     7500 aggacgagag ctgcgcatat gccctggggc gaggccggag cgaggaggcg ctcgcggaca    7560
gcaggtccta cgtcagcaac ctgtagtcct cagggctggc gagacgcggg tggttttttt    7620
attcgtttca atgttcctaa tgggttcgtt tcagaagtgc ctcactgttc tcgtgacctg    7680
gaggtaaccg gaacagcgtc ttcattcact gctgtcggga taagcctcag agctgggcgg    7740
tgtacggagt cggcttttca ggggagaagg ccaaggccgt ggtgcggggg ctccagcacc    7800
ttccgcggca gcaccgccca aggacccca cccccacccc tgagcaaaag ggtgttttcc     7860
ccttgcttgt ataaacagtc atttgcacat gttctgtctg agcctggccg tctctatgga    7920
gcagggcccc agggatctat ggcaggaatg ggccagcgcc cccagtagga gccgggaggt    7980
ggctgcgagg ttcccagcag tgcaggtctg gtccctatgg tcccttcagg gactcttttcc   8040 ctgcaaggag ctgagatgca ggtggcagga gccagtgcag atcacaccac ccgccctcag    8100
ctagccaggc cagggggggcg caggctgctg cctggtgctc ggggtttcat ggtttgaggg    8160
ttcttgtcag catgttgcga ctttctgggg tttggttttct ttattactat ttgttgtgtt   8220
ttcccacggg gaggggagga ataagagcgg ttacaactgc gcggcctcac ttcactgttt    8280
ccacatttgc atttgcgtat ttaagtcgga tttggtttga ttgtattctt taaatggtgc    8340
ggtccacccc caccgccacc cccaccccc  actggagcaa gggttcaata tcaccagaga    8400
aaggttttac ctgctctgtg tctgcccagt aacttgttcc aatttcctta agtaaaagca    8460
acttttttct ttctttcgag tttggttgag catcacaatc agcaggctaa caggcagtta    8520
gatcaggcgg tgtgcgcctg ggcgattgag ctgggctcct ttctgtgctg gcatatggaa    8580
ctggttcaag agagaagaaa tatgggcatc tttgtgtcac acttgtgtcc atagtatgtg    8640
cgtatgtgca cccacgtggt atgtgtgcgc cccaccccac ccctgcacaa agcctgtag     8700 aaccccgttt gggtttgact gcagggagtt ctaaatctgg ggctatttga aagcaagaac    8760
aaaccactgt ctctgcttct gcttctgaaa cgagaatcgg taactgcatt tttctgtccc    8820
acgagatatg caaaagcaat gcaataatat ccatttttaaa atatggttgt gagttgtgtc    8880
agcattaaaa ttctattta aaaaaaaaac cacgaaattt aagggaaaaa ctcaagaaga     8940
cattttgctt cgatatattc tgtgtaatgt tttattgcat tgataatgtt tctgttgaag    9000
aaactgttat actt                                                     9014
```

<210> SEQ ID NO 10
<211> LENGTH: 7648
<212> TYPE: DNA
<213> ORGANISM: Homo sapiens

<400> SEQUENCE: 10

```
atggacgagg aggaggatgg agcgggcgcc gaggagtcgg gacagccccg gagcttcatg     60
cggctcaacg acctgtcggg ggccggggc cggccggggc cggggtcagc agaaaaggac     120
ccgggcagcg cggactccga ggcggagggg ctgccgtacc cggcgctggc cccggtggtt    180
ttcttctact tgagccagga cagccgcccg cggagctggt gtctccgcac ggtctgtaac    240
ccctggtttg agcgcatcag catgttggtc atccttctca actgcgtgac cctgggcatg    300
ttccggccat gcgaggacat cgcctgtgac tcccagcgct gccggatcct gcaggccttt    360
gatgacttca tctttgcctt ctttgccgtg gagatggtgg tgaagatggt ggccttgggc    420
atctttggga aaaagtgtta cctgggagac acttggaacc ggcttgactt tttcatcgtc    480
```

```
atcgcaggga tgctggagta ctcgctggac ctgcagaacg tcagcttctc agctgtcagg    540
acagtccgtg tgctgcgacc gctcagggcc attaaccggg tgcccagcat gcgcatcctt    600
gtcacgttgc tgctggatac gctgcccatg ctgggcaacg tcctgctgct ctgcttcttc    660
gtcttcttca tcttcggcat cgtcggcgtc cagctgtggg cagggctgct tcggaaccga    720
tgcttcctac ctgagaattt cagcctcccc ctgagcgtgg acctggagcg ctattaccag    780
acagagaacg aggatgagag ccccttcatc tgctcccagc cacgcgagaa cggcatgcgg    840
tcctgcagaa gcgtgcccac gctgcgcggg gacgggggcg gtggcccacc ttgcggtctg    900
gactatgagg cctacaacag ctccagcaac accacctgtg tcaactggaa ccagtactac    960
accaactgct cagcggggga gcacaacccc ttcaagggcg ccatcaactt tgacaacatt   1020
ggctatgcct ggatcgccat cttccaggtc atcacgctgg agggctgggt cgacatcatg   1080
tactttgtga tggatgctca ttccttctac aatttcatct acttcatcct cctcatcatc   1140
gtgggctcct tcttcatgat caacctgtgc ctggtggtga ttgccacgca gttctcagag   1200
accaagcagc gggaaagcca gctgatgcgg gagcagcgtg tgcggttcct gtccaacgcc   1260
agcacctgg ctagcttctc tgagcccggc agctgctatg aggagctgct caagtacctg   1320
gtgtacatcc ttcgtaaggc agcccgcagg ctggctcagg tctctcgggc agcaggtgtg   1380
cgggttgggc tgctcagcag cccagcaccc ctcgggggcc aggagaccca gcccagcagc   1440
agctgctctc gctcccaccg ccgcctatcc gtccaccacc tggtgcacca ccaccaccac   1500
catcaccacc actaccacct gggcaatggg acgctcaggg cccccgggc cagcccggag   1560
atccaggaca gggatgccaa tgggtcccgc aggctcatgc tgccaccacc ctcgacgcct   1620
gccctctccg ggcccccccc tggtggcgca gagtctgtgc acagcttcta ccatgccgac   1680
tgccacttag agccagtccg ctgccaggcg ccccctccca ggtccccatc tgaggcatcc   1740
ggcaggactg tgggcagcgg gaaggtgtat cccaccgtgc acaccagccc tccaccggag   1800
acgctgaagg agaaggcact agtagaggtg gctgccagct ctgggccccc aaccctcacc   1860
agcctcaaca tcccaccccg gccctacagc tccatgcaca agctgctgga cacacagagt   1920
acaggtgcct gccaaagctc ttgcaagatc tccagccctt gcttgaaagc agacagtgga   1980
gcctgtggtc cagacagctg cccctactgt gcccgggccg gggcagggga ggtggagctc   2040
gccgaccgtg aaatgcctga ctcagacagc gaggcagttt atgagttcac acaggatgcc   2100
cagcacagcg acctccggga cccccacagc cggcggcaac ggagcctggg cccagatgca   2160
gagcccagct ctgtgctggc cttctggagg ctaatctgtg acaccttccg aaagattgtg   2220
gacagcaagt actttggccg gggaatcatg atcgccatcc tggtcaacac actcagcatg   2280
ggcatcgaat accacgagca gcccgaggag cttaccaacg ccctagaaat cagcaacatc   2340
gtcttcacca gcctctttgc cctggagatg ctgctgaagc tgcttgtgta tggtccctt   2400
ggctacatca agaatcccta caacatcttc gatggtgtca ttgtggtcat cagcgtgtgg   2460
gagatcgtgg gccagcaggg gggcggcctg tcggtgctgc ggaccttccg cctgatgcgt   2520
gtgctgaagc tggtgcgctt cctgcgcgcg ctgcagcggc agctggtggt gctcatgaag   2580
accatggaca cgtggccac cttctgcatg ctgcttatgc tcttcatctt catcttcagc   2640
atcctgggca tgcatctctt cggctgcaag tttgcctctg agcgggatgg ggacaccctg   2700
ccagaccgga gaattttga ctccttgctc tgggccatcg tcactgtctt tcagatcctg   2760
acccaggagg actggaacaa agtcctctac aatggtatgg cctccacgtc gtcctgggcg   2820
gccctttatt tcattgccct catgaccttc ggcaactacg tgctcttcaa tttgctggtc   2880
```

```
gccattctgg tggagggctt ccaggcggag gaaatcagca acgggaaga tgcgagtgga    2940 cagttaagct gtattcagct gcctgtcgac tcccaggggg gagatgccaa caagtccgaa    3000
tcagagcccg atttcttctc acccagcctg gatggtgatg gggacaggaa gaagtgcttg    3060
gccttggtgt ccctgggaga gcacccggag ctgcggaaga gcctgctgcc gcctctcatc    3120
atccacacgg ccgccacacc catgtcgctg cccaagagca ccagcacggg cctgggcgag    3180
gcgctgggcc ctgcgtcgcg ccgcaccagc agcagcgggt cggcagagcc tggggcggcc    3240
cacgagatga agtcaccgcc cagcgcccgc agctctccgc acagccctg gagcgctgca    3300 agcagctgga ccagcaggcg ctccagccgg aacagcctcg gccgtgcacc cagcctgaag    3360
cggagaagcc caagtggaga gcggcggtcc ctgttgtcgg gagaaggcca ggagagccag    3420
gatgaagagg agagctcaga agaggagcgg gccagccctg cgggcagtga ccatcgccac    3480 aggggggtccc tggagcggga ggccaagagt tcctttgacc tgccagacac actgcaggtg    3540
ccagggctgc atcgcactgc cagtggccga gggtctgctt ctgagcacca ggactgcaat    3600
ggcaagtcgg cttcagggcg cctggcccgg gccctgcggc ctgatgaccc cccactggat    3660
ggggatgacg ccgatgacga gggcaacctg agcaaagggg aacgggtccg cgcgtggatc    3720
cgagcccgac tccctgcctg ctgcctcgag cgagactcct ggtcagccta catcttccct    3780
cctcagtcca ggttccgcct cctgtgtcac cggatcatca cccacaagat gttcgaccac    3840
gtggtccttg tcatcatctt ccttaactgc atcaccatcg ccatggagcg ccccaaaatt    3900
gaccccacac gcgctgaacg catcttcctg accctctcca attacatctt caccgcagtc    3960
tttctggctg aaatgacagt gaaggtggtg gcactgggct ggtgcttcgg ggagcaggcg    4020
tacctgcgga gcagttggaa cgtgctggac gggctgttgg tgctcatctc cgtcatcgac    4080
attctggtgt ccatggtctc tgacagcggc accaagatcc tgggcatgct gagggtgctg    4140
cggctgctgc ggaccctgcg cccgctcagg gtgatcagcc gggcgcaggg gctgaagctg    4200
gtggtggaga cgctgatgtc ctcactgaaa cccatcggca acattgtagt catctgctgt    4260
gccttcttca tcattttcgg catcttgggg gtgcagctct tcaaagggaa gttttttcgtg    4320 tgccagggcg aggataccag gaacatcacc aataaatcgg actgtgccga ggccagttac    4380
cggtgggtcc ggcacaagta caactttgac aaccttggcc aggccctgat gtccctgttc    4440
gttttggcct ccaaggatgg ttgggtggac atcatgtacg atgggctgga tgctgtgggc    4500
gtggaccagc agcccatcat gaaccacaac ccctggatgc tgctgtactt catctcgttc    4560
ctgctcattg tggccttctt tgtcctgaac atgtttgtgg gtgtggtggt ggagaacttc    4620
cacaagtgtc ggcagcacca ggaggaagag gaggcccgc ggcggagga gaagcgccta    4680 cgaagactgg agaaaaagag aaggaatcta atgctggacg atgtaattgc ttccggcagc    4740
tcagccagcg ctgcgtcaga agcccagtgc aaaccttact actccgacta ctcccgcttc    4800
cggctcctcg tccaccactt gtgcaccagc cactacctgg acctcttcat cacaggtgtc    4860
atcgggctga acgtggtcac catggccatg agcactacc agcagcccca gattctggat    4920
gaggctctga agatctgcaa ctacatcttc actgtcatct ttgtcttgga gtcagttttc    4980
aaacttgtgg cctttggttt ccgtcggttc ttccaggaca ggtggaacca gctggacctg    5040
gccattgtgc tgctgtccat catgggcatc acgctggagg aaatcgaggt caacgcctcg    5100
ctgcccatca accccaccat catccgcatc atgagggtgc tgcgcattgc ccgagtgctg    5160
aagctgctga gatggctgt gggcatgcgg gcgctgctgg acacggtgat gcaggccctg    5220
ccccaggtgg ggaacctggg acttctcttc atgttgttgt ttttcatctt tgcagctctg    5280
```

```
ggcgtggagc tctttggaga cctggagtgt gacgagacac accctgtga gggcctgggc    5340
cgtcatgcca cctttcggaa ctttggcatg gccttcctaa ccctcttccg agtctccaca    5400
ggtgacaatt ggaatggcat tatgaaggac accctccggg actgtgacca ggagtccacc    5460
tgctacaaca cggtcatctc gcctatctac tttgtgtcct tcgtgctgac ggcccagttc    5520
gtgctagtca acgtggtgat cgccgtgctg atgaagcacc tggaggagag caacaaggag    5580
gccaaggagg aggccgagct agaggctgag ctggagctgg agatgaagac cctcagcccc    5640
cagccccact cgccactggg cagccccttc ctctggcctg ggtcgaggg ccccgacagc     5700
cccgacagcc ccaagcctgg ggctctgcac ccagcggccc acgcgagatc agcctcccac    5760
ttttccctgg agcaccccac ggacaggcag ctgtttgaca ccatatccct gctgatccag    5820
ggctccctgg agtgggagct gaagctgatg acgagctgg caggcccagg gggccagccc     5880
tctgccttcc cttctgcccc cagcctggga ggctccgacc cacagatccc tctagctgag    5940
atggaggctc tgtctctgac gtcagagatt gtgtctgaac cgtcctgctc tctagctctg    6000
acggatgact ctttgcctga tgacatgcac acactcttac ttagtgccct ggagagcaat    6060
atgcagcccc accccacgga gctgccagga ccagacttac tgactgtgcg gaagtctggg    6120
gtcagccgaa cgcactctct gcccaatgac agctacatgt gtcggcatgg gagcactgcc    6180
gaggggcccc tgggacacag gggctggggg ctccccaaag ctcagtcagg ctccgtcttg    6240
tccgttcact cccagccagc agataccagc tacatcctgc agcttcccaa agatgcacct    6300
catctgctcc agcccacag cgccccaacc tggggcacca tccccaaact gccccccacca     6360
ggacgctccc ctttggctca gaggccactc aggcgccagg cagcaataag gactgactcc    6420
ttggacgttc agggtctggg cagccgggaa gacctgctgg cagaggtgag tgggcctcc     6480
ccgcccctgg cccgggccta ctctttctgg ggccagtcaa gtacccaggc acagcagcac    6540
tcccgcagcc acagcaagat ctccaagcac atgaccccgc cagcccctg cccaggccca     6600
gaacccaact ggggcaaggg ccctccagag accagaagca gcttagagtt ggacacggag    6660
ctgagctgga tttcaggaga cctcctgccc cctggcggcc aggaggagcc cccatcccca    6720
cgggacctga agaagtgcta cagcgtggag gcccagagct gccagcgccg gcctacgtcc    6780
tggctggatg agcagaggag acactctatc gccgtcagct gcctggacag cggctcccaa    6840
ccccacctgg gcacagaccc ctctaacctt gggggccagc ctcttggggg gctgggagc     6900
cggcccaaga aaaaactcag cccgcctagt atcaccatag accccccga gagccaaggt     6960
cctcggaccc cgcccagccc tggtatctgc ctccggagga gggctccgtc cagcgactcc    7020
aaggatccct tggcctctgg cccccctgac agcatggctg cctcgccctc cccaaagaaa    7080
gatgtgctga gtctctccgg tttatcctct gacccagcag acctggaccc ctgagtcctg    7140
ccccactttc ccactcacct ttctccactg ggtgccaagt cctagctcct cctcctgggc    7200
tatattcctg acaaaagttc catatagaca ccaaggaggc ggaggcgctc ctccctgcct    7260
cagtggctct gggtacctgc aagcagaact tccaaagaga gttaaaagca gcagccccgg    7320
caactctggc tccaggcaga aggagaggcc cggtgcagct gaggttcccg acaccagaag    7380
ctgttgggag aaagcaatac gtttgtgcag aatctctatg tatattctat tttattaaat    7440
taattgaatc tagtatatgc gggatgtacg acattttgtg actgaagaga cttgtttcct    7500
tctactttta tgtgtctcag aatattttg aggcgaaggc gtctgtctct tggctatttt     7560
aacctaaaat aacagtctag ttatattccc tcttcttgca agcacaagc tgggaccgcg     7620
agcacattgc agccccaacg gtggccca                                       7648
```

<210> SEQ ID NO 11
<211> LENGTH: 6073
<212> TYPE: DNA
<213> ORGANISM: Caenorhabditis elegans

<400> SEQUENCE: 11

| | | | | | |
|---|---|---|---|---|---|
| accactttga | cccggtcacc | tgaaaatgct | acgtcagcca | gttccggaac | tgcgcagttt | 60 |
| tcagtccctc | tctaaatatg | caggcggacc | gagatcagtt | ctcggtagga | gaacatcagc | 120 |
| aatcacagtc | aatcgaagac | aatcacaatc | gacacgacga | catgaggatg | ttgaggcact | 180 |
| gggctcgatc | gaaggctcga | agaaaactct | gcagctgtcg | gaacacggac | gattggcctc | 240 |
| ctcctcggag | gcctcccctt | ctcggtggga | gggccgacag | atcgagtggg | ggaatgaaga | 300 |
| gcaaattgaa | gaggaaagtg | aacttccgta | tccggggttt | gctgagccag | cacttcgatg | 360 |
| tttttatcaa | gccagacctc | caaggaaatg | ggcgcttcaa | atggtgatga | gtccttggtt | 420 |
| tgaccgaata | acaatggctg | tgattatgat | taattgtgta | accctcggga | tgtacaggcc | 480 |
| ttgtgaagat | ggtccagact | gtgacactta | ccggtgtcaa | atccttgata | taattgacaa | 540 |
| ttgcatattt | gtctattttg | catttgaaat | ggtgataaaa | ataatggctc | tagggtttta | 600 |
| cggtcctgcg | gcttatatgt | ctgatacatg | gaatcgtctg | gacttttca | ttgttatggc | 660 |
| aggaatcgct | gagtttgtat | tacacgagta | tctcggagga | aacatcaatt | taacagcaat | 720 |
| cagaacggtt | cgagtactga | ggccgcttcg | agcggtcaat | cgaataccat | cgatgaggat | 780 |
| tttagtcaat | tgttactcg | acacattacc | catgcttgga | aatgtgcttc | ttttatgttt | 840 |
| tttcgttttc | ttcatttttg | gaattgttgg | tgttcaatta | tgggcgggtt | tattacgaaa | 900 |
| tcgatgtgtc | attaatttac | caaaaacaat | atcggagaat | caatctgcgt | tgttcaacaa | 960 |
| tgtaaaactg | acaaggtttt | acattccgga | agacacatcg | ctagaatata | tttgcagtca | 1020 |
| accagacgca | aacgggttac | acacttgctc | aaatcttcca | ccatacactg | tcgacggagt | 1080 |
| gaagtgtaac | cttacactag | atgaatacga | caaagtaacg | aacgactctt | gtatcaactg | 1140 |
| gaatatttat | tacaacgaat | gtcaggtgat | gcaacgaaat | ccatttcaag | gatcagtttc | 1200 |
| tttcgacaat | atcggttttg | cgtgggtcgc | tattttctc | gtcatatcac | ttgaagggtg | 1260 |
| gacggatata | atgtactatg | tacaggacgc | tcattctttt | tggaattgga | tctattttgt | 1320 |
| tcttctcatt | gtgatcggtg | cttttttcat | gatcaatcta | tgccttgttg | ttattgctac | 1380 |
| tcagtttgct | gaaacaaagc | ggcgggagac | tgaacgaatg | ctacaagaac | gaaaaatgct | 1440 |
| actaaataga | gattctatat | cgtgtactgg | aagtgagatt | ggtggcgctt | cttccaaaga | 1500 |
| agaaggagat | actgtttatg | cagcttttgt | tagatttatc | ggacacacct | ttcggagaac | 1560 |
| aaaacgagca | gcgaaaaaaa | agtacactgc | ctacatggaa | gaaagagcag | agcgaaaaag | 1620 |
| ttccgaacga | caacaacgga | ggaagtcaaa | acttgatgat | atggccacac | tttcaaggat | 1680 |
| cgaggaaaaa | gctgaagacg | aagaagatga | aaccaccata | actcgtgaaa | acggagatga | 1740 |
| tcaaatcgag | caaaatggtg | atggagtccg | gataaagcgc | gtaaaaattg | aagaagaacc | 1800 |
| caagatcaaa | ataggaaacg | gtaattcgaa | tggaccgcat | tacaaacact | ccagcagcga | 1860 |
| tgaagaatct | gatgaggatg | gcgaagagga | ccaagtttac | gatggggaag | aagccaagaa | 1920 |
| gaagagtaca | ccttccaagc | tctggtggtt | tcgagaaaaa | attcagaaat | tcgttatttg | 1980 |
| tgatcacttc | actagaggga | ttcttgttgc | aattttggtg | aatacgttga | gcatgggtgt | 2040 |
| ggagtaccat | caacaaccgg | aaatattaac | tgtcattctg | gaatattcga | atttattttt | 2100 |
| cactgctttg | tttgctttgg | aaatgcttct | taagatcatt | gcaagtggat | tgtttggtta | 2160 |

```
tttagctgat ggattcaacc ttttcgacgg aggaattgtc gcattgagtg ttcttgagtt    2220
atttcaagaa ggtaaaggag gtctatcagt tcttcgtact tttcgccttc ttcgaattct    2280
gaaattggtt cgcttcatgc ctgctcttcg atatcaactg gttgtgatgc tccgaacaat    2340
ggacaatgtc actgtgtttt ttggactttt ggttcttttc atctttatct tcagcattct    2400
cggaatgaat ctgtttgggt gcaaattttg caaagtcgaa gagaaatttc ttggaggcct    2460
tgcgaaaaag tgtgaaagaa aaactttga cacgttgctc tgggcgctga tcactgtgtt    2520
tcagattctt acacaagaag attggaacat ggttttattc aacggtatgg ctcaaacaaa    2580
cccatgggca gctctttact ttgtggcgct catgacattt ggtaattacg ttcttttcaa    2640
cttacttgta gctatcttgg tagaaggatt ccaagaaagc aaggaagaag aaaagcgaca    2700
attggaagag gatgcgagaa agcaagctgt agaagaagaa gacgaaagaa agcgagaatt    2760
ggagcttata attgccaaaa caacgtcacc tgctttcaat aatggagtag cacctgcaga    2820
atgtacttgt caaagaccat cctccccgga agaatcacca tctccgagat tgctgtctgc    2880
aaattaccac ccatctcctg aaaggaaaca ctctgcaaat ttggatgcca tcattgataa    2940
aagattagtt ctaagaaatt cggcaccttt cgatagatca ccagtatctg aaggacgtga    3000
tgattctaga ctcaatcgtc acgccagtct tgtacttcct gtcgctaatg gagttccgta    3060
tcggcgacaa agagttcaca gttggagtgg gctttgtcat catttcaatc cgaactgccc    3120
tgtacatgga agaagagcac tcattgaaac ttatgcacga gaaaaatttc tagaagctag    3180
tcaagagcta aaacaggctc tcgctgagga agaaaaaaga aatgaagcca agcaaaacac    3240
gtttgtgaga aaacttttga aaaaaacgtg ccttcacaac cgaactgaat tttcactatt    3300
tcttatgggc ccaaaaaacc cgctacgcat aaaatgccta caaacaactc aaaagaaatg    3360
gttcgattac accgtattgt ttttcattgg aatcaactgt ataacactgg ctatggaacg    3420
accatcaatt cctcctgata gttttgaaag gcaatttctt catatttctg ggtacatttt    3480
cacagtgatt tttactggtg aaatgatgat gaaggttatt gcaaatggtt gtttcattgg    3540
gcaagcagcg tattttaaag atggttggaa cattctcgat ggaattcttg ttgtcatttc    3600
cttaatcaac attgcgtttg aacttctggc aactggcgat tctccaaaaa tatttggtgt    3660
tataagagtg ttaaggctac ttcgtgcatt gaggccttta cgagttatca ataggcctcc    3720
gggagttaag cttgtagtaa tgacattaat atccagtctg aaacctatcg gaaacattgt    3780
tctgatttgc tgcacattct tcattatctt tggcatcctc ggtgttcagt tgttcaaagg    3840
tatgatgtac cattgcattg gacctgaagt tggaaacgtt acaacaaaag cggattgcat    3900
tgaagattac cgaaacaaat gggttaatca tcgttacaac tttgacaacc tcggtcaggc    3960
tcttatgtca ctttttcgttc tttcaagtaa agatggatgg gtctcgatca tgtatcaagg    4020
aatcgacgct gtaggggttg acgtgcaacc aattgagaat tacaatgaat ggagaatgat    4080
ttactttatt tcattcttat tgcttgttgg attctttgtg ctgaacatgt tcgtaggagt    4140
tgtggttgag aactttcata agtgcaaaga agcattggaa aaagaaatga gagaaaaaga    4200
gaaagaaaag aggctgaaga gaaagctgaa acggcagaag tttgaggaga gtatggctgg    4260
aaaacgaaaa aaaatggaaa ggaattatcc ttattaccat gattatggtc atacaaggct    4320
tttcttgcac ggaattgtca cctccaaata cttcgaccta gcgatcgccg cagtaattgg    4380
tatcaatgtc atatctatgg ctatggagtt ctatatgatg ccaatgggac tgaaatacgt    4440
tctcaaagct ctcaattact tttttcacagc agtcttcaca ctagaagctg ctatgaagct    4500
gattgctttg ggttttaaac gtttctttat tgaaaaatgg aatcgcttgg atatgttcat    4560
```

```
tgttattttg tctattgcgg gcataatttt cgaagagttt gaagctctcg aacttccaat      4620
taatccaaca atcattcgtg tcatgcgagt gctccggata gccagagttc tgaaactgct      4680
gaaaatggcc aaaggaattc gatcattgtt ggacacagtg ggagaagcgt tgccccaggt      4740
tggaaatctc gggtctctgt tcttccttct tttcttcata tttgctgcac ttggtgttga      4800
actgtttgga aaactggagt gctctgaaga tcatccgtgt gatggattag agaacatgc       4860 gcattttaaa aattttggaa tggcttttt aacactcttt cgaatagcga cgggtgataa       4920
ttggaatgga attatgaagg atgccctccg tgatgactgt gattcctccg atcactgtga      4980
aacaaactgc tgcgttgatc caatcctggc accatgcttc ttcgtaattt tcgtcttgat      5040
ctcacaattt gtacttgtca atgtagtagt cgctgtactt atgaaacatc tggaagaaag      5100
taacaagcga gatgcggaag gaccggcaga accaacaggt gaaaacatcg agaacgagat      5160
cacaaagtcc gacgatgacg aaattgtgga agaacacgaa ccactcgcaa ttgaacatgt      5220
taaagagggt gaacttgatg aagaagaaga gacagaagaa ggtcccacca ctcaaatacc      5280
agacgggcat ggtggtatta acggttatc catgcaggtt ctggaacaag aattaatcga       5340
agtcgagaga catttggaag aaagatatcg gagggcaagc gagtgtctcg gcggagaact      5400
tcagcctttg aatcccggag agatcgaaga tctagacgat cccgagttca gaccacggag      5460
tagatcacat agaccacgag caagaacaaa cagtgcgttg agcaataaaa gccgtggatc      5520
acacaagtct gctttatagc ctattcactt atcaagaaga aaatatcatc aactttttt       5580 gcaattttc atagttgtat atccacccca cttttatgg aaccatctca tatttagaat        5640
tctttgcttt gccaaaacct tggttgatc aatatcagat tgttcgttta ttactggtaa       5700
catttgtcat aactcaaaaa atccctcttt tttcaatttc cctctgaacc tttttatcg       5760 catgtatgaa acttgtatga aagaatttga aacaaataaa acgaaaccta tgcttttttc      5820
aattgtcaac ttatatttcc ggtccatgtt tcctctactt ttcgcttctg catttcattt      5880
gccttcctgt tagaaattaa atctacttga aaaagaactg catcttccaa agtgttcact      5940
tcaaactgat ctttttctgat gtttaatatt gttcgaaatt ctaatatcaa ctattttctt     6000
ggtttattgc ttttttgtct tttgtctttt ttgtcttctt cctttcattc attattgaaa     6060
aaatgaataa ttg                                                        6073

<210> SEQ ID NO 12
<211> LENGTH: 5905
<212> TYPE: DNA
<213> ORGANISM: Rattus norvegicus

<400> SEQUENCE: 12
tctggagcca tacggtgccc tgatcctctg taccaggaag acagggtgaa gatggaggag        60
aggtactacc cggtgatctt cccggacgag cggaatttcc gccccttcac ttccgactct      120
ctggctgcca tagagaagcg gattgctatc caaaaggaga ggaagaagtc caaagacaag      180
gcggcagctg agccccagcc tcggcctcag cttgacctaa aggcctccag gaagttacct      240
aagctttatg gtgacattcc ccctgagctt gtagcgaagc tctggaagaa cctggaccca      300
ttctacaaag accataagac attcatggtg ttgaacaaga gagaacaat ttatcgcttc       360 agcgccaagc gggccttgtt cattctgggg ccttttaatc ccctcagaag cttaatgatt      420
cgtatctctg tccattcagt ctttagcatg ttcatcatct gcacggtgat catcaactgt      480
atgttcatgg cgaattctat ggagagaagt ttcgacaacg acattcccga atacgtcttc      540
attgggattt atatttaga agctgtgatt aaaatattgg caagaggctt cattgtggat      600
```

```
gagttttcct tcctccgaga tccgtggaac tggctggact tcattgtcat tggaacagcg    660
atcgcaactt gttttccggg cagccaagtc aatctttcag ctcttcgtac cttccgagtg    720
ttcagagctc tgaaggcgat ttcagttatc tcaggtctga aggtcatcgt aggtgccctg    780
ctgcgctcgg tgaagaagct ggtagacgtg atggtcctca ctctcttctg cctcagcatc    840
tttgccctgg tcggtcagca gctgttcatg ggaattctga accagaagtg tattaagcac    900
aactgtggcc ccaaccctgc atccaacaag gattgctttg aaaaggaaaa agatagcgaa    960
gacttcataa tgtgtggtac ctggctcggc agcagaccct gtcccaatgg ttctacgtgc   1020
gataaaacca cattgaaccc agacaataat tatacaaagt ttgacaactt tggctggtcc   1080
tttctcgcca tgttccgggt tatgactcaa gactcctggg agaggcttta ccgacagatc   1140
ctgcggacct ctgggatcta ctttgtcttc ttcttcgtgg tggtcatctt cctgggctcc   1200
ttctacctgc ttaacctaac cctggctgtt gtcaccatgg cttatgaaga acagaacaga   1260
aatgtagctg ctgagacaga ggccaaggag aaaatgtttc aggaagccca gcagctgtta   1320
agggaggaga aggaggctct ggttgccatg ggaattgaca aagttccct taattccctt   1380 caagcttcat ccttttcccc gaagaagagg aagtttttcg gtagtaagac aagaaagtcc   1440
ttctttatga gagggtccaa gacggcccaa gcctcagcgt ctgattcaga ggacgatgcc   1500
tctaaaaatc cacagctcct tgagcagacc aaacgactgt cccagaactt gccagtggat   1560
ctctttgatg agcacgtgga ccccctccac aggcagagag cgctgagcgc tgtcagtatc   1620
ttaaccatca ccatgcagga acaagaaaaa ttccaggagc cttgtttccc atgtgggaaa   1680
aatttggcct ctaagtacct ggtgtgggac tgtagccctc agtggctgtg cataaagaag   1740
gtcctgcgga ccatcatgac ggatcccttt actgagctgg ccatcaccat ctgcatcatc   1800
atcaataccg ttttcttagc cgtggagcac cacaacatgg atgacaactt aaagaccata   1860
ctgaaaatag gaaactgggt tttcacggga attttcatag cggaaatgtg tctcaagatc   1920
atcgcgctcg acccttacca ctacttccgg cacggctgga atgttttga cagcatcgtg   1980 gccctcctga gtctcgctga tgtgctctac aacacactgt ctgataacaa taggtctttc   2040
ttggcttccc tcagagtgct gagggtcttc aagttagcca atcctggcc cacgttaaac   2100 actctcatta agatcatcgg ccactccgtg ggcgcgcttg gaaacctgac tgtggtcctg   2160
actatcgtgg tcttcatctt ttctgtggtg ggcatgcggc tcttcggcac caagtttaac   2220
aagaccgcct acgccaccca ggagcggccc aggcggcgct ggcacatgga taatttctac   2280
cactccttcc tggtggtgtt ccgcatcctc tgtgggaat ggatcgagaa catgtggggc   2340
tgcatgcagg atatgacgg ctccccgttg tgcatcattg tctttgtcct gataatggtg   2400
atcgggaagc ttgtggtgct taacctcttc attgccttgc tgctcaattc cttcagcaat   2460
gaggagaagg atgggagcct ggaaggagag accaggaaaa ccaaagtgca gctagccctg   2520
gatcggttcc gccgggcctt ctccttcatg ctgcacgctc ttcagagttt tgttgcaag   2580 aaatgcagga ggaaaaactc gccaaagcca aagagacaa cagaaagctt tgctggtgag   2640
aataaagact caatcctccc ggatgcgagg ccctggaagg agtatgatac agacatggct   2700
ttgtacactg acaggccgg ggctccgctg gccccactcg cagaggtaga ggacgatgtg   2760
gaatattgtg gtgaaggcgg tgccctaccc acctcacaac atagtgctgg agttcaggcc   2820
ggtgacctcc ctccagagac caagcagctc actagcccgg atgaccaagg ggttgaaatg   2880
gaagtatttt ctgaagaaga tctgcattta agcatacaga gtcctcgaaa gaagtctgac   2940
gcagtgagca tgctctcgga atgcagcaca attgacctga atgatatctt tagaaatttta   3000
```

```
cagaaaacag tttcccccaa aaagcagcca gatagatgct ttcccaaggg ccttagttgt   3060
cactttctat gccacaaaac agacaagaga aagtccccct gggtcctgtg gtggaacatt   3120
cggaaaacct gctaccaaat cgtgaagcac agctggtttg agagtttcat aatctttgtt   3180
attctgctga gcagtggagc gctgatattt gaagatgtca atctcccag ccggccccaa    3240 gttgagaaat tactaaggtg taccgataat attttcacat ttattttcct cctggaaatg   3300
atcctgaagt gggtggcctt tggattccgg aggtatttca ccagtgcctg gtgctggctt   3360
gatttcctca ttgtggtggt gtctgtgctc agtctcatga atctaccaag cttgaagtcc   3420
ttccggactc tgcgggccct gagacctctg cgggcgctgt cccagtttga aggaatgaag   3480
gttgtcgtct acgccctgat cagcgccata cctgccattc tcaatgtctt gctggtctgc   3540 ctcatttct ggctcgtatt ttgtatcttg ggagtaaatt tattttctgg gaagtttgga    3600
aggtgcatta acgggacaga cataaatatg tatttggatt ttaccgaagt tccgaaccga   3660
agccaatgta acattagtaa ttactcgtgg aaggtcccgc aggtcaactt tgacaacgtg   3720
gggaatgcct atctcgccct gctgcaagtg gcaacctata agggctggct ggaaatcatg   3780
aatgctgctg tcgattccag agagaaagac gagcagccgg acttgaggc gaacctctac    3840 gcgtatctct actttgtggt ttttatcatc ttcggctcct tctttaccct gaacctcttt   3900
atcggtgtta ttattgacaa cttcaatcag cagcagaaaa agttaggtgg ccaagacatt   3960
tttatgacag aagaacagaa gaaatattac aatgcaatga aaaagttagg aaccaagaaa   4020
cctcaaaagc ccatcccaag gcccctgaac aaatgtcaag cctttgtgtt cgacctggtc   4080
acaagccagg tctttgacgt catcattctg ggtcttattg tcttaaatat gattatcatg   4140
atggctgaat ctgccgacca gcccaaagat gtgaagaaaa cctttgatat cctcaacata   4200
gccttcgtgg tcatctttac catagagtgt ctcatcaaag tctttgcttt gaggcaacac   4260
tacttcacca atggctggaa cttatttgat tgtgtggtcg tggttctttc tatcattagt   4320
accctggttt cccgcttgga ggacagtgac atttctttcc cgcccacgct cttcagagtc   4380
gtccgcttgg ctcggattgg tcgaatcctc aggctggtcc gggctgcccg gggaatcagg   4440
accctcctct ttgctttgat gatgtctctc ccctctctct tcaacatcgg tctgctgctc   4500
ttcctggtga tgttcattta cgccatcttt gggatgagct ggttttccaa agtgaagaag   4560
ggctccggga tcgacgacat cttcaacttc gagacctta cgggcagcat gctgtgcctc    4620
ttccagataa ccacttcggc tggctgggat accctcctca ccccatgct ggaggcaaaa    4680 gaacactgca actcctcctc ccaagacagc tgtcagcagc cgcagatagc cgtcgtctac   4740
ttcgtcagtt acatcatcat ctccttcctc atcgtggtca acatgtacat cgctgtgatc   4800
ctcgagaact tcaacacagc cacggaggag agcgaggacc ctctgggaga ggacgacttt   4860
gaaatcttct atgaggtctg ggagaagttt gaccccgagg cgtcgcagtt catccagtat   4920
tcggccctct ctgactttgc ggacgccctg ccggagccgt tgcgtgtggc caagccgaat   4980
aagtttcagt ttctagtgat ggacttgccc atggtgatgg cgaccgcct ccattgcatg    5040 gatgttctct ttgctttcac taccaggtc ctcgggact ccagcggctt ggataccatg      5100
aaaaccatga tggaggagaa gtttatggag gccaaccctt ttaagaagct ctacgagccc   5160
atagtcacca ccaccaagag gaaggaggag gagcaaggcg ccgccgtcat ccagagggcc   5220
taccggaaac acatggagaa gatggtcaaa ctgaggctga aggacaggtc aagttcatcg   5280
caccaggtgt tttgcaatgg agacttgtcc agcttggatg tggccaaggt caaggttcac   5340
aatgactgaa ccctcatctc caccctacc tcactgcctc acagcttagc ctccagcctc     5400
```

| | | |
|---|---|---|
| tggcgagcag gcggcagact cactgaacac aggccgttcg atctgtgttt ttggctgaac | 5460 | |
| gaggtgacag gttggcgtcc attttaaat gactcttgga aagatttcat gtagagagat | 5520 | |
| gttagaaggg actgcaaagg acaccgacca taacggaagg cctggaggac agtccaactt | 5580 | |
| acataaagat gagaaacaag aaggaaagat cccaggaaaa cttcagattg tgttctcagt | 5640 | |
| acattcccca atgtgtctgt tcggtgtttt gagtatgtga cctgccacat gtagctcttt | 5700 | |
| tttgcatgta cgtcaaaacc ctgcagtaag ttaatagctt gctacgggtg ttcctaccag | 5760 | |
| catcacagaa ttgggtgtat gactcaaacc taaaagcatg actctgactt gtcagtcagc | 5820 | |
| accccgactt tcagacgctc caatctctgt cccaggtgtc taacgaataa ataggtaaaa | 5880 | |
| gaaaaaaaaa aaaaaaaaaa aaaaa | 5905 | |

<210> SEQ ID NO 13
<211> LENGTH: 8131
<212> TYPE: DNA
<213> ORGANISM: Homo sapiens
<220> FEATURE:
<221> NAME/KEY: misc_feature
<222> LOCATION: (6499)..(6752)
<223> OTHER INFORMATION: n is any nucleotide: a, c, g, t (u)

<400> SEQUENCE: 13

| | | |
|---|---|---|
| aatgtgcagg atgacaagat ggagcaaaca gtgcttgtac caccaggacc tgacagcttc | 60 | |
| aacttcttca ccagagaatc tcttgcggct attgaaagac gcattgcaga agaaaaggca | 120 | |
| aagaatccca aaccagacaa aaaagatgac gacgaaaatg gcccaaagcc aaatagtgac | 180 | |
| ttggaagctg gaaagaacct tccatttatt tatggagaca ttcctccaga gatggtgtca | 240 | |
| gagcccctgg aggacctgga cccctactat atcaataaga aaacttttat agtattgaat | 300 | |
| aaagggaagg ccatcttccg gttcagtgcc acctctgccc tgtacatttt aactcccttc | 360 | |
| aatcctctta ggaaaatagc tattaagatt ttggtacatt cattattcag catgctaatt | 420 | |
| atgtgcacta ttttgacaaa ctgtgtgttt atgacaatga gtaaccctcc tgattggaca | 480 | |
| aagaatgtag aatacacctt cacaggaata tatactttg aatcacttat aaaaattatt | 540 | |
| gcaaggggat tctgtttaga agattttact ttccttcggg atccatggaa ctggctcgat | 600 | |
| ttcactgtca ttacatttgc gtacgtcaca gagtttgtgg acctgggcaa tgtctcggca | 660 | |
| ttgagaacat tcagagttct ccgagcattg aagacgattt cagtcattcc aggcctgaaa | 720 | |
| accattgtgg agcccctgat ccagtctgtg aagaagctct cagatgtaat gatcctgact | 780 | |
| gtgttctgtc tgagcgtatt tgctctaatt gggctgcagc tgttcatggg caacctgagg | 840 | |
| aataaatgta tacaatggcc tcccaccaat gcttccttgg aggaacatag tatagaaaag | 900 | |
| aatataactg tgaattataa tggtacactt ataaatgaaa ctgtctttga gtttgactgg | 960 | |
| aagtcatata ttcaagattc aagatatcat tatttcctgg agggtttttt agatgcacta | 1020 | |
| ctatgtggaa atagctctga tgcaggccaa tgtccagagg gatatatgtg tgtgaaagct | 1080 | |
| ggtagaaatc ccaattatgg ctacacaagc tttgatacct tcagttgggc tttctgtcc | 1140 | |
| ttgtttcgac taatgactca ggacttctgg gaaaatcttt atcaactgac attacgtgct | 1200 | |
| gctgggaaaa cgtacatgat atttttttgtg ttggtcattt tcttgggctc attctaccta | 1260 | |
| ataaatttga tcctggctgt ggtggccatg gcctacgagg aacagaatca ggccaccttg | 1320 | |
| gaagaagcag aacagaaaga ggccgaattt cagcagatga ttgaacagct taaaaagcaa | 1380 | |
| caggaggcag ctcagcaggc agcaacggca actgcctcag aacattccag agagcccagt | 1440 | |
| gcagcaggca ggctctcaga cagctcatct gaagcctcta gttgagttc caagagtgct | 1500 | |

```
aaggaaagaa gaaatcggag gaagaaaaga aaacagaaag agcagtctgg tggggaagag    1560
aaagatgagg atgaattcca aaaatctgaa tctgaggaca gcatcaggag gaaaggtttt    1620
cgcttctcca ttgaagggaa ccgattgaca tatgaaaaga ggtactcctc cccacaccag    1680
tctttgttga gcatccgtgg ctccctattt tcaccaaggc gaaatagcag aacaagcctt    1740
ttcagcttta gagggcgtgc aaaggatgtg ggatctgaga acgacttcgc agatgatgag    1800
cacagcacct ttgaggataa cgagagccgt agagattcct tgtttgtgcc ccgacgacac    1860
ggagagagac gcaacagcaa cctgagtcag accagtaggt catcccggat gctggcagtg    1920
tttccagcga atgggaagat gcacagcact gtggattgca atggtgtggt ttccttggtt    1980
ggtggacctt cagttcctac atcgcctgtt ggacagcttc tgccaggggg aacaaccact    2040
gaaactgaaa tgagaaagag aaggtcaagt tctttccacg tttccatgga ctttctagaa    2100
gatccttccc aaaggcaacg agcaatgagt atagccagca ttctaacaaa tacagtagaa    2160
gaacttgaag aatccaggca gaaatgccca ccctgttggt ataaattttc caacatattc    2220
tcaatctggg actgttctcc atattggtta aaagtgaaac atgttgtcaa cctggtcgtg    2280
atggacccat ttgttgacct ggccatcacc atctgtattg tcttaaatac tcttttcatg    2340
gccatggagc actatccaat gacggaccat ttcaataatg tgcttacagt aggaaacttg    2400
gttttcactg ggatctttac agcagaaatg tttctgaaaa ttattgccat ggatccttac    2460
tattatttcc aagaaggctg aatatctttt gacggtttta ttgtgacgct agcctggta     2520
gaacttggac tcgccaatgt ggaaggatta tctgttctcc gttcatttcg attgctgcga    2580
gttttcaagt tggcaaaatc ttggccaacg ttaaatatgc taataaagat catcggcaat    2640
tccgtggggg ctctgggaaa tttaaccctc gtcttggcca tcatcgtctt catttttgcc    2700
gtggtcggca tgcagctctt tggtaaaagc tacaaagatt gtgtctgcaa gatcgccagt    2760
gattgtcaac tcccacaacg ctggcacatg aatgacttct tccactcctt cctgattgtg    2820
ttccgcgtgc tgtgtgggga gtggatagag accatgtggg actgtatgga ggttgctggt    2880
caagccatgt gccttactgt cttcatgatg gtcatggtga ttggaaacct agtggtcctg    2940
aatctctttc tggccttgct tctgagctca tttagtgcag acaaccttgc agccactgat    3000
gatgataatg aaatgaataa tctccaaatt gctgtggata ggatgcacaa aggagtagct    3060
tatgtgaaaa gaaaaatata tgaatttatt caacagtcct tcattaggaa acaaaagatt    3120
ttagatgaaa ttaaaccact tgatgatcta acaacaagaa aagacagttg tatgtccaat    3180
catacaacag aaattgggaa agatcttgac tatcttaaag atgtaaatgg aactacaagt    3240
ggtataggaa ctggcagcag tgttgaaaaa tacattattg atgaaagtga ttacatgtca    3300
ttcataaaca accccagtct tactgtgact gtaccaattg ctgtaggaga atctgacttt    3360
gaaaatttaa acacggaaga ctttagtagt gaatcggatc tggaagaaag caaagagaaa    3420
ctgaatgaaa gcagtagctc atcagaaggt agcactgtgg acatcggcg ccctgtagaa    3480
gaacagcccg tagtggaacc tgaagaaact cttgaaccag aagcttgttt cactgaaggc    3540
tgtgtacaaa gattcaagtg ttgtcaaatc aatgtggaag aaggcagagg aaaacaatgg    3600
tggaacctga aaggacgtg tttccgaata gttgaacata actggtttga accttcatt    3660
gttttcatga ttctccttag tagtggtgct ctggcatttg aagatatata tattgatcag    3720
cgaaagacga ttaagacgat gttggaatat gctgacaagg ttttcactta catttccatt    3780
ctggaaatgc ttcaaaatg ggtggcatat ggctatcaaa catatttcac caatgcctgg    3840
tgttggctgg acttcttaat tgttgatgtt tcattggtca gtttaacagc aaatgccttg    3900
```

```
ggttactcag aacttggagc catcaaatct ctcaggacac taagagctct gagacctcta    3960
agagccttat ctcgatttga agggatgagg gtggttgtga atgcccttt aggagcaatt    4020 ccatccatca tgaatgtgct tctggtttgt cttatattct ggctaatttt cagcatcatg    4080
ggcgtaaatt tgtttgctgg caaattctac cactgtatta acaccacaac tggtgacagg    4140
tttgacatcg aagacgtgaa taatcatact gattgcctaa aactaataga aagaaatgag    4200
actgctcgat ggaaaaatgt gaaagtaaac tttgataatg taggatttgg gtatctctct    4260
ttgcttcaag ttgccacatt caaggatgg atggatataa tgtatgcagc agttgattcc    4320
agaaatgtgg aactccagcc taagtatgaa gaaagtctgt acatgtatct ttactttgtt    4380
attttcatca tctttgggtc cttcttcacc ttgaacctgt ttattggtgt catcatagat    4440
aatttcaacc agcagaaaaa gaagtttgga ggtcaagaca tctttatgac agaagaacag    4500
aagaaatact ataatgcaat gaaaaaatta ggatcgaaaa aaccgcaaaa gcctatacct    4560
cgaccaggaa acaaatttca aggaatggtc tttgacttcg taaccagaca gttttttgac    4620
ataagcatca tgattctcat ctgtcttaac atggtcacaa tgatggtgga aacagatgac    4680
cagagtgaat atgtgactac cattttgtca cgcatcaatc tggtgttcat tgtgctattt    4740
actggagagt gtgtactgaa actcatctct ctacgccatt attatttac cattggatgg    4800 aatattttg attttgtggt tgtcattctc tccattgtag gtatgtttct tgccgagctg    4860
atagaaaagt atttcgtgtc ccctaccctg ttccgagtga tccgtcttgc taggattggc    4920
cgaatcctac gtctgatcaa aggagcaaag gggatccgca cgctgctctt tgctttgatg    4980
atgtcccttc ctgcgttgtt taacatcggc ctcctactct tcctagtcat gttcatctac    5040
gccatctttg gatgtccaa cttttgccta tgttaagagg aagttgggat cgatgacatg    5100
ttcaactttg agcctttgg caacagcatg atctgcctat tccaaattac aacctctgct    5160
ggctgggatg gattgctagc acccattctc aacagtaagc cacccgactg tgaccctaat    5220
aaagttaacc ctggaagctc agttaaggga gactgtggga acccatctgt tggaattttc    5280
ttttttgtca gttacatcat catatccttc ctggttgtgg tgaacatgta catcgcggtc    5340
atcctggaga acttcagtgt tgctactgaa gaaagtgcag agcctctgag tgaggatgac    5400
tttgagatgt tctatgaggt ttgggagaag tttgatcccg atgcaactca gttcatggaa    5460
tttgaaaaat tatctcagtt tgcagctgcg cttgaaccgc ctctcaatct gccacaacca    5520
aacaaactcc agctcattgc catggatttg cccatggtga gtggtgaccg gatccactgt    5580
cttgatatct tatttgcttt tacaaagcgg gttctaggag agagtggaga gatggatgct    5640
ctacgaatac agatggaaga gcgattcatg gcttccaatc cttccaaggt ctcctatcag    5700
ccaatcacta ctactttaaa acgaaaacaa gaggaagtat ctgctgtcat tattcagcgt    5760
gcttacagac gccacctttt aaagcgaact gtaaaacaag cttcctttac gtacaataaa    5820
aacaaaatca aggtggggc taatcttctt ataaaagaag acatgataat tgacagaata    5880
aatgaaaact ctattacaga aaaaactgat ctgaccatgt ccactgcagc ttgtccacct    5940
tcctatgacc gggtgacaaa gccaattgtg gaaaacatg agcaagaagg caaagatgaa    6000
aaagccaaag ggaaataaat gaaaataat aaaataatt gggtgacaaa ttgtttacag    6060
cctgtgaagg tgatgtattt ttatcaacag gactcctta ggaggtcaat gccaaactga    6120
ctgtttttac acaaatctcc ttaaggtcag tgcctacaat aagacagtga ccccttgtca    6180
gcaaactgtg actctgtgta aagggagat gaccttgaca ggagattact gttctcacta    6240
ccagctgaca ctgctgaaga taagatgcac aatggctagt cagactgtag ggaccagttt    6300
```

```
caaggggtgc aaacctgtga ttttggggtt gtttaacatg aaacacttta gtgtagtaat    6360
tgtatccact gtttgcattt caactgccac atttgtcaca ttttatgga atctgttagt    6420 ggattcatct ttttgttaat ccatgtgttt attatatgtg actattttg taaacgaagt    6480 ttctgttgag aaataggcna aggacctcta taacangtat gccacctggg gggtanggca    6540
accacatggc nctcccagct acacaaagtc gtggtttgca tgagggcatg ctgcacttag    6600
agatcatgca tgagaaaaag tcacaagaaa aacaaattct taaatttcac catatttctg    6660
ggaggggtaa ttgggngata agtggaggtg ctttgttgat cttgttttgc gaaatccagc    6720
ccctanacca agtagattgt ttgtgggtag gncagtaaat cttagcaggt gcaaacttca    6780
ttcaaatgtt tggagtcata aatgttatgt ttcttttgt tgtattaaaa aaaaacctga    6840
atagtgaata ttgcccctca ccctccaccg ccagaagact gaattgacca aaattactct    6900
ttataaattt ctgcttttc ctgcactttg tttagccatc ttcggctctc agcaaggttg    6960
acactgtata tgttaatgaa atgctatta ttatgtaaat agtcatttta ccctgtggtg    7020
cacgtttgag caaacaaata acgacctaag cacagtattt attgcatcaa atatgtacca    7080
caagaaatgt agagtgcaag ctttacacag gtaataaaat gtattctgta ccatttatag    7140
atagtttgga tgctatcaat gcatgtttat attaccatgc tgctgtatct ggtttctctc    7200
actgctcaga atctcattta tgagaaacca tatgtcagtg gtaaagtcaa ggaaattgtt    7260
caacagatct catttattta agtcattaag caatagtttg cagcactta acagcttttt    7320 ggttatttt acatttaag tggataacat aggtatatag ccagactgta cagacatgtt    7380 taaaaaaca cactgcttaa cctattaaat atgtgtttag aattttataa gcaaatataa    7440
atactgtaaa aagtcactt attttattt tcagcattat gtacataaat atgaagagga    7500
aattatcttc aggttgatat cacaatcact tttcttactt tctgtccata gtactttttc    7560
atgaaagaaa tttgctaaat aagacatgaa aacaagactg ggtagttgta gatttctgct    7620
ttttaaatta catttgctaa ttttagatta tttcacaatt ttaaggagca aaataggttc    7680
acgattcata tccaaattat gctttgcaat tggaaaaggg tttaaaattt tatttatatt    7740
tctggtagta cctgtactaa ctgaattgaa ggtagtgctt atgttatttt tgttcttttt    7800
ttctgacttc ggtttatgtt ttcatttctt tggagtaatg ctgctctaga ttgttctaaa    7860
tagaatgtgg gcttcataat ttttttttcc acaaaaacag agtagtcaac ttatatagtc    7920
aattacatca ggacattttg tgtttcttac agaagcaaac cataggctcc tcttttcctt    7980
aaaactactt agataaactg tattcgtgaa ctgcatgctg gaaaatgcta ctattatgct    8040
aaataatgct aaccaacatt taaaatgtgc aaaactaata aagattacat tttttattcg    8100
aaaaaaggaa aaaaaaaaa aaaaaaaaa a                                    8131
```

<210> SEQ ID NO 14
<211> LENGTH: 6586
<212> TYPE: DNA
<213> ORGANISM: Rattus norvegicus
<220> FEATURE:
<221> NAME/KEY: misc_feature
<222> LOCATION: (6539)..(6579)
<223> OTHER INFORMATION: n is any nucleotide: a, c, g, t (u)

<400> SEQUENCE: 14

```
ccaagatggc gcccaccgca gtcccgcccg ccgcagcctc ggcgcctctg cagtccggcc     60
gcgcctcccg ggccccgcgc tagggccgct gccgcctcgc ccgccgccgc cgccgccagc    120
tgacctgtcc cggacacata actaacgaag ctgctgcagg atgagaagat ggcagcgcgg    180
```

```
ctgctcgcac caccaggccc tgatagtttc aagcctttca cccctgagtc gctggcaaac    240
atcgagaggc gtattgccga gagcaagctc aagaaaccac caaaggcgga tggcagccac    300
cgggaggacg atgaagacag caagcccaag ccaaacagtg acctggaggc tgggaagagt    360
ttgcctttca tctacgggga catcccgcaa ggcctggttg cggttcccct ggaggacttt    420
gacccttact atttgacgca gaaaaccttt gtagtattaa acagagggaa aactctcttc    480
agatttagtg ccacacctgc cttgtacatt ttaagccctt ttaacctgat aagaagaata    540
gctattaaaa ttttgataca ctcagttttc agcatgatca tcatgtgcac catcctgacc    600
aactgtgtgt tcatgacctt tagtaaccct ccagaatggt ccaagaatgt ggagtacaca    660
ttcacaggga tttacacatt tgaatcacta gtgaaaatca tcgcaagagg tttctgcata    720
gacggcttca ccttcttgcg agacccgtgg aactggttag acttcagtgt catcatgatg    780
gcatatgtga cagagtttgt ggacctgggc aatgtctcag cgctgagaac attcagggtt    840
ctccgagctt tgaaaactat ctctgtaatt ccaggcctga agacaatcgt gggcgcccta    900
atccagtccg tgaagaagct gtcggacgtg atgatcctga cagtgttctg cctgagtgtt    960
ttcgccctga ttggcctgca gctcttcatg gggaaccttc gaaacaagtg tgtcgtgtgg   1020
cccataaact tcaacgagag ctacctggag aacggcacca gaggctttga ctgggaggaa   1080
tatatcaaca ataaaacaaa cttttacatg gttcctggca tgctagaacc cttgctctgc   1140
gggaacagtt ctgatgctgg gcaatgccca gagggattcc agtgcatgaa gcaggaagg    1200
aaccccaact acgttacaca cagctttgac accttcagct gggccttctt ggcattattc   1260
cgccttatga cccaggacta ttgggagaac ttataccagc tgaccttacg agccgctggg   1320
aaaacgtaca tgatcttctt tgtcttggtc atcttcgtgg gttctttcta tctggtgaac   1380
ttgatcttgg ctgtggtggc catggcttat gaggaacaga accaggcaac actggaggag   1440
gcagagcaaa aagaggccga gttcaaggca atgctggagc aactcaagaa gcagcaggag   1500
gaggcacagg ctgctgcaat ggccacctca gcgggcactg tctcggaaga cgccattgaa   1560
gaagaagggg aagatggggt aggctctccg aggagctctt ctgaactgtc taaactcagt   1620
tccaagagcg cgaaggagcg gcggaaccga cggaagaaga ggaagcagaa ggagctctct   1680
gaaggcgagg agaaaggga cccggagaag gtgtttaagt cagagtcgga agacggtatg   1740
agaaggaagg ccttccggct gccagacaac aggatagggaa ggaagttttc catcatgaat   1800
cagtcgctgc tcagcattcc aggctcgccc ttcctctccc gacataacag caaaagcagc   1860
atcttcagct tccggggacc cggtcggttc cgggaccccg gctctgagaa tgagttcgca   1920
gacgatgaac acagcaccgt ggaggagagc gagggccggc gtgactcgct cttcatcccg   1980
atccgcgccc gcgagcgccg cagcagctac agtggctaca gcggctacag ccagtgcagc   2040
cgctcgtcgc gcatcttccc cagcctgcgc gcagcgtga agcgcaacag cacggtggac   2100
tgcaacggcg tagtgtcact catcgggccc ggctcacaca tcgggcggct cctgcctgag   2160
gtgaaaatag ataaggcagc tacgacagc gcaacgactg aggtgaaaat taagaagaaa   2220
ggccctggat ctcttttagt ttctatggac caactcgcct cctacggacg aaggacagaa   2280
atcaacagca taatgagcgt ggtcacaaac acgctagtgg aagagctgga agagtctcag   2340
agaaagtgcc caccgtgctg gtataagttt gccaacactt tcctcatctg ggagtgtcac   2400
ccctactgga taaaactgaa ggagatcgtg aacttaatcg tcatggaccc ttttgtagac   2460
ttagccatca ccatctgcat cgttctgaat acgctattta tggcaatgga gcaccatccc   2520
atgacaccac agttcgaaca cgtcttggcc gtaggaaatc tggtgttcac cgggatcttc   2580
```

```
acggcggaaa tgtttctgaa gctcatagcc atggacccct actattattt ccaagaaggc    2640
tggaacattt ttgacggatt tattgtctcc ctcagtttaa tggagctgag tctcgcagat    2700
gtggaggggc tctcagtgct gcggtctttc cgactgctcc gagtcttcaa gctggccaag    2760
tcctggccca ccctgaacat gctgatcaag atcatcggga actccgtggg tgccctgggc    2820
aacctgaccc tggtgctggc catcatcgtc ttcatcttcg ccgtggtggg gatgcagctg    2880
tttggaaaga gttacaagga gtgcgtctgt aagatcaacc aggagtgcaa gctcccgcgc    2940
tggcacatga acgacttctt ccactccttc ctcatcgtct tccgagtgct gtgtggggag    3000
tggatcgaga ccatgtggga ctgcatggag gtggccggcc aggccatgtg cctcattgtc    3060
ttcatgatgg ttatggtcat tggcaacctg gtggtgctga atctattcct ggccttgctt    3120
ctgagctcct tcagcgcaga caacctggcg ccacagacg acgacgggga aatgaacaac    3180
ctgcagatct cagtgatccg gatcaagaag ggcgtggcct ggaccaaagt gaaggtgcac    3240
gccttcatgc aggctcactt caagcagcgg gaggcggatg aagtgaaacc cctcgacgag    3300
ctgtatgaga agaaggccaa ctgcatcgcc aaccacacgg gcgtggatat ccaccggaac    3360
ggcgacttcc agaagaacgg gaacggaacc accagcggca tcggcagcag cgtggagaag    3420
tacatcatcg acgaggacca catgtccttc attaacaacc caaacctgac cgtccgggtg    3480
cccattgctg tgggcgagtc tgacttcgag aacctcaaca cagaggatgt tagcagcgaa    3540
tcagaccctg aaggcagcaa agataaactg gacgatacca gctcctcaga aggaagtacc    3600
atcgacatca agcctgaggt ggaagaagtt cccgtggagc aacctgagga atacttggat    3660
ccggacgcct gctttacaga gggttgcgtc cagcggttca gtgctgccca ggtcaacatc    3720
gaggaaggac taggcaagtc gtggtggatc ttgcggaaaa cctgcttcct cattgtggag    3780
cacaattggt ttgagacctt catcatcttc atgattctgc tcagcagtgg cgccctggcc    3840
tttgaggaca tctacattga gcagaggaag accatccgca ccatcctgga gtatgcggac    3900
aaggtcttca cctacatctt catcctggag atgttgctca gtggacagc ctacggcttc    3960 gtcaagttct tcaccaatgc ctggtgctgg ttggacttcc tcattgtggc tgtctcttta    4020
gtcagcctta tagctaatgc cctgggctac tcggaactag gtgccataaa gtcccttagg    4080
accctaagag ctttgagacc cttaagagcc ttatcacgat ttgaagggat gagggtggtg    4140
gtgaatgcct tggtgggcgc catcccctcc atcatgaatg tgctgctggt gtgtctcatc    4200
ttctggctga ttttcagcat catgggagtt aacctgtttg cggggaaata ccactactgc    4260
tttaatgaga cttctgaaat ccggttcgaa atcgatattg tcaacaataa aacgactgt    4320 gagaagctca tggagggcaa cagcacggag atccgatgga gaatgtcaa gatcaacttt    4380 gacaatgtcg gagcagggta cctggcccctt cttcaagtgg caaccttcaa aggctggatg    4440
gacatcatgt atgcggctgt agattcccga aagccagacg agcagcctga ctacgagggc    4500
aacatctaca tgtacatcta cttcgtcatc ttcatcatct tcggctcctt cttcaccctc    4560
aacctgttca tcggtgtcat catcgacaac ttcaaccagc agaagaaaaa gtttggaggt    4620
caggacatct tcatgacaga ggaacagaag aagtactaca atgccatgaa aaagctgggc    4680
tccaagaagc cacagaagcc catcccccga cccttgaaca aaatccaagg gattgtcttt    4740
gatttcgtca ctcaacaagc ctttgacatt gtgatcatga tgctcatctg ccttaacatg    4800
gtgacaatga tggtggagac agacactcag agcaagcaga tggagaacat tcttactgg    4860 attaatctgg tctttgtcat cttcttcacc tgcgagtgtg tgctcaaaat gtttgccttg    4920
agacactact atttcaccat tggctggaac atctttgact ttgtggtggt catcctctcc    4980
```

```
attgtgggaa tgttcctggc tgatatcatt gagaagtact tcgtctcccc aaccctattc    5040
cgagttatcc gattggcccg tattgggcgc atcttgcgtc tgatcaaggg cgccaaaggg    5100
atccgcaccc tgctctttgc cttaatgatg tcgctgcccg ccctgttcaa catcggcctc    5160
ctgctcttcc tcgtcatgtt catcttctcc atttttggca tgtccaactt cgcatacgtg    5220
aagcacgagg ccggcattga cgacatgttc aacttcgaga catttggcaa cagcatgatc    5280
tgtttgttcc agatcacaac gtctgctggc tgggatggcc tgctgctgcc aatcctgaac    5340 cgccccctg  actgcagctt ggacaaagag cacccaggga gtggcttcaa aggggactgt    5400
gggaacccct cggtgggcat cttcttcttt gtgagctaca tcatcatctc cttcctgatt    5460
gtggtgaaca tgtacatcgc catcatcctg gagaacttca gcgtggccac cgaggagagc    5520
gccgaccctc tgagtgagga tgacttcgag actttctatg agatctggga agagtttgac    5580
ccagacgcca cccagttcat cgagtactgt aagctggcag actttgccga cgccctggag    5640
cacccgctcc gagtacccaa gcccaacacc atcgagctca tcgccatgga cctgcccatg    5700
gtgagcggag atcgcatcca ctgcttggac atcctttccg ccttcaccaa gcgagtcctg    5760
ggagacagtg gggagttgga catcctgcgc agcagatgg  aggagcggtt cgtggcatcc    5820
aatccttcca aagtgtctta cgagcctatc acaaccactc tgcggcgcaa gcaggaggag    5880
gtgtctgcag tggtcctgca gcgtgcctac aggggacact ggctaggcg  gggcttcatc    5940 tgcagaaaga tggcctccaa caagctggag aatggaggca cacacagaga caagaaggag    6000
agcaccccgt ccacagcctc cctccccctct tacgacagcg tcacaaagcc agacaaggag    6060
aagcagcagc gtgcggagga gggcagaagg gaaagagcca agaggcaaaa agaggtcagg    6120
gagtccaagt gctagaggag gggaaaggaa gcttaccccg gctgaacact ggcaagtgaa    6180
agcttgttta caaacttccg aatctcacgg atgcagagca gctgtgcaga cgctcgctgt    6240
actggaagac ctataccaaa catagtctgc ttacatgtga catggtggca tcctgagcgg    6300
tgactgctgg ggacaaagga ccctgctccc tggactcaca gatctcctat cgcttgggca    6360
gacggttact gcatgttcca cacttagtca atgcaactta ggactaaact aaccaggata    6420
caaaaccgag gcggctgccg ggaccagcag atcaccgctg cagccaaatg gattttattt    6480
tttcattttg ttgattctca gaagcagaaa gcatcacttt aaaagtttgt ttgttcatnc    6540
aaacaatatt tgaattctta cattagttaa gctaagcanc aaaaag              6586
```

<210> SEQ ID NO 15  
<211> LENGTH: 5858  
<212> TYPE: DNA  
<213> ORGANISM: Mus musculus

<400> SEQUENCE: 15

```
tggtgccctg agcctcccta gcaggaagac agtgtctgag ccaagggtga agatggagga      60
gaggtactat ccagtgatct tcccagacga gaggaatttc cgcccttca  ctttcgactc     120 tttggctgca atagagaagc ggatcaccat ccaaaaggag aagaagaaat ccaaagacaa     180
ggcagcaact gagccccagc ctcggcctca gctcgaccta aaggcctcca ggaagttacc     240
taagctctat ggcgacgttc cccctgacct tatagcgaag cccctggaag atctggaccc     300
attttacaaa gaccataaga cattcatggt attgaacaag aagagaacaa tctatcgctt     360
cagcgccaag agggccttgt tcattctggg gccttttaat cccatcagaa gcttcatgat     420
tcgcatctct gtccattcag tcttcagcat gttcattatc tgcacagtga tcatcaactg     480
tatgttcatg gctaataatt cttctgtgga cagtcgtcct agcagtaaca ttcccgaata     540
```

```
cgtcttcatt gggatttatg ttttagaagc tgtgattaaa atattggcaa gaggcttcat    600
tgtggatgag ttttcctacc tccgagatcc ttggaactgg ctggacttca ttgtcatcgg    660
aacagcgata gcgccttgtt ttctcggtaa caaagtcaat aatcttttcca ctctacgtac    720 cttccgagtg ttgagagctc tgaaagccat ttctgtaatc tcaggtctga aggtcatcgt    780
gggtgccctg ctgcgctccg tgaagaagct agtggacgtg atggtcctca ctctcttttg    840
cctcagcatc tttgccctgg ttggtcagca gctcttcatg gaattctga gccagaaatg     900 tattaaggac gactgtggcc ctaacgcttt ttccaacaag gattgctttg taaaagaaaa    960
tgatagcgag gacttcataa tgtgtggcaa ctggctcggc agaagatcct gccccgatgg   1020
ttccacgtgc aataaaacca catttaaccc agattataat tatacaaact ttgacagctt   1080
tggctggtct tttctcgcca tgttccgggt tatgactcaa gactcctggg agaagcttta   1140
tcgacagatc cttcgcacct ccgggatcta ctttgtcttc ttcttcgtgg tcgtcatctt   1200
cctgggctct ttctacctgc ttaacttaac cctggctgtc gtcaccatgg cttacgagga   1260
acagaacaga aatgtcgctg ccgagacaga ggccaaggag aagatgtttc aggaagccca   1320
gcagctgttg agggaggaaa aggaggctct ggttgccatg gaattgaca gaacttccct    1380 taattccctc caagcttcgt ccttttcccc aaagaagagg aagttttttg gcagtaagac   1440
aagaaagtcc ttctttatga gagggtccaa gacagcccga gcctcagcgt ccgattcaga   1500
ggacgatgcc tctaaaaacc cacaactcct tgagcaaaca aaacgactat cccagaactt   1560
gcccgtagaa ctctttgatg agcacgtgga ccccctccat aggcagagag cgctgagtgc   1620
cgtcagtatc ttaaccatca ccatgcagga acaagaaaaa tcccaggagc cttgtttccc   1680
gtgtgggaaa aacttggcat ccaagtacct ggtgtgggaa tgtagccctc cgtggctgtg   1740
cataaagaag gtcctgcaga ctatcatgac agacccttc actgagctgg ccatcaccat    1800
ctgcatcatc gtcaatactg tcttcttggc catggaacac cacaatatgg ataactcttt   1860
aaaagacata ctgaaaatag gaaactgggt tttcactgga attttcatag cggaaatgtg   1920
tctcaagatc attgcgctag acccttacca ctacttccgg cacggctgga acatctttga   1980
cagcattgtg gcccttgtga gtctcgctga cgtgctcttc cacaaactgt ctaaaaacct   2040
ctccttcttg gcttccctca gagtgctgag ggtcttcaag ttagccaaat cctggcccac   2100
attaaacact ctcattaaga tcatcggcca ctccgtgggt gcgctcggaa acctgactgt   2160
ggtcctaacg atcgtggtct tcatctttttc cgtggttggc atgcggctct ttggtgccaa   2220
gtttaacaag acttgctcca cctctccgga gtccctccgg cgctggcaca tgggtgattt   2280
ctaccattcc ttcctggtgg tgttccgcat cctctgtggg gagtggatcg agaacatgtg   2340
ggaatgcatg caggagatgg aaggctcccc gctgtgtgtc atcgtctttg tgctgatcat   2400
ggtggtcggg aagctcgtgg tgcttaacct cttcattgcc ttgctgctca attccttcag   2460
caatgaggaa aaggatggga acccagaagg agagaccagg aaaaccaaag tgcagctagc   2520
cctggatcgg ttcagccgag cgttctactt catggcgcgc gctcttcaga atttctgttg   2580
caagagatgc aggaggcaaa actcgccaaa gccaaatgag gcaacagaaa gctttgctgg   2640
tgagagtaga gacacagcca ccctggatac aaggtcctgg aaggagtatg attcagaaat   2700
gactctgtac actgggcagg ccggggctcc actggcccca ctggcaaaag aagaggacga   2760
tatggaatgt tgtggtgaat gtgatgcctc acctacctca cagcctagtg aggaagctca   2820
ggcctgtgac ctccctctga agaccaagcg gctcccagc ccagatgacc acggggttga    2880
aatggaagtg ttttccgaag aagatccgaa tttaaccata cagagtgctc gaaagaagtc   2940
```

```
tgatgcggca agcatgctct cagaatgcag cacaatagac ctgaatgata tctttagaaa   3000
tttacagaaa acagtttccc cccaaaagca accagatcga tgctttccca agggcctcag   3060
ttgtatcttt ctatgttgca aaacaatcaa aaaaaagtcc ccctgggtcc tgtggtggaa   3120
tcttcggaaa acctgctacc aaatcgtgaa gcatagctgg tttgagagct tcataatttt   3180
tgtcatcctg ctgagcagcg gagcactgat attcgaagat gtcaatcttc ccagccggcc   3240
ccaagttgaa aaattactga agtgtaccga taatatttttc acatttatttt ttctcctgga   3300 aatgattttg aagtgggtgg cctttggatt ccggaagtat ttcaccagtg cctggtgctg   3360
gctcgatttc ctcattgtgg tggtgtctgt gctcagcctc acgaacttac caaacttgaa   3420
gtccttccgg aatctgcgag cgctgagacc tctgcgggca ctgtctcagt ttgaaggaat   3480
gaaggttgtt gtcaatgccc tcatgagtgc catacctgcc atcctcaatg tcttgctggt   3540
ctgcctcatt ttctggctca tattttgtat cctgggagta aatttttttt ctgggaagtt   3600
tggaagatgc attaatggaa cagacataaa taaatatttc aacgcttcca atgttccaaa   3660
ccaaagccaa tgtttagtta gtaattacac gtggaaagtc ccgaatgtca actttgacaa   3720
cgtggggaat gcctaccttg ccctgctgca agtggcgacc tataagggct ggctggacat   3780
tatgaatgca gctgttgatt ccagagggaa agatgagcag ccggcctttg aggcgaatct   3840
atacgcatac ctttacttcg tggttttttat catcttcggc tcattcttta ccctgaacct   3900
ctttatcggt gttattattg acaacttcaa tcagcagcag aaaaagttag gtggccaaga   3960 cattttatg acagaagaac agaagaaata ttacaatgca atgaaaaagt taggaaccaa   4020
gaagcctcaa aagcccatcc caaggcccct gaacaaatgt caagccttcg tgttcgattt   4080
ggtcacaagc caggtctttg acgtcatcat tctgggtctt attgtcacaa acatgattat   4140
catgatggct gaatctgaag gccagcccaa cgaagtgaag aaaatctttg atattctcaa   4200
catagtcttc gtggtcatct ttaccgtaga gtgtctcatc aaagtctttg ctttgaggca   4260
acactacttc accaatggct ggaacttatt tgattgtgtg gtcgtggttc tttccatcat   4320
tagtaccttg gttctggct tggagaacag caacgtcttc ccgcccacac tcttcaggat   4380
tgtccgcttg gctcggatcg gtcgaatcct cagactggtc cgggcggctc gaggaatcag   4440
gacactcctt ttcgcgttga tgatgtctct cccctctctc ttcaacattg gtctgcttct   4500
ctttctggtg atgttcattt atgccatctt tgggatgaac tggttttcca aagtgaagag   4560
aggctctggg attgatgaca tcttcaactt tgacactttc tcgggcagca tgctctgcct   4620
cttccagata accacttcag ccggctggga tgctctcctc aaccccatgc tggaatcaaa   4680
agcctcttgc aattcctcct cccaagagag ctgtcagcag ccgcagatag ccatagtcta   4740
cttcgtcagc tacatcatca tctcctttct cattgtggtt aacatgtaca tagctgtgat   4800
tctagagaac ttcaacacag ccacagagga gagcgaggac cccctgggcg aagacgactt   4860
tgagatcttc tatgagatct gggagaagtt tgaccccgaa gcaacacagt tcatccagta   4920
ctcatccctc tctgcttcg ccgacgccct gcccgagccg ttgcgtgtgg ccaagcccaa   4980
caggtttcag tttctcatga tggacttgcc catggtgatg ggtgatcgcc tccattgcat   5040
ggatgttctc tttgctttca ccaccagggt cctcgggaac tccagcggct tggataccat   5100
gaaagccatg atggaggaga agttcatgga ggccaatcct ttcaagaagt tgtacgagcc   5160
cattgtcacc accacaaaga ggaaggagga ggaggaatgt gccgctgtca tccagagggc   5220
ctaccggaga cacatggaga agatgatcaa gctgaagctg aaaggcaggt caagttcatc   5280
gctccaggtg ttttgcaatg gagacttgtc tagcttggat gtgcccaaga tcaaggttca   5340
```

```
ttgtgactga aaccccccacc tgcacgccta cctcacagcc tcacagctca gcccccagcc    5400
tctggcgaac aagcggcgga ctcaccgaac aggccgttca acttgttttt ttgggtgaaa    5460
gaggtgatag gttggtgtcc atttttaaat gattcttgga aagattgaac gtcggaacat    5520
gttagaaagg actgccaagg acatccacag taacggaagg cctgaaggac agttcaaatt    5580
atgtaaagaa acgagaagga aaggtcacat gtctgttcag ttttaagtat gtgacctgcc    5640
acatgtagct cctttgcatg ttaagtgaga agtcaaaacc ctgccataag taaatagctt    5700
tgttgcaggt gtttctacca gtgctgccga tttgggtgta tggctcaaac ctgaaagcat    5760
gactctgact tgtcagcacc ccaactttca gaagctctga tctctgtcct aggtgtttga    5820
caaataaata cataaaaaaa aaaaaaaaaa aaaaaaaa                            5858
```

<210> SEQ ID NO 16
<211> LENGTH: 6503
<212> TYPE: DNA
<213> ORGANISM: Bos Taurus

<400> SEQUENCE: 16

```
cgggacccgg gccgggggac cagcagcttc ccttcaggca gcgtgaggac agcctgtgcc      60
ccagaagcag gatgagaaga tggcagcctt cctgttacct cggggcacca gcagcttccg     120
caggttcacc cgggagtctc tggcggccat cgagaagcgc atggcagaga agcaggcccg     180
gagctcggcc gcctcgcagg agagccgcga cgggctgccc gaggaggagg cgccccggcc     240
ccagctggac ctgcaagcct ccaaaaagct gccggatctc tacggcaacc cacccccgaga    300 gctcatcggg gagcccctgg aggacctgga ccccttctat agcactcaaa agaccttcat     360
cgtcctgaac aaaggcaaga ccatcttccg gttcagcgcc accaacgcct tgcatgtcct     420
cagccccttc cacccccatcc ggagagtggc tgtgaagatc ttggtgcatt cgctcttcag    480
catgctcatc atgtgtacca ttctgaccaa ctgcgtgttc atggcccagc acgaccctcc     540
gccctggacc aaatatgtcg agtacatctt cactgccatc tacacctttg agtctctggt     600
caagattctg gctcgaggct tctgcctgca cgcgttcacc ttccttcggg acccgtggaa     660
ctggctggac ttcagcgtga tcatcatggc atacaccact gaatttgtgg acctgggcaa     720
tgtctcagct ttacgtacct tccgagtcct ccgggccctg aaaactatat cagtcatttc     780
aggcctgaag accatcgtgg gggccctgat ccagtctgtg aagaagctgg ccgatgtgat     840
ggtcctcacg gtcttctgcc tcagcgtctt cgccctcatc ggccttcagc tcttcatggg     900
caacctgagg cacaagtgcg tccgcaactt cacggtgctc aacggcacca acagcaccaa     960
tgcctccgtg gaggccgacg gcctgatctg ggcatcgctg gacgactacc tcaacgaccc    1020
agaaaattac ctactcaaga tggcacctc tgacgtgtta ctgtgtggga acagctccga    1080
cgctgggaca tgtcctgagg ctacaggtc cctgaaggca ggtgggaacc ctgaccatgg    1140
ctacaccagc ttcgactcct tcgcctgggc cttcctcgca ctcttccgac tgatgacgca    1200
ggactgctgg gagcgcctct accagcagac cctgaggtct gcaggaagaa tctacatgat    1260
cttcttcatg ctggtcatct tcctgggctc cttctacttg gtgaacttga tcctggctgt    1320
ggtcgccatg gcctacgagg agcaaaacca agccaccatc gcagagacag aggaaggaa     1380 aaagcgattc caggaagcca tggagttgct caagaaagag caggaggccc tcgccatcag    1440
gggtgtggac accgtgtccc gcagctcctt ggagatgtcc ccattggccc cagtaaccac    1500
ccacgagaga aggagcaaga gaagaaaacg aatgtcttca gggatggaag agtgtggga    1560 cgacaagttc cccaagtccg actcagagga tggtcccga gcagtgaatc gtttcagcat     1620
```

```
cacccatggc ctcagcagga cctccatgaa gccgcgctcc agccacggga gcattttcac    1680
cttccgccga cgggacctgg gctccgagac agattttgcg gacgatgaaa acagcaccgc    1740
cggggacagt gagagccacc gcacatcact gctggtgcct tggcccctgc ggcggcctag    1800
taccctggga cagcccagtc ccggaacctc aactcccggc cacgtgctca acggcaaaag    1860
gaacagcact gtggactgta acggggtggt ctccttgctg ggggcaggag accccgaggc    1920
cacctcccca gggagtcacc tcctccaccc tatgaagctg gagcgccccc cagacacgac    1980
cacaccatcg gaggagccgg gcaggcccca cacgctgacg ccccaggctc cgtgtgtaga    2040
cggcttcgag gagccaggag agcggcagcg agccctcagt gcagtgagcg tcctcaccag    2100
tgccctggaa gagctggagg agtctcagcg caggtgtcca ccgtgctgga tccgttttgc    2160
ccagcactac ctgatctggg agtgctgccc gctgtggatg tccattaagc agaaagtgaa    2220
gttcatggtc atggacccat ttgctgacct caccatcacc atgtgcatcg tgcttaacac    2280
gctcttcatg gcactggagc actacaacat gacgaccgaa tttgaggaga tgctgcaggt    2340
tggaaacctg gtcttcacag gaatattcac agcagagatg accttcaaga tcattgcctt    2400
ggaccnctac tactacttcc agcagggctg aacatcttc gacagcatca tcgtcatcct    2460
cagcctcatg gagctgggcc tgtcccgcat gggcaatctg tcggtgcttc gctccttctg    2520
cctgcttcgg gtcttcaagc tggccaagtc ctggccacc ctgaacacac tcatcaagat    2580
cattgggaac tcagtgggcg cgctaggcaa cctgacgttg gtgctggcca tcattgtgtt    2640
catcttcgct gtggtgggca tgcagctctt tggcaagaac tactcagagc agaggcaccg    2700
tatcagtgac tcgggcctcc tgccccgctg gcacatgatg gacttcttcc atgccttcct    2760
catcatcttc cgcatcctct gtggagagtg gatcgagacc atgtgggact gcatggaggt    2820
gtctgggcag tcactatgcc tgctggtctt cctgcttgtt atggtcattg gtaacctcgt    2880
ggtcctgaac ctcttcctgg ctttactgct cagctccttc agcgcagaca acctcacagc    2940
tcccgacgag gatggggaga tgaacaacct ccagctggct ctggcccgca tccagcgagg    3000
cctgcgcttc atcaagcgga ccacctggga cttctgctgc gtgctcctgc agcggccgcc    3060
tcagaagccc gcggccctcg cctcccaggg ccagctgccg ggctgtatcg ccacctccag    3120
cccccacccc caaccagaga gcgagaaggc gcccccagcc cgcaaggaga cgcggtttga    3180
ggaaggccag cggccaggtc agggcgcacc tgggatgcc gagcctgtgt gtgtgcccat    3240
cgccgtggcc gagtcagaca cggatgaccc cgaggaggat gaggagaaca gcctaagcac    3300
agaggaagag tccagcaagc agcaggaatc ccagctggcg tccggcagcc cagaggccct    3360
cccagagccg agggtctgga gccaggtgtc ggagaccacc tcctctgggg ccgaggccag    3420
tgaggttcag gcagacttgc ggcagcagcg gcgagcagag gcccccgccc cagggtgcag    3480
tgagcttccc gaagacagtt actctgaggg gagcacggca gatatgacca acactgctga    3540
cctcctggag cagatccctg acctcggaga ggatgtcaaa gatccagagg actgcttcac    3600
tgaaggctgt gtccgccgct gtccctgctg caccgtggac accacacagg cccacgggaa    3660
ggtctggtgg aggctgcgca agacctgcta ccgcatcgtg gagcacagct ggttcgagac    3720
gttcatcatc ttcatgatcc tgctcagcag tggcgcactg gcctttgagg acatctacct    3780
ggaggagcgg aagaccatca aggtcctgct ggagtacgcc gacaagatgt tcacctacgt    3840
cttcgtgctg gagatgctcc tcaagtgggt ggcctacggc ttcaagaagt acttcaccaa    3900
cgcctggtgc tggcttgatt tcctcatcgt ggacgtcttg ctgatcagcc tggtggccaa    3960
cgccctgggc tttgctgaga tgggccccat caagtcactg cggaccttgc gtgcgctcag    4020
```

|  |  |  |  |  | |
|---|---|---|---|---|---|
| accccctgcga | gccctgtcac | gatttgaggg | catgagggtt | gtggttaacg | ccctggtggg | 4080 |
| cgccatccca | tccatcatga | acgtcctcct | cgtctgcctc | atcttctggc | tcatcttcag | 4140 |
| catcatgggc | gtgaacctct | tcgcggggaa | gtttgggaga | tgcatcaacc | agaccgaggg | 4200 |
| agacctgccc | ttgaactata | ccatcgtgaa | caacaagagc | gactgtgagt | ctttcaatgt | 4260 |
| gactggcgaa | ttgtactgga | ccaaggtgaa | ggtcaacttt | gacaacgtgg | gggccgggta | 4320 |
| cctggcccett | ctgcaggtgg | caacatttaa | aggctggatg | gacatcatgt | atgcagctgt | 4380 |
| agactccagg | gggtacgagg | agcagccccca | gtgggaatac | aacctctaca | tgtatatcta | 4440 |
| ttttgtcatc | ttcatcatct | tgggtctttt | cttcaccctg | aacctgttca | tcggtgtcat | 4500 |
| cattgacaac | ttcaaccagc | agaagaaaaa | gttaggggggc | caggacatct | tcatgacaga | 4560 |
| ggagcagaag | aagtactaca | acgccatgaa | gaagctgggc | tccaagaagc | cccagaagcc | 4620 |
| catcccacgg | cccctgaaca | agtaccaggg | cttcatattc | gacattgtga | ccaagcaggc | 4680 |
| cttcgacgtc | accatcatgt | ttctcatctg | cttaaacatg | gtgaccatga | tggtggagac | 4740 |
| agacgaccag | agcccccgaga | aggtcaacat | cttggccaag | atcaacctgc | tgttcgtggg | 4800 |
| catcttcaca | gccgagtgta | tcttcaagat | ggttgccctg | cgccactatt | acttcaccaa | 4860 |
| cagctggaac | atcttcgact | tcgtggttgt | catcctctcc | atcgtaggca | ctgtgctctc | 4920 |
| agacatcatc | cagaagtact | tcttctcccc | gacgctcttc | cgcgtcatcc | gcctggcccg | 4980 |
| catcagccgc | atcctcaggc | tgatccgcgg | ggccaagggc | atccgcacgc | ttctcttcgc | 5040 |
| cctcatgatg | tccctgcccg | cgctcttcaa | catcgggctg | ctgctcttcc | tcgtcatgtt | 5100 |
| catctactcc | atcttcggca | tggccaactt | cgcctacgtc | aagtgggagg | ctggcatcga | 5160 |
| cgacatgttc | aacttccaga | ccttcgccaa | cagcatgctg | tgcctcttcc | agatcaccac | 5220 |
| gtcggcgggc | tgggatgggc | tcctcagccc | catcctcaac | acggggcccc | cctactgcga | 5280 |
| cccccaacctg | cccaacagca | acggctcccg | ggcaactgc | gggagcccccg | cggtgggcat | 5340 |
| cctcttcttc | accacctaca | tcatcatctc | cttcctcatt | gtggtcaaca | tgtacatcgc | 5400 |
| catcatcctg | gagaacttca | gcgtggccac | ggaggagagc | acggagcccc | tgagtgagga | 5460 |
| tgacttcgac | atgttctacg | agatctggga | gaagttcgac | ccggaggcca | cccagttcat | 5520 |
| cgagtatttg | gccctgtctg | acttcgccga | tgccctgtca | gagccactcc | ggatccccaa | 5580 |
| gcccaaccag | ataagcctca | tcaatatgga | cctgcccatg | gtgagtggag | accgcatcca | 5640 |
| ctgcatggac | atcctctttg | ccttcaccaa | gagggtcctg | ggcgaatctg | ggagatgga | 5700 |
| cgccctgaag | atccagatgg | aggagaagtt | catggcggcc | aacccgtcca | agatctccta | 5760 |
| cgagcccatc | accaccacgc | tgcggcgaa | gcacgaggag | gtgtcggcca | cgatcatcca | 5820 |
| gcgggccttc | cgccggcacc | tgctgcagcg | ctccgtcaag | cacgcctcct | tcctctaccg | 5880 |
| ccagcaggcg | ggcagcagcg | gcctctcgga | ggaggacgcc | cccgagcagg | agggcctcat | 5940 |
| cgcctacatg | atgaacgaga | acttctcccg | ccgcccccggc | ccgccctcca | gctcctccgt | 6000 |
| ctcctccacg | tccttcccgc | cctcctacga | cagcgtcacc | agggccacca | gcgacaacccc | 6060 |
| ccaggtgcgg | gcgtctgact | acagcccaag | cgaggatctc | gccgacttcc | ccccaaccccc | 6120 |
| cgacagggac | cgtgagtcaa | tcgtgtgagc | gcagcccagg | ggaggggggc | gccagcgcag | 6180 |
| agcatcgcgg | caaacccccaaa | ggcagcccca | gcccagcagt | cgctgggccg | tccgaccttt | 6240 |
| gctttgggct | tcgggagtga | gaggagcctc | ggccccgtgg | accgacaagg | cagagtcctg | 6300 |
| tgcaccgcgc | tgatgctgg | aagcacttgg | ccgagctgtc | tgtctggggt | taccagtcct | 6360 |
| gggggctggg | tctggtccgg | caacgctctg | gggctctgac | caccacctcc | atcccagctg | 6420 |

```
ctgaggcaaa atgcgaaacc gagactgtgt atgttgtgaa tgggctttca taaatttatt    6480
atatttgaaa aaaaaaaaaa aaa                                             6503

<210> SEQ ID NO 17
<211> LENGTH: 2732
<212> TYPE: DNA
<213> ORGANISM: D. melanogaster

<400> SEQUENCE: 17
gcgacgactg tcgtcagtca gtcaatcaat cagtcagtca gtcagtcagt ccgtcagtca      60
gtcggtcagt cagttagtca gccagctagt cagttagcta gtcattcatt cagtcagtca     120
atcagtcagt gtgtcaatct gacaattgga gtttctatcc agacttcaat attttttac     180 ctcgctcaaa acccccccact cgcactttaa ataataaaaa aaagcaggtg gtgcgtgccg    240
cgtagccgcg cgtgattctt gttgttgttt ttttttttc ggtgaatctc ttgtaaccat      300
gtaccaaagt tctttgccgc gaaaactaaa atgaaaacga aagtgaaaat gagcgaatgg     360
cagccgcggc cacagcaatc gatccatgac acaaccagtg acaagcagtc ccccagtgaa     420
accgcatccg catccgagtc cgataccgat aaagattctg aatcggagtg agtgccgcgt     480
ccgagagcgt tccctgtcca cgtccaccat cggcggagca ggtgtgcctg aggcccacct     540
ggtggcatgg ccgccgttgc cggcctctat ggccttgggg aggatcgcca gcaccgcaag     600
aagcagcagc aacagcagca gcaccagaag gagcagctcg agcagaagga ggagcaaaag     660
aagatcgccg agcggaagct gcagctgcgg gagcagcagc tccagcgcaa ctccctcgat     720
ggttacgggt cttttgcccaa attgagcagt caagacgaag aaggggggggc tggtcatggc    780 tttggtggcg gaccgcaaca cttttgaaccc attcctcacg atcatgattt ctgcgaaaga    840
gtcgttataa atgtaagcgg attaaggttt gagacacaac tacgtacgtt aaatcaattc     900
ccggacacgt gcttgggga tccagctcgg agattacggt actttgaccc gcttagaaat      960 gaatatttt ttgaccgtag tcgaccgagc ttcgatgcga ttttatacta ttatcagagt     1020
ggtggccgac tacggagacc ggtcaatgtc cctttagacg tatttagtga agaaataaaa     1080
ttttatgaat taggtgatca agcaattaat aaattcagag aggatgaagg ctttattaaa    1140
gaggaagaaa gaccattacc ggataatgag aaacagagaa aagtctggct gctcttcgag     1200
tatccagaaa gttcgcaagc cgccagagtt gtagccataa ttagtgtatt tgttatattg     1260
ctatcaattg ttatattttg tctagaaaca ttacccgaat ttaagcatta caaggtgttc    1320
aatacaacaa caaatggcac aaaaatcgag gaagacgagg tgcctgacat cacagatcct    1380 ttcttccta tagaaacgtt atgtattatt tggtttacat ttgaactaac tgtcaggttc    1440
ctcgcatgtc cgaacaaatt aaatttctgc agggatgtca tgaatgttat cgacataatc    1500
gccatcattc cgtactttat aacactagcg actgtcgttg ccgaagagga ggatacgtta    1560
aatcttccaa aagcgccagt cagtccacag gacaagtcat cgaatcaggc tatgtccttg    1620
gcaatattac gagtgatacg attagttcga gtatttcgaa tatttaagtt atctaggcat    1680
tcgaagggtt tacaaatatt aggacgaact ctgaaagcct caatgcggga attaggttta    1740
cttatatttt tcttatttat aggcgtcgta ctcttctcat cggcggttta ttttgcggaa    1800
gctggaagcg aaaattcctt cttcaagtcc atacccgatg cattttggtg ggcggtcgtt    1860
accatgacca ccgttggata tggtgacatg acacccgtcg gcgtttgggg caagattgtg    1920
ggatcacttt gtgccattgc tggcgtgctg accatcgcac tgccggtgcc ggtcatcgtc    1980
agcaatttca actacttcta tcaccgcgaa acggatcagg aggagatgca gagccagaac    2040
```

| | |
|---|---|
| tttaatcacg ttactagttg tccatatttg ccaggtacat taggtcaaca catgaagaaa | 2100 |
| tcatcattgt ctgagtcctc atcggatatg atggatttgg acgatggtgt cgagtccacg | 2160 |
| ccgggattga cagaaacaca tcctggacgc agtgcggtgg ctccattttt gggagcccag | 2220 |
| cagcagcagc aacaacaacc ggtagcatcc tcgctgtcga tgtcgatcga caaacaactg | 2280 |
| cagcacccac tgcagcacgt gacgcagacg caactgtacc aacagcagca acagcagcag | 2340 |
| cagcagcagc aaaacggctt caagcagcag cagcaacaga cgcagcagca gctgcaacag | 2400 |
| caacagtccc acacaataaa cgcaagtgca gcagcggcga cgagcggcag cggcagtagc | 2460 |
| ggtctcacca tgaggcacaa taatgccctg ccgttagta tcgagaccga cgtttgacta | 2520 |
| ctggtgcaaa agacgttgcg tggtataaat ttggccttga caggagttac gttggatgcc | 2580 |
| agaaacgact acaaaagctg tttatattta atttaagtag aacaaataac aaaaacaaat | 2640 |
| ttaatctatt gctaaattaa attaaaatct aaattaaaat ctaaattaat ttaattaaat | 2700 |
| tatagattta atgataaaca acactaaaaa aa | 2732 |

<210> SEQ ID NO 18
<211> LENGTH: 3756
<212> TYPE: DNA
<213> ORGANISM: Homo sapiens

<400> SEQUENCE: 18

| | |
|---|---|
| gtcgggatgg aggtgagaag acggccgtga cgcgcgcccg cggggccccc tgcaccccca | 60 |
| gcagcccaca cgcgctccctg cccccctccc ccgcagcagc gggccttgcc gtcgagtgac | 120 |
| agcggcctgg gggggcaggg ggggcggggg cggccggatc agcgatgccg gcgggcatga | 180 |
| cgaagcatgc ctcccgctcc accagctcgc tgccgcccga gcccatggag atcgtgcgca | 240 |
| gcaaggcgtg ctctcggcgg gtccgcctca acgtcggggg gctggcgcac gaggtactct | 300 |
| ggcgtacccct ggaccgcctg ccccgcacgc ggctgggcaa gctccgcgac tgcaacacgc | 360 |
| acgactcgct gctcgaggtg tgcgatgact acagcctcga cgacaacgag tacttctttg | 420 |
| accgccaccc gggcgccttc acctccatcc tcaacttcta ccgcactggg cgactgcaca | 480 |
| tgatggagga gatgtgcgcg ctcagcttca gccaagagct cgactactgg ggcatcgacg | 540 |
| agatctacct ggagtcctgc tgccaggccc gctaccacca gaagaaagag cagatgaacg | 600 |
| aggagctcaa gcgtgaggcc gagaccctac gggagcggga aggcgaggag ttcgataaca | 660 |
| cgtgctgcgc agagaagagg aaaaaactct gggacctact ggagaagccc aattcctctg | 720 |
| tggctgccaa gatccttgcc ataatttcca tcatgttcat cgtcctctcc accattgccc | 780 |
| tgtccctcaa cacgctgcct gagctacaga gcctcgatga gttcggccag tccacagaca | 840 |
| accccccagct ggcccacgtg gaggccgtgt gcatcgcatg gttcaccatg gagtacctgc | 900 |
| tgaggttcct ctcctcgccc aagaagtgga agttcttcaa gggcccactc aatgccattg | 960 |
| acttgttggc cattctgcca tactatgtca ccatttttcct caccgaatcc aacaagagcg | 1020 |
| tgctgcaatt ccagaatgtc cgccgcgtgg tccagatctt ccgcatcatg cgaattctcc | 1080 |
| gcatccttaa gcttgcacgc cactccactg gcctccagtc tctgggcttc actttgcgga | 1140 |
| ggagctacaa tgagttgggc ttgctcatcc tcttccttgc catgggcatt atgatcttct | 1200 |
| ccagccttgt cttctttgct gagaaggatg aggacgacac caagttcaaa agcatcccag | 1260 |
| cctcttttct gtgggccacc atcaccatga ctactgttgg gtatggagac atctaccccca | 1320 |
| agactctcct ggggaaaatt gttggggggac tctgctgcat tgcaggagtc ctggtgattg | 1380 |
| ctcttcccat ccccatcatc gtcaataact tctctgagtt ctataaggag cagaagagac | 1440 |

```
aggagaaagc aatcaaacgg cgagaggctc tggagagagc caagaggaat ggcagcatcg      1500
tatccatgaa catgaaggat gcttttgccc ggagcattga gatgatggac attgtggttg      1560
agaaaaatgg ggagaatatg ggtaagaaag acaaagtaca agataaccac ttgtctccta      1620
acaaatggaa atggacaaag aggacactgt ctgaaaccag ctcaagtaag tcctttgaaa      1680
ccaaggaaca gggatcccct gaaaaagcca gatcgtcttc tagtcctcag cacctgaacg      1740
ttcagcagtt ggaagacatg tacaataaga tggccaagac ccaatcccaa cccatcctca      1800
ataccaagga gtcagcagca cagagcaaac caaggaagaa acttgaaatg agagtatcc       1860 ccagccccgt agccctctg cccactcgca cagaaggggt cattgacatg cgaagtatgt       1920
caagcattga tagtttcatt agctgtgcca cagacttccc tgaggccacc agattctccc      1980
acagcccttt gacatcactc cccagcaaga ctggggggcag cacagcccca gaagtgggct     2040
ggcggggagc tctgggtgcc agtggtggta ggtttgtgga ggccaacccc agccctgatg      2100
ccagccagca ctctagtttc ttcatcgaga gccccaagag ttccatgaaa actaacaacc      2160
ctttgaagct ccgagcactt aaagtcaact tcatggaggg tgaccccagt ccactcctcc      2220
ccgttctagg gatgtaccat gaccctctca ggaaccgggg gagtgctgcg gctgctgtcg      2280
ctggactgga gtgtgccacg cttttggaca aggctgtgct gagcccagag tcctccatct      2340
acaccacagc aagtgctaag acacccccccc ggtctcctga gaaacacaca gcaatagcgt     2400
tcaactttga ggcgggtgtc caccagtaca ttgacgcaga cacagatgat gagggacagc      2460
tgctctacag tgtggactcc agccccccca aaagcctccc tgggagcacc agtccgaagt      2520
tcagcacggg gacaagatcg gagaaaaacc actttgaaag ctccccttta cccacctccc      2580
ctaagttctt aaggcagaac tgtatttact ccacagaagc attgactgga aaaggcccca      2640
gtggtcagga aaagtgcaaa cttgagaacc acatctcccc tgacgtccgt gtgttgccag      2700
ggggaggagc ccatggaagc acacgagatc agagcatctg aactgccctg ccttggagga     2760
gagacttttg ggtgaggtcc aaagaggaga gctgttcagc ttacctgcca cagagctttt      2820
ctgcatgaac tctggaacag aaaggccctg taaagccctc agagagaaga gagactccag      2880
agaaggctcc ctaagacctt gagagccatg acaggtccat cagcatgaag ttggccaagc      2940
catagggcac agcacctcct tgtaacaact ctatagccct cttgggagaa tgacatgagt      3000
ggaactcaca gccaccacta ccaccacttt agacaggacc gaggccacat actccccatt      3060
ctctcgtggc tttccatctc agcctcggag ggcaacattg acagtcctcc tggcttcagc      3120
tagagaagga tgctggaaca gcggctggt gttgaaagag tgggttgacc aatttggtat       3180
tgaatgttgc ccagccaccc ctaggaacac ctgtccatca cctcctggat ggattccact      3240
gttagacagc tacagggaat gattggtcat ggggaagtct ctgcgccata agccacgatc      3300
ccagcgcaaa acccttactc aaatgtcttc attgacttcg gtatttcata gtacctgaga      3360
ttttattttg agataccatc agggtgagtt gcaccacttg tactcaattc taattgcccc      3420
ctggcaatct gggaagggtt cagaaggtgg gcacccagcc aacagcatga actcagagca      3480 ttgtttttagg gttggaggag gaacacgctt tctttacatc actagtgtag actcaaaaga     3540
tatgcaagtg tcaaatatgc aaaagaaata gtttattcaa agagactgtg tgttactgaa      3600
gaacagcata aaaatatgat ttttttactt gcaaaaatga aaggaaaaaa ataccacgca      3660
ttgaaatgcc cagttcagac tgaataattc ctgctgcagc aaggaaagta cctactataa      3720
tagaaattct gttttgtttt ctgtggtttt caagtt                                3756
```

<210> SEQ ID NO 19
<211> LENGTH: 2882
<212> TYPE: DNA
<213> ORGANISM: Oryctolagus cuniculus

<400> SEQUENCE: 19

```
cctggggccg tcgggatgga ggtgagaaga cggccgtgac gcgcgcccgc gccccgcctg      60
cacgccagcg gcccgcagcg ctccctgccc ccctcgcccg ccgcagcagc gggccttgcc     120
gtcgagtgac agcggcctgg gggggcgggg ggggcggggg cggccggacc agcgatgccg     180
gcgggcatga cgaagcatgg ctcgcgctcc gccagctcgc tgccgccgga gcccatggag     240
atcgtgcgca gcaaggcgtg ctctcggcgc gtccgcctca cgtcggggg cctggcgcac     300
gaggtgctgt ggcgcaccct ggaccgcctg ccccgcacgc ggctgggcaa gctccgcgac     360
tgcaacacac acgactcgct gctcgaggtg tgtgacgact acagcctgga cgacaatgag     420
tacttcttcg accggcaccc gggcgccttc acctccatcc tcaacttcta ccgcacgggg     480
cggctgcaca tgatggagga gatgtgcgcg ctcagcttca gccaggagct tgactactgg     540
ggcatcgacg agatctacct ggagtcctgc tgccaggcgc ggtaccacca gaagaaggag     600
cagatgaatg aggaacttaa gcgcgaggcc gagacgctcc gtgagcgcga gggcgaggag     660
tttgacaaca cgtgctgcgc ggagaagcgc aagaagctgt gggacctgct ggagaagccc     720
aactcctccg tggccgccaa gatcctggcc atcatctcca tcatgttcat cgtcctctcc     780
accatcgccc tgtccctcaa cacgctgccc gagctgcaga gcctcgacga gttcggccag     840
accacggaca ccccagct ggcccacgtg gaggccgtgt gcatcgcgtg gttcaccatg     900
gagtacctgc tgcgcttcct ctcctcgccc aagaagtgga agttcttcaa gggcccgctc     960
aacgccatcg acctgctggc catcctgccc tactacgtca ccatcttcct caccgagtcc    1020
aacaagagcg tgctgcagtt ccagaacgtg cggcgcgtgg tccagatctt ccgcatcatg    1080
cgcatcctgc gcatcctgaa gctggcgcgg cactccaccg gcctccagtc cctgggcttc    1140
accctgcgga ggagctacaa cgagctgggc ttgctcatcc tcttcctcgc catgggcatc    1200
atgatcttct ccagcctcgt cttctttgcc gagaaggatg aggacgacac caagttcaaa    1260
agcatcccgg cctctttctg gtgggccacc atcaccatga cgactgtggg gtatggagac    1320
atctacccca agactctcct ggggaaaatt gtagggggc tctgctgtat cgccggggtc    1380
ctggtgattg ctcttcccat ccccatcatc gtcaacaact tctccgagtt ctacaaggag    1440
caaaagaggc aggagaaagc gatcaagcgc agagaggctc tggagagagc caagaggaat    1500
ggcagcatcg tatccatgaa catgaaggac gctttcgccc ggagtgtcga gatgatggac    1560
atcgtggtgg agaagaacgg ggagaattg gcgaagaagg aaaaagtaca agataaccac    1620
ttgtctccca caagtggaa gtggacaaag aggaccctgt ccgaaaccag ctcaagtaag    1680
tcctttgaga cgaaggagca gggctcccct gagaaagcca gatcctcgtc gagtccccag    1740
cacctgaacg tgcagcagct ggaagacatg tacaacaaga tggccaagac ccagtcgcag    1800
cccgtcctca caccaagga ggcagcggca cagagcaagc cgaaggaaga actggaaatg    1860
gagagcatcc caagccccgt ggcccctctg cccactcgca ccgagggggt catcgacatg    1920
cgaagtatgt caagcattga cagctttatc agctgtgcca cggacttccc cgaagccacc    1980
aggttctccc cacagccccct tggcttccctc cccaccaagg ctggggggcgg gcggccccca    2040
gagctgggct ggcggggagc cctgggtgcc agcgggggcc ggctcgtgga ggccaacccc    2100
accccgatg ccagccacg ctccggtttc ttcatcgaga gccccaagag ttccatgaag    2160
accaacaacc ccttgaagct ccgagcactc aaagtcaact ttatggccgg cgagcccggt    2220
```

```
ccactcctcc ctgtcctggg gatgtaccat gaccctctga ggacccgggg gggtgctgcg    2280
gctgctgtcg ccggcctgga gtgcgccaca ctcttggaca agcctgtgct gagcccagag    2340
tcctccatct acaccacagc gagtgcgagg acacccccc ggtcgcccga gaagcccaca     2400
gcaatagcat tcaatttcga ggcaggcgtc caccagtaca ttgatgccga cacagatgac    2460
gagggccagc tgctctacag tgtagactcc agccctccca agagcctcca cggggggcgcc  2520 agtcccaagt gcagcatcgg ggcgaggtca gaaaagaacc actttgaaag tgcccccta    2580 cccacctccc cgaaattctt gaggcagaac tgtatttact ccacagaagg gttgactgga    2640
aaaagcctca gcggccagga aaagtgcaaa ctcgggaacc acatctcccc cgacgtccgc    2700
gtgttgccag ggggaggagc tcacgggagt actcgggatc agagcctctg aaccacccc    2760 cccccacct gccgtggagg ggagactgtg gccgcgccc agagtggggg ggctgttcct     2820
ctgacctgcc atagagcttt tctgcttgaa ctctgacgca gaaaagccct gcagagcccc   2880
ca                                                                  2882

<210> SEQ ID NO 20
<211> LENGTH: 2046
<212> TYPE: DNA
<213> ORGANISM: Xenopus laevis

<400> SEQUENCE: 20
ttcggcacga gtggaaacaa gcctccttcc aagtcatgtt tgaaaggaaa tatgggcaaa      60
aacgaggaca gcgacaaaat tgtcattaat gttgggggta tcaggcatga gacctacagg     120
agtaccccca aaaccttgcc aggtaccaga ctctcctggc tcactgagcc tgatgccttt     180
agtaactttg actatgaccc caaaacagac gagttcttct ttgacagaca ccctcaagtc     240
tttgcctgtg tcttgaacta ctataggact gggaagctgc actgtccctc cgatgtgtgc    300 ggaccctgt acgaggaaga gttggctttt tggggggattg atgagactga tgtgaggca    360 tgttgttgga tgaattacag gcagcacagg gatgcagagg aagccctgga tagctttgag    420
actccagagc cagaggagga agaggatgga gatctgaaaa gactctgcct ccaagaagat    480
ggtagaaagc tgggctggtg gaagaggttg cggcctaaag tctgggctct cttttgaggat   540 ccctactctt caaaatatgc caggtatatc gccttagctt ccctattctt catactcatc    600
tccatcacaa cgttctgcct tgagacccat gaggcattta atgatgtcaa caacaagact    660
gaggtcttca cacaaggcaa catcactaag acggagacca tattggaaat ggagactgcg    720 cctttctca attacgtaga aggcatttgt gtgatctggt tcactttga gtttctaata     780 cgtgttattt tctgcccaga taaaatggag ttcattaaaa gcagcttaaa cattatagac    840
tttgtggcca ttttacccctt ctacttggaa attggcttga gtggcttgtc ttccaaagca   900
gccaaggatg ttctcggttt ccttcgggtt gttcgatttg ttaggatcct gagaatcttt   960
aagctcactc gccatttgt tgggctcagg gttcttggcc acactctacg agccagtaca   1020
aatgagtttc tccttcttat catattttg gcacttggag ttttaatctt cgctaccatg   1080
atatactacg ccgaaaggat tggtgctgac ccagatgaca tcactggaag taagcacacc   1140
tacttcaaaa acatcccaat agggttttgg tgggctgtcg taactatgac aactttggga   1200 tatgggaca tgtacccaat gacttggtct ggcatgttgg tgggtgctct ttgtgctttg   1260
gcaggtgtgc taactattgc tatgccagtc cctgttattg tcaacaattt tggaatgtac   1320
tactcccttg ctatggctaa gcaaaagcta ccaaagaaaa agaataaaca tattcccga    1380 cctcctctac ctggatcacc caattactgt aaaccagact tgcagtctcc acatagaagt   1440
```

| | |
|---|---|
| gctcaaggag atgcctgccc tttagctcag gaggaaatca ttgagatcaa cagagcagac | 1500 |
| tccaagcaga atggggatgc tgcaaatgct gcactggcca atgaagattg ccctactata | 1560 |
| gaccaggctc tgtcaccaga ggaaaagtca cctatcacgc tggtgggag ggagagatat | 1620 |
| aatcgtgatc gtgcttgctt cctgttgacc acgggagact ttgcacattc cccagatggc | 1680 |
| aacatccgca aaggttatga aaaatcccgg agtctaaaca gcatagctgg catgagtgga | 1740 |
| aatatgctca gactgtctcc tatctccacc ccatttgggt caccatctgc agtgagacgc | 1800 |
| ccacggtctc ccattccctc catcttatag catggactca accaactgat aaggggaaca | 1860 |
| ttaactagta atacaataa aaacaaacag acatcaacaa tggcaagaga acaaaataag | 1920 |
| agactttaac aaattctatt attttttaag tggttgatga aaatataga ttatatgcag | 1980 |
| atatatttaa aaaaaaagt ttggctttta aaaaaaaaa agacaaggaa aaaaaaaaa | 2040 |
| aaaaaa | 2046 |

<210> SEQ ID NO 21
<211> LENGTH: 3591
<212> TYPE: DNA
<213> ORGANISM: Xenopus laevis
<400> SEQUENCE: 21

| | |
|---|---|
| atggcaacct ggaacgcatc tcagatcatc ttaaatagta tgagcaacat cattgagagc | 60 |
| ccgcaatcca aacctcgccc cgtaatggcg tccaatgggg cgtccttatt tattccagtc | 120 |
| actatggagg tgccttgtga tcaggggaca cgtatgtggt gggcattcct ggcctcttct | 180 |
| atggtgacgt ttttcggagg tctgttcatt atcctggtgt ggaggacatt caaatacctg | 240 |
| tggactgtat gttgtcactg tgggggcaaa acaaggagg cacagaaagt tgtaaatgta | 300 |
| gcaagcagcc aggtcactga tggggactac aagccaactg atgataaaga agaagtagga | 360 |
| gtggcagaag ttggctggat gacatcagtt aaagactggg caggcgtgat gatttctgcc | 420 |
| cagaccctaa caggtcgtgt gttggttgtg acagtctttg ctctgagcat ggagcactt | 480 |
| atgatatact ttattgactc atcaaaccct attgaatctt gtcaaaactt ttacaaggat | 540 |
| ttcactcttc aaatagacat ggccttcaac atcttctttc tgctatattt tggcttgcgg | 600 |
| ttcatagctg ctaatgacaa gctttggttc tggctggaag tgaattcagt tgtggatttc | 660 |
| ttcacagtac ctcctgtgtt tgtgtcagtg tatctaaaca ggagttggct tgggctgagg | 720 |
| ttcctccgtg ctttgcggct aatacaattt tcagaaatcc tgcaattttt aaacatttta | 780 |
| aaaacaagta attccattaa gctggtgaac ctatgctcca tctttatcag tacgtggctg | 840 |
| actgcagctg gcttcatcca tttggtggag aactcaggag atccctggag aaattttgaa | 900 |
| aactcccagg accttctta ctgggaatgt atgtacttgc tcatggtgac tatgtccaca | 960 |
| gtgggctatg gagatgttta tgcaaaaacc cccttggtc gtctcttcat ggtcttcttc | 1020 |
| attctcggcg gtttggccat gtttgccagc tacgtccccg aaatcataga gttaatagga | 1080 |
| aaccgaaaga aatatggtgg ttcatatagt gcagttagtg gacggaagca tattgtggtc | 1140 |
| tgtggtcaca tcacattaga aagcgtgtcc aacttcttga aagacttcct gcacaaggac | 1200 |
| cgagatgatg tgaatgtgga gattgtattt ttgcacaaca tatccccaaa tttggagttg | 1260 |
| gaagctttat ttaagaagca ctttactcag gtagaatttt accagggatc tgttctgaat | 1320 |
| ccacacgacc tggcaagagt taagattgag tctgcagatg cctgtctgat ccttgctaac | 1380 |
| aagtactgtg ctgaccctga tgctgaagat gcttctaaca ttatgagagt catctccatc | 1440 |
| aaaaattatc atcccaagat aagaatcatc actcagatgt tgcagtacca caataaggct | 1500 |

-continued

```
cacctactta atatacccag ctggaattgg aaagatggag atgatgccat ctgccttgct    1560
gagctgaaac ttggttttat tgctcagagt tgtttggctc aaggtctatc aaccatgctg    1620
gctaatcttt tttccatgcg ttcctttatt aagattgagg aagacacctg gcaaaagtat    1680
tacctggaag gagtggccaa tgaaatgtat acagaatatt tatccagtgc ttttgtgggc    1740
ctttcattcc ctgcagtttg cgagttgtgc tttgtgaagt tgaaactgct aatgatagct    1800
atcgagtaca agtcagagaa aggagagagc aggatcttaa tcaatccggg taaccatatg    1860
aaaataaaag aaggtaccct gggattttt attgccagtg atgccaaaga agtaaaacgg    1920
gcctttttt actgtaaagc atgtcatgat gacatcacag acccaaagcg gataaagaaa    1980
tgcgcctgca agagacttga agatgagcag ccatcagcct tgtcacccaa aaaaaagcaa    2040
cgaaatggag gaatgaggca ctctccaaac acttctccta acatgatgag gcatgatccc    2100
cttctcatga ctgggaatga tcaaattgat aatatggatt ctagcagtgt taaaagatat    2160
gattctactg gtatgttcca ctggtgtcca gccaaggaat tggataaagt gcttctgaca    2220
cggagtgaag ctgccatgac agtcctcagt gggcatgtgg ttgtctgcat ttttggagac    2280
atgacgtcgg cactgattgg agtacggaat ttggtgatgc cactgagagc cagcaatttc    2340
cattaccatg agctgaaaca tatagtcttt gttgggtccc ttgattacat taaaagagaa    2400
tgggaaacac tacacaactt cccaaaggtg tcaatattgc ctgggacacc gttaagtcga    2460
gcagatctaa gagctgtcaa cattaacctg tgtgacatgt gcgttatcct gtcagccaac    2520
cagaataata ttgatgatac atcactgcag gacaaagaat gcattttagc atctctcaac    2580
atcaaatcta tgcagtttga tgacagcata gggctcttgc aagcaaactc tcaagggttt    2640
acaccccag gtatggagag gtcatcacct gataatagcc cactgcatgg tgttgcaaga    2700
caggcatcca taactacagg agccaacatt cccataatta cagaacttgt gaacgactca    2760
aatgttcagt tcttggacca ggatgatgat gatgacccag atacagagtt atacttgact    2820
cagccctttg cctgtgggac agcatttgct gtcagtgtgt tggactccct catgagtgca    2880
acatacttca atgataacat cctgactctg atcagaactc tggtgactgg gggagcaaca    2940
ccagagctgg aagccctcgt tgcagaagag aatgctctgc gtggaggtta tagcaccca    3000
caaactctag caaacagaga ccgctgtcga gtagcccaat tagccttgta tgatggacca    3060
tttgcagatt tgggggatgg tggatgttat ggagacctt actgcaaagc attaaaaacc    3120
tacaacatgc tgtgctttgg tatataccga ctcagagatg cccacatcag cacacccagc    3180
cagtgtacca aaaggtatgt tataaccaac cctccatatg agtttgaact ggttcccaca    3240
gacctcatct tttgcctgat gcagttcgac cataatgcca gccaatcgcg agctagcctg    3300
tctcactctt cacactcctc gcactcgtct agcaaaaaaa gttcgtctgt tacctccata    3360
ctacacacag cctcagccaa ccgtcagaac agagtcaagg ctcgagattc ccgtgacaaa    3420
caaaaaatgg gccaagcaga aaagaaatgg tatacagatg aaacggaaaa caattatccc    3480
agaaacattc agattaagcc aatgagcaca catatggcta atcagattaa tcagtacaaa    3540
tcaacaagca gcttgatacc gccaatacga gaggttgaag atgaatgtta a            3591
```